United States Patent [19]
von Sprecher et al.

[11] Patent Number: 5,149,717
[45] Date of Patent: Sep. 22, 1992

[54] ALKANOPHENONES USEFUL FOR TREATING ALLERGIES

[75] Inventors: Andreas von Sprecher, Oberwil, Switzerland; Andreas Beck, Freiburg, Fed. Rep. of Germany; Bruno Schaub, Courroux, Switzerland; Robert W. Lang, Pratteln, Switzerland

[73] Assignee: Ciba-Geigy Corporation, Ardsley, N.Y.

[21] Appl. No.: 795,227

[22] Filed: Nov. 15, 1991

Related U.S. Application Data

[63] Continuation of Ser. No. 566,645, Aug. 13, 1990, abandoned, which is a continuation-in-part of Ser. No. 546,683, Jun. 28, 1990, abandoned, which is a continuation of Ser. No. 324,924, Mar. 17, 1989, abandoned.

[30] Foreign Application Priority Data

| Mar. 29, 1988 | [CH] | Switzerland | 1186/88-7 |
| Oct. 14, 1988 | [CH] | Switzerland | 3857/88-5 |
| Sep. 19, 1989 | [CH] | Switzerland | 3402/89-4 |

[51] Int. Cl.$^5$ ............ A61K 31/35; A61K 31/41; C07D 311/24; C07D 257/04
[52] U.S. Cl. ............ 514/456; 549/402; 548/253; 514/382
[58] Field of Search ......... 549/402; 548/253; 514/456, 382

[56] References Cited

U.S. PATENT DOCUMENTS

| 4,474,788 | 10/1984 | Bantick | 549/402 |
| 4,546,194 | 10/1985 | Miyano | 549/401 |
| 4,609,744 | 9/1986 | Young et al. | 549/402 |
| 4,649,215 | 3/1987 | von Sprecher et al. | 560/152 |
| 4,761,425 | 8/1988 | Girard et al. | 514/456 |
| 4,808,572 | 2/1989 | Beck et al. | 514/18 |

FOREIGN PATENT DOCUMENTS

| 17332 | 10/1980 | European Pat. Off. |
| 79637 | 5/1983 | European Pat. Off. |
| 0123543 | 10/1984 | European Pat. Off. |
| 134111 | 3/1985 | European Pat. Off. |
| 139809 | 5/1985 | European Pat. Off. |
| 147217 | 7/1985 | European Pat. Off. |
| 150447 | 8/1985 | European Pat. Off. |
| 206741 | 12/1986 | European Pat. Off. |
| 228045 | 7/1987 | European Pat. Off. |

*Primary Examiner*—Nicky Chan
*Attorney, Agent, or Firm*—Irving M. Fishman; Karen G. Kaiser

[57] ABSTRACT

Substituted alkanophenones of general formula

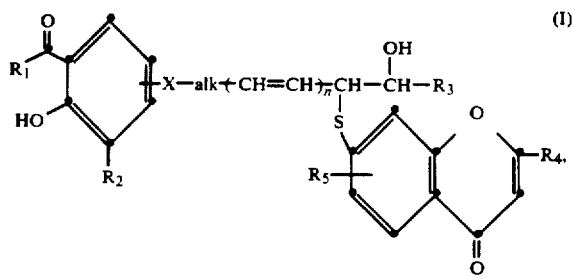

in which $R_1$ is unsubstituted or fluorinated lower alkyl, $R_2$ is hydrogen, or unsubstituted or fluorinated lower alkyl or lower alkenyl, X is lower alkylene, oxy, thio or a direct bond, alk is lower alkylene, n is 1 or 2, $R_3$ is phenyl that is unsubstituted or is substituted by unsubstituted or fluorinated lower alkyl, by etherified or esterified hydroxy, by unsubstituted or lower alkylated amino and/or by free, esterified or amidated carboxy, or is lower alkyl that is unsubstituted, substituted by fluoro and chloro or substituted by free esterified or amidated carboxy, $R_4$ is free, esterified or amidated carboxy or 5-tetrazolyl, and $R_5$ is hydrogen or lower alkyl, have leucotriene-antagonistic properties and can be used as anti-allergic active ingredients in medicaments.

14 Claims, No Drawings

ALKANOPHENONES USEFUL FOR TREATING ALLERGIES

This application is a continuation of application Ser. No. 566,645, filed Aug. 13, 1990, now abandoned, which is a continuation-in-part of our copending patent application Ser. No. 546,683, filed Jun. 28, 1990 which in turn is a continuation of our previous patent application Ser. No. 324,924, filed Mar. 17, 1989, now abandoned.

The invention relates to novel substituted alkanophenones of general formula

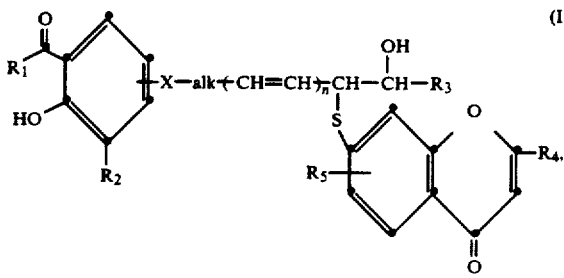

in which $R_1$ is unsubstituted or fluorinated lower alkyl, $R_2$ is hydrogen, or unsubstituted or fluorinated lower alkyl or lower alkenyl, X is lower alkylene, oxy, thio or a direct bond, alk is lower alkylene, n is 1 or 2, $R_3$ is phenyl that is unsubstituted or is substituted by unsubstituted or fluorinated lower alkyl, by etherified or esterified hydroxy, by unsubstituted or lower alkylated amino and/or by free, esterified or amidated carboxy, or is lower alkyl that is unsubstituted, substituted by fluoro or fluoro and chloro or substituted by free esterified or amidated carboxy, $R_4$ is free, esterified or amidated carboxy or 5-tetrazolyl, and $R_5$ is hydrogen or lower alkyl, and their salts, to processes for their preparation, to pharmaceutical preparations containing them as active ingredient, and to their use as active ingredients in medicaments.

The spatial arrangement shown in the above formula I for the preferred compounds in which the O atom of the hydroxy group is in the relative trans-configuration with the S atom is to be understood as follows: the symbols in the first line lie above the plane of the drawing and the symbols in the third line therefore lie below the plane of the drawing (or vice versa), which for the formula shown corresponds to the opposite configuration, (RS)—(SR), according to the Kahn-Ingold-Prelog convention at the carbon atom bonded to the sulphur atom, (C—S—), and the carbon atom carrying the hydroxy group, (C—OH). When n is 2, the enantiomers having the S(C—S—), R(C—OH)-configuration and, when n is 1, the enantiomers having the R(C—S—), S(C—OH)-configuration are especially preferred. In a vinylene or buta-1,3-dienylene radical represented by the symbol —(CH═CH)ₙ, the double bond or the double bond of the butadienylene radical originating from the carbon atom bonded to the radical alk is preferably, but not necessarily, in the cis-configuration, usually designated (Z), the other double bond then preferably, but again not necessarily, having the trans-configuration, usually designated (E).

Unsubstituted or fluorinated lower alkyl is lower alkyl or mono-, di- or poly-fluoro-lower alkyl.

Alkyl substituted by fluoro or by fluoro and chloro is, for example mono-, di- or polyfluoro-lower alkyl having up to and including 9 fluoro atoms or mono-, di- or polyfluoro-lower(di- or polychloro)-alkyl having 3 up to and including 7 fluoro and 2 up to and including 5 chloro atoms.

Etherified or esterified hydroxy is, for example, lower alkoxy or halogen, respectively.

Unsubstituted or lower alkylated amino is, for example, amino, lower alkylamino or especially di-lower alkylamino.

Free, esterified or amidated carboxy is carboxy, esterified carboxy, such as lower alkoxycarbonyl, or amidated carboxy, such as carbamoyl or N-mono- or N,N-di-lower alkylcarbamoyl or, as $R_3$, N-(benzenesulfonyl)-carbamoyl that is unsubstituted or substituted, preferably in the phenyl moiety, by lower alkyl, lower alkoxy and/or by halogen. N-(benzenesulfonyl)-carbamoyl that is unsubstituted or substituted in the phenyl moiety as indicated is, for example, unsubstituted or mono-substituted, preferably in the ortho-position. As a free, esterified or amidated carboxy substituent of $R_3$, carboxy is especially preferred, and as $R_4$ esterified carboxy, especially lower alkoxycarbonyl, is especially preferred.

Hereinbefore and hereinafter "lower" radicals and compounds are to be understood as being, for example, those radicals and compounds containing no more than 7 and, unless otherwise indicated, preferably no more than 4 carbon atoms (C atoms).

Lower alkyl is, for example, $C_1$–$C_7$alkyl, especially straight-chain $C_1$–$C_4$alkyl, such as methyl, ethyl, propyl, isopropyl, butyl or sec.-butyl, but may also be a branched-chain $C_1$–$C_4$alkyl, such as isobutyl or tert.-butyl, or a pentyl, hexyl or heptyl radical. Lower alkyl $R_1$, $R_5$ and as a substituent of phenyl or N-(benzenesulfonyl)-carbamoyl is preferably $C_2$–$C_5$alkyl, for example methyl; lower alkyl $R_3$ is preferably $C_3$–$C_7$alkyl, for example propyl, and lower alkyl $R_3$ is preferably $C_3$–$C_7$alkyl, for example propyl, butyl or pentyl.

Mono-, di- or poly-fluoro-lower alkyl $R_1$, $R_2$ or a substitutent of phenyl $R_3$ has, for example, up to and including 5 fluorine atoms and is, for example, ω-fluoro- or ω,ω,ω-trifluoro-$C_1$–$C_4$alkyl, such as trifluoromethyl, 2,2,2-trifluoroethyl or 3,3,3-trifluoropropyl. Fluorinated lower alkyl $R_1$ and as a substituent of phenyl $R_3$ is especially trifluoromethyl, and fluorinated lower alkyl $R_2$ is preferably ω,ω,ω-trifluoro-$C_2$–$C_4$alkyl, for example 3,3,3-trifluoropropyl.

Mono-, di- or polyfluoro-lower alkyl $R_3$ having up to and including 9 fluoro atoms is, for example, ω-fluoro-ω,ω,ω-trifluoro- or ω,ω,ω-1,ω-1-pentafluoro-$C_2$–$C_7$alkyl, such as 3,3,3-trifluoro- or 2,2,3,3,3-pentafluoropropyl, 3,3,3-trifluorobutyl, 3,3,4,4,4-pentafluorobutyl, 4,4,5,5,5-pentafluoropentyl or 5,5,6,6,6-pentafluorohexyl.

Mono-, di- or polyfluoro-lower(di- or polychloro)alkyl $R_3$ having 3 up to and including 7 fluoro and 2 up to and including 5 chloro atoms is, for example, ω,ω,ω-trifluor-ω,1-ω-1-dichloro-$C_3$–$C_6$alkyl, such as 2,2-dichloro-3,3,3-trifluoropropyl, 3,3-dichloro-4,4,4-trifluorobutyl, 4,4-dichloro-5,5,5-trifluoropentyl or 5,5-dichloro-6,6,6-trifluorohexyl.

Lower alkenyl $R_2$ is, for example, $C_2$–$C_4$alkenyl, such as vinyl, prop-1-enyl or especially prop-2-enyl (allyl).

Lower alkylene is, for example, straight-chain $C_1$–$C_7$alkylene, and in the case of X especially $C_1$–$C_3$alkylene, such as methylene or ethylene, and in the case of alk especially $C_2$-$C_6$alkylene, such as ethylene, 1,3-propylene, 1,4-butylene, also 1,5-pentylene or 1,6-hexylene.

Lower alkoxy is, for example, $C_1$-$C_4$alkoxy, such as methoxy.

Lower alkoxycarbonyl is, for example, $C_1$-$C_4$alkoxycarbonyl, such as methoxy-, ethoxy-, propoxy- or butoxy-carbonyl.

Lower alkylamino is, for example, $C_1$-$C_4$alkylamino, such as methyl-, ethyl-, propyl- or isopropyl-amino.

Di-lower alkylamino is, for example, di-$C_1$-$C_4$alkylamino, such as dimethylamino, diethylamino or N-ethyl-N-methylamino.

N-mono- or N,N-di-lower alkylcarbamoyl is, for example, N-$C_1$-$C_4$alkyl- or N,N-di-$C_1$-$C_4$alkyl-carbamoyl, such as N-methyl-, N-ethyl- or N,N-dimethyl-carbamoyl.

Halogen is, for example, halogen having an atomic number of up to and including 35, such as fluorine, chlorine or bromine.

Most of the compounds of formula I can, depending upon their individual character, also be in the form of salts. Those compounds which have sufficient acidity, such as, especially, those having carboxy, tetrazolyl or sulfamoyl groups, can form salts with bases, such as, especially, inorganic bases, preferably physiologically tolerable alkali metal salts, especially sodium and potassium salts. However, ammonium salts with ammonia or physiologically tolerable organic amines, such as mono-, di- or tri-lower alkylamines, for example diethylamine, mono-, di- or tri-(hydroxyalkyl)-amines, such as tris(hydroxymethyl)-methylamine, or D-glucosamine, also come into consideration.

The compounds of formula I and their salts exhibit advantageous pharmacological properties, especially a pronounced leucotriene-antagonism.

For example, in vitro in a concentration range of approximately from 0.001 to 1.0 μmol/l, they inhibit the contraction of a smooth muscle induced by leucotriene-$D_4$ ($LTD_4$). This so-called $LTD_4$-antagonism is detected experimentally, for example, as follows: in segments which have been removed from the ileum of a guinea pig weighing 300–400 g and which have been incubated in an organ bath in Tyrode's solution at 38° C. and while being gassed with a mixture of 95% oxygen and 5% carbon dioxide at a load of 1 g, contractions are induced with synthetic leucotriene $D_4$ (in potassium salt form) and are registered isotonically. The extent of the inhibition by the test compound is detected after a preliminary incubation of 2 minutes and is evaluated as IC50, that is to say the concentration which reduces the test contraction by 50%. The compounds of formula I also have excellent activity in vivo. In addition, they have a relatively long duration of action which is a very significant advantage both specifically and therapeutically. For example, in an in vivo bronchoconstriction standard test on guinea pigs, with aerosol administration of a solution containing from 0.0001 to 1% by weight of the test compound, a marked $LTD_4$-antagonistic effect was demonstrated. (A description of the test method can be found in the appendix after the Examples).

Surprisingly, many compounds of formula I also exert a pronounced inhibitory action on other physiologically important enzyme systems. For example, the inhibition of phospholipase $A_2$ obtained from human leucocytes was observed in the tested concentration range of approximately 0.5–50 μmol/l. (The experimental procedure for this determination is described in more detail in the appendix after the Examples.) Likewise, the inhibition of phospholipase C obtained from human thrombocytes was observed in the tested concentration range of approximately 1–100 μmol/l.

Owing to these valuable pharmacological properties, the compounds of formula I according to the invention can be used therapeutically in all cases where the action of leucotrienes results in pathological conditions, and alleviate or eliminate these conditions. Accordingly, they can be used, for example, for the treatment of allergic conditions and diseases, such as, especially, asthma, but also hay fever and obstructive pulmonary diseases, including cystic fibrosis. Owing to their anti-inflammatory activity, they are also suitable as inflammation-inhibiting agents, especially as external (topical) skin phlogistatics for the treatment of inflammatory dermatoses of any origin, as in mild skin irritations, contact dermatitis, exanthemas and burns, and also as mucous membrane phlogistatics for the treatment of inflammation of the mucosa, for example of the eyes, nose, lips, mouth and genital or anal region. They can also be used as sun screens. The high inhibitory effect on various blood factors also points to the possibility of the therapeutic use of the compounds of formula I where thrombosis and blood coagulation are indicated.

The invention relates especially to compounds of formula I in which $R_1$ is lower alkyl or mono-, di- or poly-fluoro-lower alkyl, $R_2$ is hydrogen, lower alkyl, lower alkenyl or mono-, di- or poly-fluoro-lower alkyl, X is lower alkylene, oxy or thio, alk is lower alkylene, $R_3$ is phenyl that is substituted by lower alkyl, lower alkyl, lower alkoxy, halogen, carboxy, lower alkoxycarbonyl, amino, N-mono- or N,N-di-lower alkylamino, carbamoyl, N-mono- or N,N-di-lower alkylcarbamoyl and/or by trifluoromethyl, or is lower alkyl, mono-, di- or polyfluoro-lower alkyl, mono-, di- or polyfluoro-lower (di- or polychloro)alkyl, carboxy-lower alkyl, lower alkoxycarbonyl-lower alkyl, carbamoyl-lower alkyl or N-mono- or N,N-di-lower alkylcarbamoyl-lower alkyl, $R_4$ is carboxy, lower alkoxycarbonyl, 5-tetrazolyl, carbamoyl, N-mono- or N,N-di-lower alkylcarbamoyl, or N-(benzenesulfonyl)-carbamoyl that is unsubstituted or substituted in the phenyl moiety by lower alkyl, lower alkoxy, halogen and/or by trifluoromethyl, and $R_5$ is hydrogen or lower alkyl, and to their salts, especially pharmaceutically acceptable salts.

The invention relates especially, for example, to those compounds of formula I in which $R_1$ is lower alkyl, $R_2$ is unsubstituted or fluorinated lower alkyl or lower alkenyl, and X, $R_3$, $R_4$ and $R_5$ are as defined above, and to their salts, especially pharmaceutically acceptable salts.

The invention relates preferably to those compounds in which the group X is bonded in the para-position to the $R_1$—C(=O) group, that is to say compounds of formula

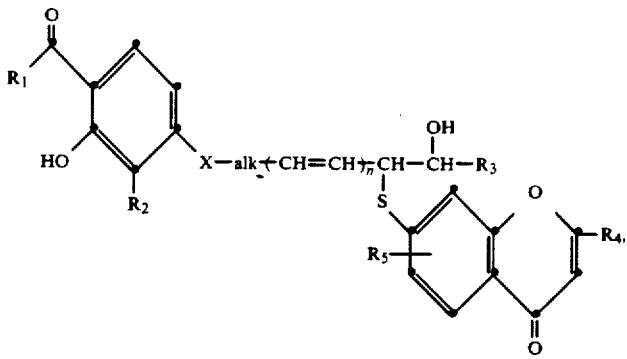

(Ia)

in which $R_1$, $R_2$, X, alk, n, $R_3$, $R_4$ and $R_5$ are as defined above, but preferably $R_1$ is lower alkyl, $R_2$ is unsubstituted or fluorinated lower alkyl or lower alkenyl, and-/or phenyl $R_3$ is preferably substituted as indicated, and to their salts, especially pharmaceutically acceptable salts.

The invention relates more especially to compounds of formula I and Ia in which $R_1$ is $C_1$–$C_4$alkyl, such as methyl, or ω,ω,ω-trifluoro-$C_1$–$C_4$alkyl, such as trifluromethyl, $R_2$ is $C_1$–$C_4$alkyl, such as propyl, $C_2$–$C_4$alkenyl, such as alkyl, ω,ω,ω-trifluoro-$C_1$–$C_4$alkyl, such as 3,3,3-trifluoropropyl, or secondly hydrogen, X is $C_1$–$C_3$alkylene, such as methylene, oxy or thio, alk is straight-chain $C_2$–$C_6$alkylene, such as ethylene, 1,3-propylene or 1,4-butylene, n is 1 or 2, $R_3$ is phenyl that is unsubstituted or substituted by $C_1$–$C_4$alkyl, such as methyl, $C_1$–$C_4$alkoxy, such as methoxy, halogen having an atomic number of up to and including 35, such as chlorine or bromine, trifluoromethyl, carboxy and/or by $C_1$–$C_4$alkoxycarbonyl, such as methoxycarbonyl, or is $C_1$–$C_8$alkyl, such as propyl or butyl, ω,ω,ω-trifluoro-$C_2$–$C_7$alkyl, such as 3,3,3-trifluoropropyl or 4,4,4-trifluorobutyl, ωω, ω-1,ω-1-pentafluoro-$C_2$–$C_7$alkyl, such as 2,2,3,3,3-pentafluoropropyl, 3,3,4,4,4-pentafluorobutyl, 4,4,5,5,5-pentafluoropentyl or 5,5,6,6,6-pentafluorohexyl, ω,ω,ω-Trifluor-ω-1,ω-1-dichloro-$C_3$–$C_6$alkyl, such as 2,2-dichloro-3,3,3-trifluoropropyl, 3,3-dichloro-4,4,4-trifluorobutyl, 4,4-dichloro-5,5,5-trifluoropentyl or 5,5-dichloro-6,6,6-trifluorohexyl, carboxy-$C_2$–$C_5$-alkyl, such as 3-carboxypropyl or 4-carboxybutyl, or $C_1$–$C_4$alkoxycarbonyl-$C_2$–$C_5$alkyl, such as 3-methoxycarbonylpropyl or 4-methoxycarbonylbutyl, $R_4$ is carboxy or N-(benzenesulfonyl)-carbamoyl, and $R_5$ is hydrogen, and when n is 1, the chain carbon atom bonded to the sulfur atom preferably has the (R)-configuration and the chain carbon atom bonded to the hydroxy group preferably has the (S)-configuration or, when n is 2, the chain carbon atom bonded to the sulfur atom preferably has the (S)-configuration and the chain carbon atom carrying the hydroxy group preferably has the (R)-configuration and the double bond joined to the radical alk is preferably in the cis-configuration and the additional double bond which may be present is preferably in the trans-configuration, and preferably to those compounds in which $R_1$ is $C_1$–$C_4$alkyl and $R_2$, X, $R_3$, $R_4$ and $R_5$ are as defined above and to their salts, especially pharmaceutically acceptable salts.

The invention relates especially, for example, to compounds of formula I and Ia in which $R_1$ is $C_1$–$C_4$alkyl, such as methyl, $R_2$ is $C_1$–$C_4$alkyl, such as propyl, $C_2$–$C_4$alkenyl, such as alkyl, or ω,ω,ω-trifluoro-$C_1$–$C_4$alkyl, such as 3,3,3-trifluoropropyl, X is $C_1$–$C_3$alkylene, such as methylene, oxy or thio, alk is straight-chain $C_2$–$C_6$alkylene, such as ethylene, 1,4-butylene or 1,6-hexylene, n is 1 or 2, $R_3$ is a group of formula —A—$R_3$' in which —A— is $C_1$–$C_4$alkylene, phenylene or a direct bond and $R_3$' is $C_1$–$C_4$alkyl, such as methyl, trifluoromethyl, carboxy or $C_1$–$C_4$alkoxycarbonyl, such as methoxycarbonyl, $R_4$ is carboxy or N-(benzenesulfonyl)-carbamoyl, and $R_5$ is hydrogen, and when n is 1, the chain carbon atom bonded to the sulfur atom preferably has the (R)-configuration and the chain carbon atom bonded to the hydroxy group preferably has the (S)-configuration or, when H is 2, the chain carbon atom bonded to the sulfur atom preferably has the (S)-configuration and the chain carbon atom carrying the hydroxy group preferably has the (R)-configuration and the double bond joined to the radical alk is preferably in the cis-configuration and the additional double bond which may be present is preferably in the trans-configuration, and to their salts, especially pharmaceutically acceptable salts.

The invention relates especially to compounds of formula Ia in which $R_1$ is $C_1$–$C_4$alkyl, such as methyl, $R_2$ is $C_1$–$C_4$alkyl, such as propyl, X is oxy, alk is $C_2$–$C_6$alkylene, such as ethylene, 1,3-propylene or 1,4-butylene, n is 1 or preferably 2, $R_3$ is phenyl substituted by $C_1$–$C_4$alkyl, such as methyl, $C_1$–$C_4$alkoxy, such as methoxy, halogen having an atomic number of up to and including 35, such as chlorine, trifluoromethyl or by $C_1$–$C_4$alkoxycarbonyl, such as methoxycarbonyl, or is $C_2$–$C_8$alkyl, especially $C_3$–$C_5$alkyl, such as propyl or butyl, ω,ω,ω-trifluoro-$C_3$–$C_5$alkyl, such as 3,3,3-trifluoropropyl or 4,4,4-trifluorobutyl, ω,ω,ω-1,ω-1-pentafluoro-$C_2$–$C_7$alkyl, such as 2,2,3,3,3-pentafluoropropyl, 3,3,4,4,4-pentafluorobutyl, 4,4,5,5,5-pentafluoropentyl or 5,5,6,6,6-pentafluorohexyl, ω,ω,ω-Trifluor-ω-1,ω-1-dichloro-$C_3$–$C_6$alkyl, such as 2,2-dichloro-3,3,3-trifluoropropyl, 3,3-dichloro-4,4,4-trifluorobutyl, 4,4-dichloro-5,5,5-trifluoropentyl or 5,5-dichloro-6,6,6-trifluorohexyl, or $C_1$–$C_4$alkoxycarbonyl-$C_1$–$C_4$alkyl, such as 3-methoxycarbonylpropyl or 4-methoxycarbonylbutyl, $R_4$ is carboxy, and $R_5$ is hydrogen, and when n is 1, the chain carbon atom bonded to the sulfur atom preferably has the (R)-configuration and the chain carbon atom bonded to the hydroxy group preferably has the (S)-configuration or, when n is 2, the chain carbon atom bonded to the sulfur atom preferably has the (S)-configuration and the chain carbon atom carrying the hydroxy group preferably has the (R)-configuration and the double bond joined to the radical alk is preferably in the cis-configuration and the additional double bond which may be present is preferably in the trans-configuration, and to their salts, especially pharmaceutically acceptable salts.

The invention relates preferably to compounds of formula Ia in which $R_1$ is $C_1$-$C_4$alkyl, such as methyl, $R_2$ is $C_1$-$C_4$alkyl, such as propyl, X is oxy, alk is $C_2$-$C_6$alkylene, such as ethylene or 1,4-butylene, n is 1 or preferably 2, $R_3$ is a group of formula —A—$R_3'$ in which —A— is $C_1$-$C_4$alkylene, such as ethylene, or phenylene, especially m-phenylene, and $R_3'$ is $C_1$-$C_4$alkyl, such as methyl, trifluoromethyl or $C_1$-$C_4$alkoxycarbonyl, such as methoxycarbonyl, $R_4$ is carboxy or N-(benzenesulfonyl)-carbamoyl, and $R_5$ is hydrogen, and when n is 1, the chain carbon atom bonded to the sulfur atom preferably has the (R)-configuration and the chain carbon atom bonded to the hydroxy group preferably has the (S)-configuration or, when n is 2, the chain carbon atom bonded to the sulfur atom preferably has the (S)-configuration and the chain carbon atom carrying the hydroxy group preferably has the (R)-configuration and the double bond joined to the radical alk is preferably in the cis-configuration and the additional double bond which may be present is preferably in the trans-configuration, and to their salts, especially pharmaceutically acceptable salts.

The invention relates more especially to compounds of formula Ia in which $R_1$ is $C_1$-$C_4$alkyl, such as methyl, $R_2$ is $C_1$-$C_4$alkyl, such as propyl, X is oxy, alk is $C_2$-$C_5$alkylene, such as ethylene, 1,3-propylene or 1,4-butylene, n is 2, $R_3$ is phenyl substituted, especially in the meta-position, by $C_1$-$C_4$alkyl, such as methyl, trifluoromethyl or $C_1$-$C_4$-alkoxycarbonyl, such as methoxycarbonyl, or is $C_3$-$C_5$alkyl, such as propyl or butyl, ω,ω,ω-trifluoro-$C_3$-$C_5$alkyl, such as 3,3,3-trifluoropropyl or 4,4,4-trifluorobutyl, ω,ω,ω-1,ω-1-pentafluoro-$C_3$-$C_7$alkyl, such as 4,4,5,5,5-pentafluoropentyl, ω,ω,ω-Trifluor-ω-1,ω-1-dichloro-$C_4$-$C_6$alkyl, such as 4,4-dichloro-5,5,5-trifluoropentyl, or $C_1$-$C_4$alkoxycarbonyl-$C_2$-$C_4$alkyl, such as 3-methoxycarbonylpropyl or 4-methoxycarbonylbutyl, $R_4$ is carboxy, and $R_5$ is hydrogen, the chain carbon atom bonded to the sulfur atom preferably has the (S)-configuration and the chain carbon atom carrying the hydroxy group preferably has the (R)-configuration and the double bond joined to the radical alk is preferably in the cis-configuration and the other additional double bond is preferably in the trans-configuration, and to their salts, especially pharmaceutically acceptable salts.

The invention relates specifically to the compounds of formula I mentioned in the Examples and to their salts, especially pharmaceutically acceptable salts.

The process according to the invention for the preparation of compounds of formula I and their salts is based on methods known per se and is carried out as follows: an epoxide of formula

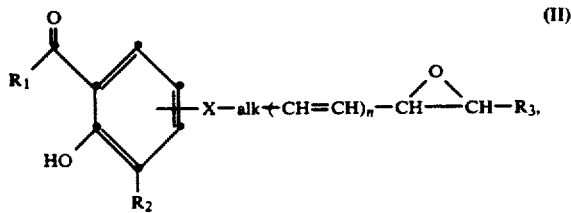

in which $R_1$, $R_2$, X, alk, n, A and $R_3$ are as defined above, is reacted with a thiol of formula

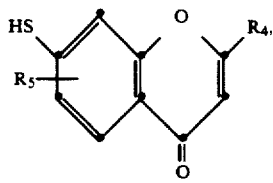

in which $R_4$ and $R_5$ are as defined above, or with a salt thereof, and, if desired, a compound obtainable in accordance with the process is converted into a different compound of formula I, a stereoisomeric mixture obtainable in accordance with the process is separated into the components and/or a free compound obtainable in accordance with the process is converted into a salt, or a salt obtainable in accordance with the process is converted into the free compound or into a different salt.

In the reaction of epoxides II with thiols III, the configuration at the carbon atom bonding with the thio group is reversed and the configuration at the carbon atom carrying the hydroxy group is retained. In order to obtain the preferred compounds having the opposite configuration at these two carbon atoms, it is therefore preferable to use the corresponding trans-epoxides II as starting materials. Starting from R,R-epoxides II there are obtained compounds I having the S(C—S—)—, R(C—OH)-configuration, and starting from S,S-epoxides II there are obtained compounds I having the R(C—S—), S(C—OH)-configuration. The reaction is effected under conditions known per se at a temperature of from approximately −20° C. to approximately +50° C., preferably at room temperature, that is to say from 18° C. to 25° C., and especially in a basic medium, for example in the presence of an amine, especially a tertiary aliphatic, arylaliphatic or saturated heterocyclic amine, such as a trialkylamine (for example triethylamine or ethyldiisopropylamine), a dialkylbenzylamine (for example N,N-dimethylbenzylamine), an N,N-dialkylaniline (for example N,N-dimethylaniline) or N-methyl- or N-ethyl-piperidine or N,N'-dimethylpiperazine. The reaction is usually carried out in an inert organic solvent, such as a lower alkanol, for example methanol or ethanol.

In a preferred form, components II and III in which $R_4$ is esterified carboxy or tetrazolyl and $R_3$ is as defined above and is, for example, esterified carboxy or unsubstituted or fluorinated lower alkyl are used as starting materials and $R_4$ is hydrolysed (optionally selectively) to carboxy, which is then converted, if desired, into amidated carboxy.

Starting materials for the process according to the invention are either known per se or can be obtained in a manner known per se by known analogy processes.

The epoxide of the above-defined formula II used as starting material can be prepared especially by means of the same processes as those used in the synthesis of leucotrienes, In a typical general method of synthesis for compounds II in which n is 1, for example, an aldehyde of formula $$O=CH-R_3 \quad (IV),$$

in which A and $R_3$ are as defined above, is used as starting material, a free carboxy group $R_3$ which may be present being protected in the form of an ester, for example a lower alkyl ester. This compound is condensed with formylmethylenetriphenylphosphorane (or an equivalent reagent), the corresponding trans-3-$R_3$-prop-2-enal of formula

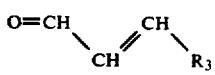 (V)

being formed. This compound is then epoxidised in a manner known per se, preferably under weakly alkaline conditions (for example in the presence of alkali metal carbonates), with aqueous hydrogen peroxide, to produce a trans-, that is to say 2(RS),3(RS)-epoxy-3-$R_3$ propanal of formula

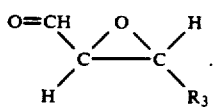 (VI)

The epoxyaldehyde VI can then be reacted to form the corresponding epoxide II in which $R_4$ is esterified carboxy and n is 1 by condensation with a phosphonium halide

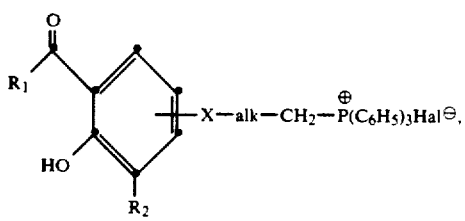 (VII)

in which $R_1$, $R_2$ and alk are as defined above and Hal is a halogen atom, preferably bromine, and with a base, for example sodium amide, in tetahydrofuran.

Compounds VII are prepared especially by reaction of a corresponding compound of formula

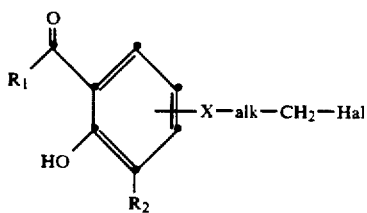 (VIII)

with triphenylphosphine in customary manner. Compounds VIII in which X is oxy or thio are obtained, for example, by condensing with one another corresponding compounds of formulae

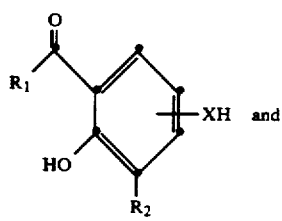 (IX)

Hal—alk—$CH_2$—Hal, (X)

in customary manner.

In another method of preparing compounds II, trans-3-$R_3$-prop-2-enol of formula

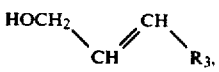 (XI)

in which $R_3$ is as defined above, but free carboxy as a substituent of $R_3$ is preferably in an ester form, is epoxidised, for example, by means of tert.-butyl hydroperoxide in the presence of titanium tetraisopropanolate and a D- or L-tartaric acid d-lower alkyl ester, and when a D-tartaric acid ester is used there is obtained predominantly 2R,3R-epoxy-3-$R_3$-propanol XIIa, and when an L-tartaric acid ester is used there is obtained predominantly the corresponding 2S,3S-epoxy-3-$R_3$-propanol XIIb

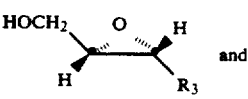 (XIIa)

and

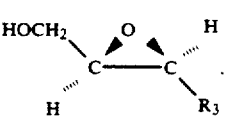 (XIIb)

This compound is then oxidised, for example by treatment with oxalyl chloride/dimethyl sulfoxide and then with triethylamine, to the corresponding epoxyaldehyde VI which can then be reacted with the corresponding phosphonium salt VII to form the corresponding epoxide II in which $R_3$ is esterified carboxy and n is 1.

In that reaction there are obtained predominantly epoxides II in which the double bond has the preferred cis-stereoconfiguration. If a D-tartaric acid ester is used, then, as mentioned above, there are obtained predominantly compounds II in which the epoxy group has the R,R-configuration, or S,S-enantiomers when the reaction is carried out in the presence of L-tartaric acid esters.

For the preparation of epoxides II in which n is 2, for example the epoxy alcohol XIIa or XIIb is first converted by treatment with N,N'-dicyclohexylcarbodiimide and dimethyl sulfoxide in the presence of trifluoroacetic acid and pyridine and then with triphenylphosphoranylideneacetaldehyde into the corresponding 4R,5R- or 4S,5S-4,5-epoxy-5-$R_3$-pent-2-enal of formula XIIIa or XIIIb, respectively

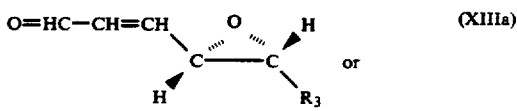 (XIIIa)

or

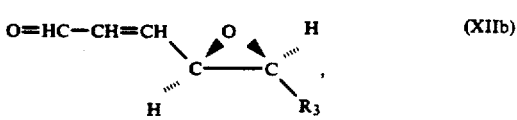 (XIIb)

which is then reacted further with the phosphonium halide VII to form the corresponding epoxide II in which n is 2. It is preferable to obtain those epoxides in which the double bond joined to the radical alk has cis-stereo-configuration and the double bond joined to the oxirane ring has trans-stereo-configuration.

Compounds obtainable in accordance with the process can, if desired, be converted into other compounds of formula I.

For example, esterified or amidated carboxy groups can be hydrolysed to free hydroxy, preferably under basic conditions, for example in the presence of sodium hydroxide solution, and preferably in a water-miscible organic solvent, such as tetrahydrofuran, dioxane or a lower alkanol, such as methanol or ethanol. Starting from compounds I in which $R_4$ is esterified carboxy, such as lower alkoxycarbonyl, and $R_3$ contains such a group as substituent, the hydrolysis can be controlled in such a manner that selectively only $R_4$ or both $R_4$ and the lower alkoxycarbonyl substituent of $R_3$ are hydrolysed to carboxy. If an equimolar sodium hydroxide solution is used and mild reaction conditions are chosen, for example stirring at room temperature for about 0.5 to 2 hours, virtually only alkoxycarbonyl $R_4$ is hydrolysed, whilst under extreme conditions, for example with prolonged reaction periods or with heating, both R. and the alkoxycarbonyl group in $R_3$ are hydrolysed to carboxy.

Conversely, carboxy $R_4$ and a carboxy substituent of $R_3$ can be esterified in customary manner.

Furthermore, free or esterified carboxy $R_4$ and such a group as a substituent of $R_3$ can be amidated in customary manner, for example by treatment with ammonia or with a mono- or di-lower alkylamine. For example, carboxy $R_4$ can be converted in customary manner, for example in the presence of a carbodiimide salt, for example N-ethyl-N'-(3-dimethylaminopropyl)-carbodiimide hydrochloride, and 4-dimethylaminopyridine, with an unsubstituted or substituted benzenesulfonamide into the corresponding N-benzenesulfamidoylcarbamoyl groups.

Of course, it is also possible to separate resulting diastereoisomeric mixtures into the individual components on the basis of the different physical properties of the components and/or to separate resulting mixtures of enantiomers into the individual enantiomers according to customary racemate separation processes.

If individual diastereoisomers are desired, then advantageously an individual diastereoisomer of a starting material can be used at any stage or one diastereoisomer can be formed preferentially from a starting material in diastereoisomer form by means of stereoselective reaction conditions or optically active reagents, or racemic diastereoisomeric mixtures can be separated into the individual diastereoisomers by physical separation methods, optionally using optically active auxiliaries.

From the stereochemical standpoint, however, both the condensation according to the invention of components II and III and the preparation of the starting materials are preferably carried out using starting materials that are uniform in stereo-configuration in each case, where possible carrying out the reactions stereoselectively, for example by the use of configuratively uniform, optically active reagents and/or auxiliaries, and isolating configuratively uniform products from reaction mixtures immediately after the reaction. For example, in the preparation of the unsaturated starting materials, cis- and trans-isomers which may be formed are separated from one another immediately, for which purpose the customary physical separation methods, such as, especially, chromatography, are suitable. In the main reaction there is used especially the stereoisomeric epoxide II having the stereoconfiguration of the double bond(s) that is preferred in the end product and in racemic form (which is often formed in the variant of the epoxidisation of the compound V with hydrogen peroxide) or preferably in the form of an individual diastereoisomer in which the configuration at the oxirane carbon atom making a bond with the S atom is opposite to the configuration at the (C—S—) carbon atom preferred in the end product I.

Likewise, resulting salts can be converted, for example by treatment with an acid, into the free acids, and resulting free acids can be converted by treatment with a base into salts.

As a result of the close relationship between the novel compounds in free form and in the form of their salts, hereinbefore and hereinafter the free compounds and their salts should be understood, where appropriate, as meaning also the corresponding salts and free compounds, respectively.

The invention relates also to those forms of the process according to which a compound obtainable as intermediate at any stage of the process is used as starting material and the remaining steps are carried out or a starting material is used in the form of a salt or is formed under the reaction conditions.

The invention relates also to the novel starting materials and intermediates occurring in the processes according to the invention and their preliminary stages.

Preferably, the starting materials used and the reaction conditions chosen are such that the compounds listed above as being especially preferred are obtained.

The present invention relates also to pharmaceutical preparations and medicaments that contain one of the compounds of formula I according to the invention or a pharmaceutically acceptable salt thereof. The pharmaceutical preparations according to the invention are especially those which are intended for local administration and especially for administration by inhalation, for example in the form of an aerosol, a micronised powder or a fine spray solution, to mammals, especially humans, and which contain the active ingredient on its own or together with a pharmaceutically acceptable carrier.

Pharmaceutical preparations for topical and local use are, for example, for the treatment of the skin, lotions and creams which contain a liquid or semi-solid oil-in-water or water-in-oil emulsion, and ointments (which preferably contain a preservative). Suitable for the treatment of the eyes are eye drops which contain the active ingredient in aqueous or oily solution, and eye ointments which are preferably manufactured in sterile form. Suitable for the treatment of the nose are aerosols and sprays (similar to those described below for the treatment of the respiratory tract), coarse powders which are administered by rapid inhalation through the nostrils, and especially nose drops which contain the active ingredient in aqueous or oily solution; suitable for local treatment of the buccal cavity are lozenges which contain the active ingredient in a mass generally formed of sugar and gum arabic or tragacanth, to which flavourings may be added, and pastilles which contain the active ingredient in an inert mass, for example of gelatine and glycerine or sugar and gum arabic.

Pharmaceutical preparations suitable for administration in the form of aerosols or sprays are, for example, solutions, suspensions or emulsions of the compound of formula I according to the invention with a suitable pharmaceutically acceptable solvent, such as, especially, ethanol and water, or a mixture of such solvents. They may, as necessary, contain other pharmaceutical adjuncts, such as non-ionic or anionic surface-active agents, emulsifiers and stabilisers, and also active ingredients of other kinds, and especially advantageously they can be mixed with a propellant gas, such as an inert gas under elevated pressure or especially with a readily volatile liquid, preferably a liquid that boils under normal atmospheric pressure below customary room temperature (for example from approximately −30° to +10° C.), such as an at least partially fluorinated polyhalogenated lower alkane, or a mixture of such liquids. Such pharmaceutical preparations, which are used predominantly as intermediates or stock mixtures for the preparation of the corresponding medicaments in finished form, contain the active ingredient customarily in a concentration of from approximately 0.1 to approximately 10% by weight, especially from approximately 0.3 to approximately 3% by weight. For the preparation of medicaments in finished form, such a pharmaceutical preparation is introduced into suitable containers, such as flacons and pressurised bottles, which are provided with a spray device or valve suitable for such purposes. The valve is preferably constructed in the form of a metering valve which on operation releases a predetermined amount of liquid, corresponding to a predetermined dose of the active ingredient. In the preparation of the finished medicament form, it is also possible for corresponding amounts of the pharmaceutical preparation in stock solution form and of the propellant to be introduced separately into the containers and to be mixed with one another only at that stage. The dosage of the compound of formula I to be administered and the frequency of administration depend upon the effectiveness and the duration of action of each individual compound, upon the severity of the disease to be treated and its symptoms, and upon the sex, age, weight and individual responsiveness of the mammal to be treated. On average, the recommended daily dose of a compound of formula I according to the invention for a mammal (especially a human) weighing 75 kg might be in the region of from approximately 10 to approximately 500 mg, preferably from approximately 25 to approximately 250 mg, which can advantageously be administered in several doses per day, as necessary.

The invention relates also to the use of the active ingredients of formula I according to the invention for alleviating or eliminating pathological conditions and/or symptoms of the body of a mammal, especially of a human, which can be attributed to the action of leucotrienes and occur especially in asthma. This use or the corresponding curative method comprises the treatment of the affected body or part of the body with an anti-allergically effective amount of a compound of formula I on its own or in the form of a medicament, especially a pharmaceutical preparation intended for inhalation. The expression "an anti-allergically effective amount" is to be understood as being that amount of the active ingredient which is sufficient to produce a significant inhibition of the contractions caused by leucotrienes.

The following Examples illustrate the present invention in more detail but do not limit the scope thereof. All temperatures are given in degrees Celsius.

EXAMPLE 1

(1R,2S)-1-hydroxy-1-(3-trifluoromethylphenyl)-8-(4-acetyl-3-hydroxy-2-propylphenoxy)-octa-3(E),5(Z)-dien-2-yl-7-thio-4-oxo-4H-1-benzopyrane-2-carboxylic acid methyl ester A solution of 0.93 g of (1R,2R)-1,2-epoxy-1-(3-trifluoromethylphenyl)-8-(4-acetyl-3-hydroxy-2-propylphenoxy)-octa-3(E),5(Z)-diene in 25 ml of methanol is stirred under argon with 0.80 g of triethylamine and 0.62 g of 7-mercaptochromone-2-carboxylic acid methyl ester for 20 hours at room temperature and concentrated by evaporation. The residue is dissolved in ethyl acetate and filtered over silica gel. The filtrate is washed once with 2N hydrochloric acid and 3 times with brine, dried over magnesium sulfate and concentrated by evaporation. Purification of the residue by chromatography on silica gel with hexane/ethyl acetate (1:1) yields the title compound having a melting point of 62°–63°; $[\alpha]_D^{20}$ (methanol, 0.135%)=103°±7.4°; UV (methanol): $\lambda_{max}(\epsilon)$=216 (50,000), 235/sh, 271 (27,940), 285/sh; 325 (12900).

The starting material is prepared, for example, as follows:

a) (2R,3R)-2,3-epoxy-3-(3-trifluoromethylphenyl)-propanol

Under totally anhydrous conditions and an argon atmosphere, a solution of 4.62 ml of tetraisopropyl orthotitanate in 100 ml of methylene chloride is cooled to −70°, and 3.2 ml of D(−)-tartaric acid diethyl ester and 5.45 g of 3-(3-trifluoromethylphenyl)-prop-2(E)-enol in a small amount of methylene chloride are added. After stirring for 10 minutes at −70°, 21.5 ml of 3-molar tert.-butyl hydroperoxide solution in toluene are added, the temperature rising to −60° C. The temperature is allowed to rise to 0° within a period of 2 hours, and the resulting yellow solution is poured slowly into a solution of 14.5 g of iron(II) sulfate and 5.8 g of L(+)-tartaric acid in 60 ml of water (cooling!, exothermic) and the mixture is stirred for 30 minutes at 5°–10°. The aqueous phase is separated off and extracted with ether. The combined organic extracts are dried over sodium sulfate and concentrated by evaporation. The residue is dissolved in 90 ml of ether, cooled to 0°–5°, and a suspension of 2.32 g of sodium hydroxide in 60 ml of brine is added and the mixture is stirred for 1 hour at 0°–5°. The aqueous phase Is separated off and extracted with ether. The combined ether phases are dried over sodium sulfate and concentrated by evaporation. The residue is purified by chromatography on silica gel with hexane/ethyl acetate (3:2). The title compound is thus obtained in the form of a colourless oil;

IR (CH$_2$Cl$_2$): 3550, 3430, 2950, 2880, 2830, 1310, 1150, 1110, 1050 cm$^{-1}$; $[\alpha]_D^{20}$ (methanol, 0.175%)=42.3°±5.7°; R$_f$=0.30 (hexane/ethyl acetate 3:2).

b) (4R,5R)-4,5-epoxy-5-(3-trifluoromethylphenyl)-pent-2(E)-enal

A solution of 4.5 g of (2R,3R)-2,3-epoxy-3-(3-trifluoromethylphenyl)-propanol in 105 ml of dimethyl sulfoxide is stirred under argon with 1.7 ml of pyridine, 0.77 ml of trifluoroacetic acid and 12.75 g of N,N-dicyclohexylcarbodiimide for 6 hours at room temperature.

After the addition of 8.25 g of formylmethylenetriphenylphosphorane, stirring is continued for a further 20 hours at room temperature; 320 ml of ethyl acetate are added and after 10 minutes the mixture is poured onto 320 ml of brine. The resulting suspension is stirred for 5 minutes and filtered. In the filtrate the aqueous phase is extracted twice with ethyl acetate. The combined organic phases are washed 3 times with brine, dried over sodium sulfate and concentrated by evaporation. The residue is filtered over silica gel with ether/hexane = (4:1). The filtrate is concentrated by evaporation and the residue is purified by chromatography on silica gel with hexane/ethyl acetate (3:1). The title compound is thus obtained in the form of a light-yellow oil;

IR ($CH_2Cl_2$): 2780, 2695, 1670, 1620, 1305, 1145, 1105 $cm^{-1}$; $R_f$=0.31 (hexane/ethyl acetate 3:1) $[\alpha]_D^{20}$ (chloroform, 0.245%)=144.5°±4.1°.

c)
3-(4-acetyl-3-hydroxy-2-propylphenoxy)-propyl-triphenylphosphonium bromide A solution of 27 g of 3-(4-acetyl-3-hydroxy-2-propylphenoxy)-propyl bromide in 50 ml of toluene is heated at reflux with 21.85 g of triphenylphosphine for 20 hours. The resulting suspension is cooled to room temperature; 200 ml of ether are added and the mixture is stirred for 1 hour. The colourless precipitate is filtered off with suction, washed with ether and dried. The title compound has a melting point of 211°-212°.

d)
(1R,2R)-1,2-epoxy-1-(3-trifluoromethylphenyl)-8-(4-acetyl-3-hydroxy-2-propylphenoxy)-octa-3(E),5(Z)-diene A suspension of 5.55 g of 3-(4-acetyl-3-hydroxy-2-propylphenoxy)propyl-triphenylphosphonium bromide in 80 ml of tetrahydrofuran is stirred under argon with 0.78 g of $NaNH_2$ and 60 mg of potassium tert.-butanolate for 1 hour at room temperature, then cooled to 0°-5°, 1.7 g of (4R,5R)-4,5-epoxy-5-(3-trifluoromethylphenyl)-pent-2(E)-enal in 20 ml of tetrahydrofuran are added within a period of 5 minutes and the mixture is then stirred for 2 hours at room temperature. The resulting suspension is poured onto phosphate buffer (pH 7) and extracted with ether. The combined ether extracts are washed with phosphate buffer pH 7, dried over sodium sulfate and concentrated by evaporation. The residue is taken up in hexane/ethyl acetate/triethylamine (24:71:5) and filtered over silica gel that has been prewashed with that solvent mixture. The filtrate is concentrated by evaporation and yields the title compound in the form of a light-yellow oil; $R_f$=0.75 (hexane/ethyl acetate 3:2).

EXAMPLE 2

Sodium salt of (1R,2S)-1-hydroxy-1-(3-trifluoromethylphenyl)-8-(4-acetyl-3-hydroxy-2-propylphenoxy)-octa-3(E),5(Z)-dien-2-yl-7-thio-4-oxo-4H-1-benzopyrane-2-carboxylic acid 0.7 g of (1R,2S)-1-hydroxy-1-(3-trifluoromethylphenyl)-8-(4-acetyl-3-hydroxy-2-propylphenoxy)-octa-3(E),5(Z)-dien-2-yl-7-thio-4-oxo-4H-1-benzopyrane-2-carboxylic acid methyl ester is dissolved under argon in 20 ml of tetrahydrofuran; 5.1 ml of 0.2N sodium hydroxide solution are added and the mixture is stirred for 1 hour at room temperature. Concentration by evaporation and purification of the residue by chromatography on a "Reversed Phase" silica gel column (for example Merck Lichroprep ® RP-8) with methanol/water (3:1) yield the title compound, m.p. 207°-209°, $[\alpha]_D^{20}$(0.54%, methanol)=96.3°±1.9° UV (methanol): $\lambda_{max}$ ($\epsilon$)=220 (488840), 235/sh, 267 (25940), 285 (22900), 324/sh.

EXAMPLE 3

(1S,2R)-1-hydroxy-1-(3-trifluoromethylphenyl)-8-(4-acetyl-3-hydroxy-2-propylphenoxy)-octa-3(E),5(Z)-dien-2-yl-7-thio-4-oxo-4H-1-benzopyrane-2-carboxylic acid methyl ester The title compound is prepared analogously to Example 1 from (1S,2S)-1,2-epoxy-1-(3-trifluoromethylphenyl)-8-(4-acetyl-3-hydroxy-2-propylphenoxy)-octa-3(E),5(Z)-diene; m.p. 68°-69°.

The starting material is prepared, for example, as follows:

a)
(2S,3S)-2,3-epoxy-3-(3-trifluoromethylphenyl)-propanol

The title compound is prepared as described in Example 1a) but using L(+)-tartaric acid diethyl ester; colourless oil; IR (CH2C12): 3590, 3480, 2920, 2870, 1330, 1165, 1125, 1070 $cm^{-1}$; $[\alpha]_D^{20}$ (methanol, 0.175%)= −41.7°±5.7°; $R_f$=0.34 (hexane/ethyl acetate 1:1).

b)
(4S,5S)-4,5-epoxy-5-(3-trifluoromethylphenyl)-pent-2(E)-enal

The title compound is prepared analogously to Example 1b) from the epoxy alcohol according to a); light-yellow oil; IR ($CH_2Cl_2$): 2780, 2695, 1670, 1620, 1305, 1145, 1110 $cm^{-1}$; $[\alpha]_D^{20}$ (chloroform, 0.15%)= −158.0°±6.7°; $R_f$=0.4 (hexane/ethyl acetate 4:1).

c)
(1S,2S)-1,2-epoxy-1-(3-trifluoromethylphenyl)-8-(4-acetyl-3-hydroxy-2-propylphenoxy)-octa-3(E),5(Z)-diene The title compound is prepared analogously to Example 1d) from the epoxyaldehyde according to b); light-brown oil; $R_f$=0.61 (hexane/ethyl acetate 3:2).

EXAMPLE 4

Sodium salt of (1S,2R)-1-hydroxy-1-(3-trifluoromethylphenyl)-8-(4-acetyl-3-hydroxy-2-propylphenoxy)-octa-3(E),5(Z)-dien-2-yl-7-thio-4-oxo-4H-1-benzopyrane-2-carboxylic acid The title compound is prepared analogously to Example 2 from the corresponding methyl ester according to Example 3; m.p. 210°-212°, $[\alpha]_D^{20}$ (MeOH, 0.18%)= −86.1°±5.6° UV (MeOH): $\lambda_{max}(\epsilon)$=220 (42820); 235/sh; 267 (26660); 285 (23760); 320 (15800).

EXAMPLE 5

(1R,2S)-1-hydroxy-1-(3-trifluoromethylphenyl)-6-(4-acetyl-3-hydroxy-2-propylphenoxy)-hex-3(Z)-en-2-yl-7-thio-4-oxo-4H-1-benzopyranecarboxylic acid methyl ester The title compound is prepared analogously to Example 1 from (1R,2R)-1,2-epoxy-1-(3-trifluoromethylphenyl)-6-(4-acetyl-3-hydroxy-2-propylphenoxy)-hex- 3(Z)-ene; light-yellow viscous oil; $[\alpha]_D^{20}$ (MeOH, 0.115%) = 57.4°±8.7°; UV (MeOH): $\lambda_{max}(\epsilon)$ = 220/sh; 271 (5280); 285/sh; 320 (2800).

The starting material is prepared, for example, as follows:

a)
(2S,3R)-2,3-epoxy-3-(3-trifluoromethylphenyl)-propanal

A solution of 1.1 g of oxalyl chloride in 15 ml of methylene chloride is cooled to −65°-70° under argon and within a period of 2 minutes 1.5 g of dimethyl sulfoxide in 5 ml of methylene dichloride are added. After stirring for 10 minutes at −65°-70°, 1.7 g of (2R,3R)-2,3-epoxy-3-(3-trifluoromethylphenyl)-propanol in 15 ml of methylene chloride are added dropwise. After stirring for a further 30 minutes, 4 g of triethylamine are added dropwise, the temperature rising to −40°. The temperature is allowed to rise to 0° and the reaction mixture is poured onto phosphate buffer (pH 8). The organic phase is separated off and the aqueous phase is extracted with methylene chloride. The combined organic extracts are washed twice with brine, dried over sodium sulfate and concentrated by evaporation. Chromatography of the residue on silica gel with hexane/ethyl acetate (7:3) yields the title compound in the form of a colourless oil; IR (methylene chloride): 2820, 1730, 1330, 1165, 1125, 1070 cm$^{-1}$. $R_f$=0.36 (hexane/ethyl acetate 3:2). $[\alpha]_D^{20}$ (chloroform, 0.20%) = −17.5°±5°.

b)
(1R,2R)-1,2-epoxy-1-(3-trifluoromethylphenyl)-6-(4-acetyl-3-hydroxy-2-propylphenoxy)-hex-3(Z)-ene The title compound is prepared analogously to Example 1d) from the epoxyaldehyde according to a); light-yellow oil; $R_f$=0.69 (hexane/ethyl acetate 3:2).

EXAMPLE 6

Sodium salt of (1R,2S)-1-hydroxy-1-(3-trifluoromethylphenyl)-6-(4-acetyl-3-hydroxy-2-propylphenoxy)-hex-3(Z)-en-2-yl-7-thio-4-oxo-4H-1-benzopyrane-2-carboxylic acid The title compound is prepared analogously to Example 2 from the corresponding methyl ester according to Example 5; m.p. 222°-224°; $[\alpha]_D^{20}$ (MeOH, 0.135%)=62.2°±7.4°. UV (MeOH): $\lambda_{max}(\epsilon)$=267 (22060); 285 (21140); 318/sh.

EXAMPLE 7

(1S,2R)-1-hydroxy-1-(3-trifluoromethylphenyl)-6-(4-acetyl-3-hydroxy-2-propylphenoxy)-hex-3(Z)-en-2-yl-7-thio-4-oxo-4H-1-benzopyranecarboxylic acid methyl ester The title compound is prepared analogously to Example 1 from (1S,2S)-1,2-epoxy-1-(3-trifluoromethylphenyl)-6-(4-acetyl-3-hydroxy-2-propylphenoxy)-hex-3(Z)-ene; colourless powder having a melting point of 69°-71°.

The starting material is prepared, for example, as follows:

a)
(2R,3S)-2,3-epoxy-3-(3-trifluoromethylphenyl)-propanal

The title compound is prepared analogously to Example 5a) from (2S,3S)-2,3-epoxy-3-(3-trifluoromethylphenyl)-propanol. Light-yellow liquid; IR (CH$_2$Cl$_2$): 2820, 1730, 1330, 1165, 1130, 1070 cm$^{-1}$; $[\alpha]_D^{20}$ (chloroform, 0.20%)=0.0°±5°; $[\alpha]_{365}^{20}$ (chloroform, 0.20%)=475.0°±5.0°; $R_f$=0.44 (hexane/ethyl acetate 7:3).

b)
(1S,2S)-1,2-epoxy-1-(3-trifluoromethylphenyl)-6-(4-acetyl-3-hydroxy-2-propylphenoxy)-hex-3(Z)-ene The title compound is prepared analogously to Example 1d) from the corresponding epoxyaldehyde according to a). Light-yellow oil; $R_f$=0.43 (hexane/ethyl acetate 3:2).

EXAMPLE 8

Sodium salt of (1S,2R)-1-hydroxy-1-(3-trifluoromethylphenyl)-6-(4-acetyl-3-hydroxy-2-propylphenoxy)-hex-3(Z)-en-2-yl-7-thio-4-oxo-4H-1-benzopyrane-2-carboxylic acid The title compound is prepared analogously to Example 2 from the corresponding methyl ester according to Example 7; m.p. 239°-241°; $[\alpha]_D^{20}$ (methanol, 0.15%)=−60.7°±6.7°; UV (methanol): $\lambda_{max}(\epsilon)$=216 (44080); 268 (22520); 285 (21640); 320/sh.

EXAMPLE 9

(1R,2S)-1-hydroxy-1-(3-methylphenyl)-8-(4-acetyl-3-hydroxy-2-propylphenoxy)-octa-3(E),5(Z)-dien-2-yl-7-thio-4-oxo-4H-1-benzopyrane-2-carboxylic acid methyl ester The title compound is prepared analogously to Example 1 from (1R,2R)-1,2-epoxy-1-(3-methylphenyl)-8-(4-acetyl-3-hydroxy-2-propylphenoxy)-octa-3(E),5(Z)-diene; light-yellow powder having a melting point of 71°-72°; $[\alpha]_D^{20}$=81.7°±8.7° (MeOH, 0.115%); UV (MeOH): $\lambda_{max}(\epsilon)$=217 (53680); 235/sh; 271 (29120); 285/sh; 325 (13200).

The starting material is prepared, for example, as follows:

a) (2R,3R)-2,3-epoxy-3-(3-methylphenyl)-propanol

The title compound is prepared analogously to Example 1a) from 3-(3-methylphenyl)-prop-2(E)-enol; colourless, viscous oil; IR (CH$_2$Cl$_2$): 3560, 3410, 2880, 2830, 1590, 1050 cm$^{-1}$; $R_f$=0.39 (hexane/ethyl acetate 1:1); $[\alpha]_D^{20}$=38.9°±5.3° (chloroform, 0.19%).

b)
(4R,5R)-4,5-epoxy-5-(3-methylphenyl)-pent-2(E)-enal

The title compound is prepared analogously to Example 1b) from the epoxy alcohol according to a); light-yellow powder, m.p. 60°-61°; IR (CH$_2$Cl$_2$): 2920, 2820, 2740, 1690, 1640, 1610, 1155, 1130 cm$^{-1}$; $R_f$=0.34 (hexane/ethyl acetate 4:1).

c)
(1R,2R)-1,2-epoxy-1-(3-methylphenyl)-8-(4-acetyl-3-hydroxy-2-propylphenoxy)-octa-3(E),5(Z)-diene The title compound is prepared analogously to Example 1d) from the corresponding epoxyaldehyde according to a); light-yellow oil; $R_f$=0.63 (hexane/ethyl acetate 3:2).

EXAMPLE 10

Sodium salt of (1R,2S)-1-hydroxy-1-(3-methylphenyl)-8-(4-acetyl-3-hydroxy-2-propylphenoxy)-octa-3(E),5(Z)-dien-2-yl-7-thio-4-oxo-4H-1-benzopyrane-2-carboxylic acid The title compound is prepared analogously to Example 2 from the corresponding methyl ester according to Example 9; beige powder having a melting point of 217° (decomp.); $[\alpha]_D^{20}$ (methanol, 0.15%)=71.3°±6.7°; UV (methanol): $\lambda_{max}(\epsilon)$=219 (51520); 234/sh; 267 (26460); 284 (23280); 322/sh.

EXAMPLE 11

(1S,2R)-1-hydroxy-1-(3-methylphenyl)-8-(4-acetyl-3-hydroxy-2-propylphenoxy)-octa-3(E),5(Z)-dien-2-yl-7-thio-4-oxo-4H-1-benzopyrane-2-carboxylic acid methyl ester The title compound is prepared analogously to Example 1 from (1S,2S)-1,2-epoxy-1-(m-tolyl)-8-(4-acetyl-3-hydroxy-2-propylphenoxy)-octa-3(E),5(Z)-diene; $[\alpha]_D^{20}$ (MeOH, 0.148%)= −75.7°±6.8°; UV (MeOH): $\lambda_{max}(\epsilon)$=217 (51760); 240/sh; 271 (27860); 290/sh; 328 (12600).

The starting material is prepared, for example, as follows:

a) (2S,3S)-2,3-epoxy-3-(3-methylphenyl)-propanol

The title compound is prepared analogously to Example 1a) from 3-(3-methylphenyl)-prop-2(E)-enol but using L(+)-tartaric acid diethyl ester; colourless oil; IR (CH$_2$Cl$_2$): 3550, 3470, 2940, 2880, 2830, 1590, 1050 cm$^{-1}$; R$_f$=0.31 (hexane/ethyl acetate 3:2).

b) (4S,5S)-4,5-epoxy-5-(3-methylphenyl)-pent-2(E)-enal

The title compound is prepared analogously to Example 1b) from the epoxy alcohol according to a); light-yellow oil; IR (CH$_2$Cl$_2$): 2920, 2820, 2740, 1690, 1640, 1610, 1155, 1130, 1085 cm$^{-1}$; R$_f$=0.29 (hexane/ethyl acetate 4:1).

c) (1S,2S)-1,2-epoxy-1-(3-methylphenyl)-8-(4-acetyl-3-hydroxy-2-propylphenoxy)-octa-3(E),5(Z)-diene The title compound is prepared analogously to Example 1d) from the epoxyaldehyde according to b); light-yellow oil; R$_f$=0.51 (hexane/ethyl acetate 7:3).

EXAMPLE 12

Sodium salt of (1S,2R)-1-hydroxy-1-(3-methylphenyl)-8-(4-acetyl-3-hydroxy-2-propylphenoxy)-octa-3(E),5(Z)-dien-2-yl-7-thio-4-oxo-4H-1-benzopyrane-2-carboxylic acid The title compound is prepared analogously to Example 1 from the corresponding methyl ester according to Example 11; m.p. 197°-198°; $[\alpha]_D^{20}$ (0.14%, methanol)= −72.1°±7.1°; UV (MeOH): $\lambda_{max}(\epsilon)$=218 (50700); 235/sh; 267 (25780); 285 (22600); 321 (15000).

EXAMPLE 13

(1R,2S)-1-hydroxy-1-(3-methylphenyl)-6-(4-acetyl-3-hydroxy-2-propylphenoxy)-hex-3(Z)-en-2-yl-7-thio-4-oxo-4H-1-benzopyrane-2-carboxylic acid methyl ester The title compound is prepared analogously to Example 1 from (1R,2R)-1,2-epoxy-1-(3-tolyl)-6-(4-acetyl-3-hydroxy-2-propylphenoxy)-hex-3(Z)-ene; colourless powder having a melting point of 136 138°; $[\alpha]_D^{20}$=28.1°±7.4° (methanol, 0.135%); UV (methanol): $\lambda_{max}(\epsilon)$=271 (26020); 282/sh; 323 (13700).

The starting material is prepared, for example, as follows:

a) (2S,3R)-2,3-epoxy-3-(3-methylphenyl)-propanal

The title compound is prepared analogously to Example 5a) from (2R,3R)-2,3-epoxy-3-(3-methylphenyl)-propanol; light-yellow oil. IR (methylene chloride): 2920, 2820, 1730, 1610, 1140, 1070 cm$^{-1}$; R$_f$=0.49 (hexane/ethyl acetate 3:2).

b) (1R,2R)-1,2-epoxy-1-(3-methylphenyl)-6-(4-acetyl-3-hydroxy-2-propylphenoxy)-hex-3(Z)-ene The title compound is prepared analogously to Example 1d) from the corresponding epoxyaldehyde according to a); light-yellow oil; R$_f$=0.73 (hexane/ethyl acetate 3:2).

EXAMPLE 14

Sodium salt of (1R,2S)-1-hydroxy-1-(3-methylphenyl)-6-(4-acetyl-3-hydroxy-2-propylphenoxy)-hex-3(Z)-en-2-yl-7-thio-4-oxo-4H-1-benzopyrane-2-carboxylic acid The title compound is prepared analogously to Example 2 from the corresponding methyl ester according to Example 13; beige powder having a melting point of 238°-240°; $[\alpha]_D^{20}$ (methanol 0.135%)=31.1°±7.4°; UV (methanol): $\lambda_{max}(\epsilon)$=268 (21800); 285 (20860); 322/sh.

EXAMPLE 15

(1R,2S)-1-hydroxy-1-(3-methoxycarbonylphenyl)-8-(4-acetyl-3-hydroxy-2-propylphenoxy)-octa-3(E),5(Z)-dien-2-yl-7-thio-4-oxo-4H-1-benzopyrane-2-carboxylic acid methyl ester The title compound is prepared analogously to Example 1 from (1R,2R)-1,2-epoxy-1-(3-methoxycarbonylphenyl)-8-(4-acetyl-3-hydroxy-2-propylphenoxy)-octa-3(E),5(Z)-diene; $[\alpha]_D^{20}$ (methanol, 0.14%)=27.9°±7.1°; UV (methanol): $\lambda_{max}(\epsilon)$=221 (53560); 234/sh; 270 (28980); 285/sh; 326 (13860).

The starting material is prepared, for example, as follows:

a) (2R,3R)-2,3-epoxy-3-(3-methoxycarbonylphenyl)-propanol

The title compound is prepared analogously to Example 1a) from (E)-3-methoxycarbonylcinnamic alcohol; slightly yellowish oil; R$_f$=0.3 (hexane/ethyl acetate 1:1).

b) (4R,5R)-4,5-epoxy-5-(3-methoxycarbonylphenyl)-pent-2(E)-enal

The title compound is prepared analogously to Example 1b) from the corresponding epoxy alcohol; light-yellow oil; R$_f$=0.35 (hexane/ethyl acetate 3:2).

c) (1R,2R)-1,2-epoxy-(3-methoxycarbonylphenyl)-8-(4-acetyl-3-hydroxy-2-propylphenoxy)-octa-3(E),5(Z)-diene The title compound is prepared analogously to Example 1d) from the corresponding epoxyaldehyde according to b); viscous yellow oil; $R_f = 0.50$ (hexane/ethyl acetate 3:2).

EXAMPLE 16

Sodium salt of (1R,2S)-1-hydroxy-1-(3-methoxycarbonylphenyl)-8-(4-acetyl-3-hydroxy-2-propylphenoxy)-octa-3(E),5(Z)-dien-2-yl-7-thio-4-oxo-4H-1-benzopyrane-2-carboxylic acid The title compound is prepared analogously to Example 2 from (1R,2S)-1-hydroxy-1-(3-methoxycarbonylphenyl)-8-(4-acetyl-3-hydroxy-2-propylphenoxy)-octa-3(E),5(Z)-dien-2-yl-7-thio-4-oxo-4H-1-benzopyrane-2-carboxylic acid methyl ester according to Example 15; light-brown powder having a melting point of 181° (decomp.); $[\alpha]_D^{20}$ (methanol, 0.15%) = 32.0°±6.7°; UV (methanol): $\lambda_{max}(\epsilon) = 222$ (51600); 232/sh; 267 (24160); 284 (22940); 320/sh; 400/sh.

EXAMPLE 17

(1S,2R)-1-hydroxy-1-(3-methoxycarbonylphenyl)-8-(4-acetyl-3-hydroxy-2-propylphenoxy)-octa-3(E),5(Z)-dien-2-yl-7-thio-4-oxo-4H-1-benzopyrane-2-carboxylic acid methyl ester The title compound is prepared analogously to Example 1 from the (1S,2S)-1,2-epoxy-1-(3-methoxycarbonylphenyl)-8-(4-acetyl-3-hydroxy-2-propylphenoxy)-octa-3(E),5(Z)-diene; m.p. 77°–78° (colourless powder); $[\alpha]_D^{20}$ (methanol, 0.15%) = −52.7°±6.7°; UV (methanol): $\lambda_{max}(\epsilon) = 221$ (57420); 235/sh; 271 (29980); 288/sh; 326 (14320).

The starting material is prepared, for example, as follows:

a)
(2S,3S)-2,3-epoxy-3-(3-methoxycarbonylphenyl)-propanol

The title compound is prepared analogously to Example 1a) from (E)-3-methoxycarbonylcinnamic alcohol but using L(+)-tartaric acid diethyl ester; colourless oil; $R_f = 0.48$ (hexane/ethyl acetate 1:1).

b)
(4S,5S)-4,5-epoxy-5-(3-methoxycarbonylphenyl)-pent-2-(E)-enal

The title compound is prepared analogously to Example 1b) from the corresponding epoxy alcohol; colourless oil; IR (methylene chloride): 3050, 2990, 2945, 2820, 2730, 1725, 1695, 1640, 1290, 1255 cm$^{-1}$; $R_f = 0.34$ (hexane/ethyl acetate 3:2).

c)
(1S,2S)-1,2-epoxy-1-(3-methoxycarbonylphenyl)-8-(4-acetyl-3-hydroxy-2-propylphenoxy)-octa-3(E),5(Z)-diene The title compound is prepared analogously to Example 1d) from the corresponding epoxyaldehyde according to b); light-yellow oil; $R_f = 0.54$ (hexane/ethyl acetate 3:2).

EXAMPLE 18

Sodium salt of (1S,2R)-1-hydroxy-1-(3-methoxycarbonylphenyl)-8-(4-acetyl-3-hydroxy-2-propylphenoxy)-octa-3(E),5(Z)-dien-2-yl-7-thio-4-oxo-4H-1-benzopyrane-2-carboxylic acid The title compound is prepared analogously to Example 2 from the corresponding methyl ester according to Example 17; beige powder having a melting point of 174°–176°; $[\alpha]_D^{20}$ (methanol, 0.155%) = −80.6°±6.5°; UV (methanol): $\lambda_{max}(\epsilon) = 223$ (59300); 235 sh; 267 (27300); 284 (24800); 321 (16200).

EXAMPLE 19

(1R,2S)-1-hydroxy-1-(3-methoxycarbonylphenyl)-6-(4-acetyl-3-hydroxy-2-propylphenoxy)-hex-3(Z)-en-2-yl-7-thio-4-oxo-4H-1-benzopyrane-2-carboxylic acid methyl ester The title compound is prepared analogously to Example 1 from (1R,2R)-1,2-epoxy-1-(3-methoxycarbonylphenyl)-6-(4-acetyl-3-hydroxy-2-propylphenoxy)-hex-3(Z)-ene; colourless oil; $[\alpha]_D^{20}$ (methanol, 0.11%) = 24.5°±9.1°; UV (methanol): $\lambda_{max}(\epsilon) = 270$ (22400); 322 (12000).

The starting material is prepared, for example, as follows:

a)
(2S,3R)-2,3-epoxy-3-(3-methoxycarbonylphenyl)-propanal

The title compound is prepared analogously to Example 5a) from (2R,3R)-2,3-epoxy-3-(3-methoxycarbonylphenyl)-propanol; light-yellow oil; IR (methylene chloride): 2950, 2820, 1725, 1610, 1590, 1430, 1290, 1255 cm$^{-1}$; $R_f = 0.33$ (hexane/ethyl acetate 3:2).

b)
(1R,2R)-1,2-epoxy-1-(3-methoxycarbonylphenyl)-6-(4-acetyl-3-hydroxy-2-propylphenoxy)-hex-3(Z)-ene The title compound is prepared analogously to Example 1d) from the epoxyaldehyde according to a); light-yellow oil; $R_f = 0.39$ (hexane/ethyl acetate 3:2).

EXAMPLE 20

Sodium salt of (1R,2S)-1-hydroxy-1-(3-methoxycarbonylphenyl)-6-(4-acetyl-3-hydroxy-2-propylphenoxy)-hex-3(Z)-en-2-yl-7-thio-4-oxo-4H-1-benzopyrane-2-carboxylic acid (A), and disodium salt of (1R,2S)-1-hydroxy-1-(3-carboxyphenyl)-6-(4-acetyl-3-hydroxy-2-propylphenoxy)-hex-3(Z)-en-2-yl-7-thio-4-oxo-4H-1-benzopyrane-2-carboxylic acid (B)

A solution of 0.5 g of (1R,2S)-1-hydroxy-1-(3-methoxycarbonylphenyl)-6-(4-acetyl-3-hydroxy-2-propylphenoxy)-hex-3(Z)-en-2-yl-7-thio-4-oxo-4H-1-benzopyrane-2-carboxylic acid methyl ester according to Example 19 in 20 ml of tetrahydrofuran is stirred under argon for 40 hours with 7.5 ml of 0.2N sodium hydroxide solution at room temperature and is then concentrated by evaporation. The residue is purified by chromatography on Lichroprep ® RP-8, Merck, with methanol/water (3:1) and yields in fractions 2–5 title compound B; m.p. 262°–264°; $[\alpha]_D^{20}$ (methanol, 0.105%) = 17.1°±9.5°; UV (methanol): $\lambda_{max}(\epsilon) = 268$ (19680); 284 (19060); 325/sh; and in fractions 8–12 title compound A; m.p. 155° (decomp.); $[\alpha]_D^{20}$ (methanol, 0.12%) = 22.5°±8.3°; UV (methanol): $\lambda_{max}(\epsilon) = 268$ (26200); 286 (29220); 325/sh.

EXAMPLE 21

(1S,2R)-1-hydroxy-1-(3-methoxycarbonylphenyl)-6-(4-acetyl-3-hydroxy-2-propylphenoxy)-hex-3(Z)-en-2-yl-7-thio-4-oxo-4H-1-benzopyrane-2-carboxylic acid methyl ester The title compound is prepared analogously to Example 1 from (1S,2S)-1,2-epoxy-1-(3-carboxymethyl-phenyl)-6-(4-acetyl-3-hydroxy-2-propylphenoxy)-hex-3(Z)-ene; colourless oil which hardens in the refrigerator, m.p. 90°-91°; $[\alpha]_D^{20} = -41.5° \pm 7.7°$ (0.13% methanol); UV (methanol): $\lambda_{max}(\epsilon) = 271$ (25120); 322 (13280).

The starting material is prepared, for example, as follows:

a) (2R,3S)-2,3-epoxy-3-(3-methoxycarbonylphenyl)-propanal

The title compound is prepared analogously to Example 5 from (2S,3S)-2,3-epoxy-3-(3-methoxycarbonyl-phenyl)-propanol; colourless oil; IR (methylene chloride): 2910, 2780, 1705, 1590, 1570, 1415, 1270, 1235 cm$^{-1}$; R$_f$=0.36 (hexane/ethyl acetate 3:2).

b) (1S,2S)-1,2-epoxy-1-(3-methoxycarbonylphenyl)-6-(4-acetyl-3-hydroxy-2-propylphenoxy)-hex-3(Z)-ene The title compound is prepared analogously to Example 1d) from the corresponding epoxyaldehyde according to a); colourless oil, not characterised in more detail.

EXAMPLE 22

Sodium salt of (1S,2R)-1-hydroxy-1-(3-methoxycarbonylphenyl)-6-(4-acetyl-3-hydroxy-2-propylphenoxy-hex-3(Z)-en-2-yl-7-thio-4-oxo-4H-1-benzopyrane-2-carboxylic acid The title compound is prepared analogously to Example 2 from the corresponding methyl ester according to Example 21; beige powder having a melting point of 208°-210°; $[\alpha]_D^{20}$ (methanol, 0.12%) = $-41.7° \pm 8.3°$; UV (methanol): $\lambda_{max}(\epsilon) = 268$ (21060); 285 (21540); 325/sh.

EXAMPLE 23

(4R,5S)-1,1,1-trifluoro-4-hydroxy-11-(4-acetyl-3-hydroxy-2-propylphenoxy)-undeca6(E),8(Z)-dien-5-yl-7-thio-4-oxo-4H-1-benzopyrane-2-carboxylic acid methyl ester The title compound is prepared analogously to Example 1 from (4R,5R)-4,5-epoxy-1,1,1-trifluoro-11-(4-acetyl-3-hydroxy-2-propylphenoxy)-undeca-6(E),8(Z)-diene; beige powder having a melting point of 64°-66°, $[\alpha]_D^{20}$ (methanol, 0.15%) = 147.3°±6.7°. UV (methanol): $\lambda_{max}(\epsilon) = 220$ (48960); 270 (28500); 283/sh; 325 (13400).

The starting material is prepared, for example, as follows:

a) (2R,3R)-2,3-epoxy-6,6,6-trifluoro-hexanol

The title compound is prepared analogously to Example 1a) from 6,6,6-trifluoro-hex-2(E)-enol; colourless oil; $[\alpha]_D^{20}$ (chloroform, 0.17%) = 35.9°±5.9°; IR (methylene chloride): 3550, 3420, 2950, 2890, 2830, 1125 cm$^{-1}$.

b) (4R,5R)-4,5-epoxy-8,8,8-trifluoro-oct-2(E)-enal

The title compound is prepared analogously to Example 1b) from the corresponding epoxy alcohol according to a); light-yellow oil; IR (CH$_2$Cl$_2$): 3050, 2980, 2930, 2820, 2730, 1695, 1645, 1450, 1150, 1100 cm$^{-1}$; R$_f$=0.41 (hexane/ethyl acetate=3:2).

c) (4R,5R)-4,5-epoxy-1,1,1-trifluoro-11-(4-acetyl-3-hydroxy-2-propylphenoxy)-undeca-6(E),8(Z)-diene The title compound is prepared analogously to Example 1d) from the epoxyaldehyde according to b); light-yellow oil; R$_f$=0.48 (hexane/ethyl acetate 3:2).

EXAMPLE 24

Sodium salt of (4R,5S)-1,1,1-trifluoro-4-hydroxy-11-(4-acetyl-3-hydroxy-2-propylphenoxy)-undeca-6(E),8(Z)-dien-5-yl-7-thio-4-oxo-4H-1-benzopyrane-2-carboxylic acid The title compound is prepared analogously to Example 2 from the corresponding methyl ester according to Example 23; beige powder having a melting point of 198°-200°; $[\alpha]_D^{20}$ (methanol, 0.15%) = 127.3°±6.7°; UV (methanol): $\lambda_{max}(\epsilon) = 221$ (48820); 230/sh; 267 (25440); 285 (23080); 322/sh.

EXAMPLE 25

(4S,5R)-1,1,1-trifluoro-4-hydroxy-11-(4-acetyl-3-hydroxy-2-propylphenoxy)-undeca-6(E),8(Z)-dien-5-yl-7-thio-4-oxo-4H-1-benzopyrane-2-carboxylic acid methyl ester The title compound is prepared analogously to Example 1 from (4S,5S)-4,5-epoxy-1,1,1-trifluoro-11-(4-acetyl-3-hydroxy-2-propylphenoxy)-undeca-6(E),8(Z)-diene; colourless powder having a melting point of 69°-71°; $[\alpha]_D^{20} - = 153.3°\pm 6.7°$ (methanol, 0.15%). UV (methanol): $\lambda_{max}(\epsilon) = 220$ (49560); 235/sh; 270 (29220); 285/sh; 325 (12990).

The starting material is prepared, for example, as follows:

a) (2S,3S)-2,3-epoxy-6,6,6-trifluoro-hexanol

The title compound is prepared analogously to Example 1a) from 6,6,6-trifluoro-hex-2(E)-enol but using L(+)-tartaric acid diethyl ester; colourless oil; $[\alpha]_D^{20}$ (chloroform, 0.17%) = $-25.9°\pm 5.9°$; IR (methylene chloride): 3550, 3430, 2940, 2880, 2830, 1125 cm$^{-1}$.

b) (4S,5S)-4,5-epoxy-8,8,8-trifluoro-oct-2(E)-enal

The title compound is prepared analogously to Example 1b) from the corresponding epoxy alcohol according to a); light-yellow oil; IR (methylene chloride): 3050, 2990, 2930, 2820, 2730, 1695, 1645, 1450, 1150, 1100 cm$^{-1}$; R$_f$=0.36 (hexane/ethyl acetate 3:2).

c) (4S,5S)-4,5-epoxy-1,1,1-trifluoro-11-(4-acetyl-3-hydroxy-2-propylphenoxy)-undeca-6(E),8(Z)-diene The title compound is prepared analogously to Example 1d) from the corresponding epoxyaldehyde according to b); light-yellow oil.

EXAMPLE 26

Sodium salt of (4S,5R)-1,1,1-trifluoro-4-hydroxy-11-(4-acetyl-3-hydroxy-2-propylphenoxy)-undeca-6(E),8(Z)-dien-5-yl-7-thio-4-oxo-4H-1-benzopyrane-2-carboxylic acid The title compound is prepared analogously to Example 2 from the corresponding methyl ester according to Example 25; beige powder having a melting point of 201°–203°; $[\alpha]_D^{20}$ (methanol, 0.15%) = $-117.3° \pm 6.7°$; UV (methanol): $\lambda_{max}(\epsilon) = 222$ (48320); 233/sh; 267 (26440); 285 (24440); 330/sh.

EXAMPLE 27

(4R,5S)-1,1,1-trifluoro-4-hydroxy-9-(4-acetyl-3-hydroxy-2-propylphenoxy)-non-6(Z)-en-5-yl-7-thio-4-oxo-4H-1-benzopyrane-2-carboxylic acid methyl ester The title compound is prepared analogously to Example 1 from (4R,5R)-4,5-epoxy-1,1,1-trifluoro-9-(4-acetyl-3-hydroxy-2-propylphenoxy)-non-6(Z)-ene; colourless, viscous oil; IR (methylene chloride): 3530, 2920, 2890, 2820, 1720, 1640, 1605, 1585 cm$^{-1}$.

The starting material is prepared, for example, as follows:

a) (2S,3R)-2,3-epoxy-6,6,6-trifluoro-hexanal

The title compound is prepared analogously to Example 5a) from (2R,3R)-2,3-epoxy-6,6,6-trifluoro-hexanol; colourless liquid having a boiling point of 80°–81°/26 mbar.; $[\alpha]_D^{20}$ (chloroform, 0.15%) = $-10.7° \pm 6.7°$.

b) (4R,5R)-4,5-epoxy-1,1,1-trifluoro-9-(4-acetyl-3-hydroxy-2-propylphenoxy)-non-6(Z)-ene The title compound is prepared analogously to Example 1d) from the epoxyaldehyde according to a); light-yellow oil.

EXAMPLE 28

Sodium salt of (4R,5S)-1,1,1-trifluoro-4-hydroxy-9-(4-acetyl-3-hydroxy-2-propylphenoxy)-non-6(Z)-en-5-yl-7-thio-4-oxo-4H-1-benzopyrane-2-carboxylic acid The title compound is prepared analogously to Example 2 from the corresponding methyl ester according to Example 27; light-yellow powder having a melting point of 204°–206°; $[\alpha]_D^{20}$ (methanol, 0.15%) = 42.7° ± 6.7°;

UV (methanol): $\lambda_{max}(\epsilon) = 218$ (36920); 268 (20280); 285 (20180); 325/sh.

EXAMPLE 29

(5R,6S)-5-hydroxy-12-(4-acetyl-3-hydroxy-2-propylphenoxy)-dodec-7(Z)-en-6-yl-7-thio-4-oxo-4H-1-benzopyrane-2-carboxylic acid methyl ester The title compound is prepared analogously to Example 1 from (5R,6R)-5,6-epoxy-12-(4-acetyl-3-hydroxy-2-propylphenoxy)-dodec-7(Z)-ene; light-yellow oil; $R_f = 0.37$ (hexane/ethyl acetate 1:1).

The starting material is prepared, for example, as follows:

a) 5-(4-acetyl-3-hydroxy-2-propylphenoxy)-pentyl-triphenylphosphonium bromide

The title compound is prepared as in Example 1c) from 5-(4-acetyl-3-hydroxy-2-propylphenoxy)-pentyl bromide; colourless crystals having a melting point of 82°–85°.

b) (2S,3R)-2,3-epoxy-heptanal

The title compound is prepared analogously to Example 5a) from (2R,3R)-2,3-epoxy-heptanol; $[\alpha]_D^{20} = -99.4° \pm 0.1°$.

c) (5R,6R)-5,6-epoxy-12-(4-acetyl-3-hydroxy-2-propylphenoxy)-dodec-7(Z)-ene

The title compound is prepared analogously to Example 1d) from the epoxyaldehyde according to a), light-yellow oil.

EXAMPLE 30

Sodium salt of (5R,6S)-5-hydroxy-12-(4-acetyl-3-hydroxy-2-propylphenoxy)-dodec-7(Z)-en-6-yl-7-thio-4-oxo-4H-1-benzopyrane-2-carboxylic acid The title compound is prepared analogously to Example 2 from the corresponding methyl ester according to Example 29; m.p. 192°–194°; $[\alpha]_D^{20}$ (methanol, 0.125%) = +5.6° ± 8.0°; UV (methanol): $\lambda_{max}(\epsilon) = 218$ (38000); 268 (22040); 285 (21120); 325 sh.

EXAMPLE 31

(5S,6R)-5-hydroxy-12-(4-acetyl-3-hydroxy-2-propylphenoxy)-dodec-7(Z)-en-6-yl-7-thio-4-oxo-4H-1-benzopyrane-2-carboxylic acid methyl ester The title compound is prepared analogously to Example 1 from (5S,6S)-5,6-epoxy-12-(4-acetyl-3-hydroxy-2-propylphenoxy)-dodec-7(Z)-ene; light-yellow oil; $R_f = 0.41$ (hexane/ethyl acetate 1:1).

The starting material is prepared, for example, as follows:

a) (2R,3S)-2,3-epoxy-heptanal

The title compound is prepared analogously to Example 5a) from (2S,3S)-2,3-epoxy-heptanol; $[\alpha]_D^{20} = +104.3° \pm 0.4°$.

b) (5S,6S)-5,6-epoxy-12-(4-acetyl-3-hydroxy-2-propylphenoxy)-dodec-7(Z)-ene

The title compound is prepared analogously to Example 1d) from the epoxyaldehyde according to a); light-yellow oil, $R_f = 0.42$ (hexane/ethyl acetate 3:2).

EXAMPLE 32

Sodium salt of (5S,6R)-5-hydroxy-12-(4-acetyl-3-hydroxy-2-propylphenoxy)-dodec-7(Z)-en-6-yl-7-thio-4-oxo-4H-1-benzopyrane-2-carboxylic acid The title compound is prepared analogously to Example 2 from the corresponding methyl ester according to Example 31; m.p. 192°–194°; $[\alpha]_D^{20}$ (methanol, 0.145%) = 0° ± 6.9°; UV (methanol): $\lambda_{max}(\epsilon) = 218$ (37060); 268 (21760); 286 (20520); 325 sh.

EXAMPLE 33

(4R,5S)-1,1,1-trifluoro-4-hydroxy-11-(4-acetyl-3-hydroxy-2-propylphenoxy)-undec-6(Z)-en-5-yl-7-thio-4-oxo-4H-1-benzopyrane-2-carboxylic acid methyl ester The title compound is prepared analogously to Example 1 from (4R,5R)-4,5-epoxy-1,1,1-trifluoro-11-(4-acetyl-3-hydroxy-2-propylphenoxy)-undec-6(Z)-ene, light-yellow oil; $R_f = 0.47$ (hexane/ethyl acetate 1:1).

The starting material is prepared, for example, analogously to Example 1d) from (2S,3R)-2,3-epoxy-6,6,6-trifluoro-hexanal; light-yellow oil.

EXAMPLE 34

Sodium salt of (4R,5S)-1,1,1-trifluoro-4-hydroxy-11-(4-acetyl-3-hydroxy-2-propylphenoxy)-undec-6(Z)-en-5-yl-7-thio-4-oxo-4H-1-benzopyrane-2-carboxylic acid The title compound is prepared analogously to Example 2 from the corresponding methyl ester according to Example 33; m.p. 193°-195°; $[\alpha]_D^{20}$ (methanol, 0.135%) = +16.3° ± 7.4°; UV (MeOH): $\lambda_{max}(\epsilon) = 218$ (37380); 267 (21380); 286 (21020); 325/sh.

EXAMPLE 35

(5R,6S)-5-hydroxy-10-(4-acetyl-3-hydroxy-2-propylphenoxy)-dec-7(Z)-en-6-yl-7-thio-4-oxo-4H-1-benzopyrane-2-carboxylic acid methyl ester The title compound is prepared analogously to Example 1 from (5R,6R)-5,6-epoxy-10-(4-acetyl-3-hydroxy-2-propylphenoxy)-dec-7(Z)-ene, light-yellow oil; $[\alpha]_D^{20}$ (methanol, 0.135%) = +48.9° ± 7.4°; UV (methanol): $\lambda_{max}(\epsilon) = 216$ (38140); 271 (24040); 285 sh, 322 (12700).

The starting material is prepared, for example, analogously to Example 1d) from (2S,3R)-2,3-epoxy-heptanal; light-yellow oil. $R_f = 0.45$ (hexane/ethyl acetate = 7:3).

EXAMPLE 36

(5R,6S)-5-hydroxy-10-(4-acetyl-3-hydroxy-2-propylphenoxy)-dec-7(Z)-en-6-yl-7-thio-4-oxo-4H-1-benzopyrane-2-carboxylic acid The title compound is prepared analogously to Example 2 from the corresponding methyl ester according to Example 35 and is converted into the free acid with hydrochloric acid; m.p. 58°-60°; $[\alpha]_D^{20}$ (methanol, 0.130%) = +36.2° ± 7.7°; UV (methanol): $\lambda_{max}(\epsilon) = 218$ (35240); 269 (20760); 283 (19800); 330 sh.

EXAMPLE 37

(5S,6R)-5-hydroxy-10-(4-acetyl-3-hydroxy-2-propylphenoxy)-dec-7(Z)-en-6-yl-7-thio-4-oxo-4H-1-benzopyrane-2-carboxylic acid methyl ester The title compound is prepared analogously to Example 1 from (5S,6S)-5,6-epoxy-10-(4-acetyl-3-hydroxy-2-propylphenoxy)-dec-7(Z)-ene, light-yellow oil; $[\alpha]_D^{20}$ (methanol, 0.115%) = −50.4° ± 8.7°; UV (MeOH): $\lambda_{max}(\epsilon) = 217$ (38000); 271 (24100); 285 sh, 321 (12800).

The starting material is prepared, for example, analogously to Example 1d) from (2R,3S)-2,3-epoxy-heptanal; light-brown oil; $R_f = 0.52$ (hexane/ethyl acetate 7:3).

EXAMPLE 38

Sodium salt of (5S,6R)-5-hydroxy-10-(4-acetyl-3-hydroxy-2-propylphenoxy)-dec-7(Z)-en-6-yl-7-thio-4-oxo-4H-1-benzopyrane-2-carboxylic acid The title compound is prepared analogously to Example 2 from the corresponding methyl ester according to Example 37; m.p. 224°-226°, $[\alpha]_D^{20}$ (methanol, 0.145%) = −29.0° ± 6.9°; UV (methanol): $\lambda_{max}(\epsilon) = 219$ (38760); 268 (21880); 285 (21260); 325 sh.

EXAMPLE 39

(5S,6R)-5-hydroxy-10-(4-acetyl-3-hydroxy-2-propylphenoxy)-dec-7(Z)-en-6-yl-7-thio-4-oxo-4H-1-benzopyrane-2-(N-benzenesulfonamidyl)-carboxamide A solution of 0.20 g of (5S,6R)-5-hydroxy-10-(4-acetyl-3-hydroxy-2-propylphenoxy)-dec-7(Z)-en-6-yl-7-thio-4-oxo-4H-1-benzopyrane-2-carboxylic acid in 10 ml of methylene chloride is stirred under argon at room temperature with 60 mg of benzenesulfonamide, 44 mg of 4-dimethylaminopyridine and 70 mg of N-ethyl-N'-(3-dimethylaminopropyl)-carbodiimide hydrochloride for 24 hours. The resulting solution is diluted with 30 ml of methylene chloride, washed twice with 1N hydrochloric acid and twice with brine, dried over magnesium sulfate and concentrated by evaporation. Chromatography of the residue on silica gel with methylene chloride/methanol (9:1) yields the title compound having a melting point of 140°-142°.

EXAMPLE 40

(4RS,5SR)-1-methoxycarbonyl-4-hydroxy-9-(4-acetyl-3-hydroxy-2-propylphenoxy)-non-6(Z)-en-5-yl-7-thio-4-oxo-4H-1-benzopyrane-2-carboxylic acid methyl ester The title compound is prepared analogously to Example 1 from (4RS,5RS)-4,5-epoxy-1-methoxycarbonyl-9-(4-acetyl-3-hydroxy-2-propylphenoxy)-non-6(Z)-ene; colourless oil; $[\alpha]_D^{20}$ (methanol, 0.125%) = 0.0° ± 8.0°; UV (methanol): $\lambda_{max}(t) = 270$ (24000); 340 (13200).

The starting material is prepared, for example, analogously to Example 1d) from 5,6-epoxy-6-formylhexanoic acid methyl ester; light-yellow oil; $R_f = 0.35$ (hexane/ethyl acetate 3:2).

EXAMPLE 41

Disodium salt of (4RS,5SR)-1-carboxy-4-hydroxy-9-(4-acetyl-3-hydroxy-2-propylphenoxy)-non-6(Z)-en-5-yl-7-thio-4-oxo-4H-1-benzopyrane-2-carboxylic acid 0.24 g of the methyl ester according to Example 40 is dissolved under argon in 15 ml of tetrahydrofuran; 3.8 ml of 0.2N sodium hydroxide solution are added and the mixture is stirred for 20 hours at room temperature. Concentration by evaporation and purification of the residue by chromatography on a "Reversed Phase" silica gel column (for example Merck Lichroprep ® RP-8) with methanol/water (7:3) yield the title compound having a melting point of 248°-250° (decomp.); UV (methanol): $\lambda_{max}(\lambda) = 218$ (33900); 268 (18580); 284 (18240); 330 sh.

EXAMPLE 42

(1R,2S)-1-hydroxy-1-(3-trifluoromethylphenyl)-10-(4-acetyl-3-hydroxy-2-propylphenoxy)-deca-3(E),5(Z)-dien-2-yl-7-thio-4-oxo-4H-1-benzopyrane-2-carboxylic acid methyl ester The title compound is prepared analogously to Example 1 from (1R,2R)-1,2-epoxy-1-(3-trifluoromethylphenyl)-10-(4-acetyl-3-hydroxy-2-propylphenoxy)-deca-3(E),5(Z)-diene; light-yellow oil. $[\alpha]_D^{20}$ (CHCl$_3$, 0.363%) = 46.6° ± 2.8°; UV (CHCl$_3$): $\lambda_{max}(\epsilon)$ = 270 (26500); 285 (24240); 322 (15200).

The starting material is prepared, for example, as follows:

a)

(1R,2R)-1,2-epoxy-1-(3-trifluoromethylphenyl)-10-(4-acetyl-3-hydroxy-2-propylphenoxy)-deca-3(E),5(Z)-diene The title compound is prepared analogously to Example 1d) from 5-(4-acetyl-3-hydroxy-2-propylphenoxy)-pentyltriphenylphosphonium bromide (Example 29a) and (4R,5R)-4,5-epoxy-(3-trifluoromethylphenyl)-pent-2(E)-enal (Example 1b); light-brown oil; $[\alpha]_D^{20}$ (CHCl$_3$, 0.224%) = 70.8° ± 10°; R$_f$=0.50 (hexane/ethyl acetate = 1:1); IR (CH2Cl2): 2960, 2930, 2865, 1735, 1625, 1330, 1125 cm$^{-1}$.

EXAMPLE 43

Sodium salt of (1R,2S)-1-hydroxy-1-(3-trifluoromethylphenyl)-10-(4-acetyl-3-hydroxy-2-propylphenoxy)-deca-3(E),5(Z)-dien-2-yl-7-thio-4-oxo-4H-1-benzopyrane-2-carboxylic acid The title compound is prepared analogously to Example 2 from the corresponding methyl ester (Example 42); m.p. 217°-219°; $[\alpha]_D^{20}$ (MeOH, 0.160%) = 145.6° ± 6.3°; UV (MeOH): $\lambda_{max}(\epsilon)$ = 220 (50480), 230 (sh), 267 (26240), 284 (23000), 320 sh.

EXAMPLE 44

(1R,2S)-1-hydroxy-1-(3-methylphenyl)-10-(4-acetyl-3-hydroxy-2-propylphenoxy)-deca-3(E),5(Z)-dien-2-yl-7-thio-4-oxo-4H-1-benzopyrane-2-carboxylic acid methyl ester The title compound is prepared analogously to Example 1 from (1R,2R)-1,2-epoxy-1-(3-methylphenyl)-10-(4-acetyl-3-hydroxy-2-propylphenoxy)-deca-3(E),5(Z)-diene; m.p. 59°-60°; $[\alpha]_D^{20}$ (CHCl$_3$, 0.163%) = 31.9° ± 6.1°; UV (CHCl$_3$): $\lambda_{max}(\epsilon)$ = 241 (31420); 286 (23060).

The starting material is prepared, for example, as follows:

a)

(1R,2R)-1,2-epoxy-1-(3-methylphenyl)-10-(4-acetyl-3-hydroxy-2-propylphenoxy)-deca-3(E),5(Z)-diene The title compound is prepared analogously to Example 1d) from 5-(4-acetyl-3-hydroxy-2-propylphenoxy)-pentyltriphenylphosphonium bromide (Example 29a) and (4R,5R)-4,5-epoxy-5-(3-methylphenyl)-pent-2(E)-enal (Example 9b); light-yellow oil; $[\alpha]_D^{20}$ (CHCl3, 0.273%) = 118.7° ± 3.7°. R$_f$=0.62 (hexane/ethyl acetate = 3:2).

EXAMPLE 45

Sodium salt of (1R,2S)-1-hydroxy-1-(3-methylphenyl)-10-(4-acetyl-3-hydroxy-2-propylphenoxy)-deca-3(E),5(Z)-dien-2-yl-7-thio-4-oxo-4H-1-benzopyrane-2-carboxylic acid The title compound is prepared analogously to Example 2 from the corresponding methyl ester (Example 44); m.p. 208°-210°; $[\alpha]_D^{20}$ (MeOH, 0.30%) = 50.7° ± 3.3°. UV (MeOH): $\lambda_{max}(\epsilon)$ = 219 (52420), 230 (sh), 267 (26620), 285 (23520), 325 (sh).

EXAMPLE 46

(1S,2R)-1-hydroxy-1-(3-trifluoromethylphenyl)-10-(4-acetyl-3-hydroxy-2-propylphenoxy)-deca-3(E),5(Z)-dien-2-yl-7-thio-4-oxo-4H-1-benzopyrane-2-carboxylic acid methyl ester The title compound is prepared analogously to Example 1 from (1S,2S)-1,2-epoxy-1-(3-trifluoromethylphenyl)-10-(4-acetyl-3-hydroxy-2-propylphenoxy)-deca-3(E),5(Z)-diene; viscous mass; R$_f$=0.48 (hexane/ethyl acetate = 1:1).

The starting material is prepared, for example, as follows:

a)

(1S,2S)-1,2-epoxy-1-(3-trifluoromethylphenyl)-10-(4-acetyl-3-hydroxy-2-propylphenoxy)-deca-3(E),5(Z)-diene The title compound is prepared analogously to Example 1d) from 5-(4-acetyl-3-hydroxy-2-propylphenoxy)-pentyltriphenylphosphonium bromide (Example 29a) and (4S,5S)-4,5-epoxy-5-(3-trifluoromethylphenyl)-pent-2(E)-enal (Example 3b); light-yellow oil; $[\alpha]_D^{20}$ (chloroform, 0.454% = −86.8° ± 2.2°; R$_f$=0.46 (hexane/ethyl acetate = 1:1). IR (methylene chloride): 2960, 2930, 1730, 1625, 1330, 1130 cm$^{-1}$.

EXAMPLE 47

Sodium salt of (1S,2R)-1-hydroxy-1-(3-trifluoromethylphenyl)-10-(4-acetyl-3-hydroxy-2-propylphenoxy)-deca-3(E),5(Z)-dien-2-yl-7-thio-4-oxo-4H-1-benzopyrane-2-carboxylic acid The title co.pound is prepared analogously to Example 2 from the corresponding methyl ester (Example 46); m.p. 168°-170°; $[\alpha]_D^{20}$ (methanol, 0.150%) = −66.7° ± 6.7°; UV (MeOH): $\lambda_{max}(\epsilon)$ = 220 (49640), 230 (sh), 266 (25640), 285 (22140), 320 (sh).

EXAMPLE 48

(1R,2S)-1-hydroxy-1-(3-trifluoromethylphenyl)-8-[4-acetyl-3-hydroxy-2-(3,3,3-trifluoropropyl)-phenoxy]-octa-3(E),5(Z)-dien-2-yl-7-thio-4-oxo-4H-1-benzopyrane-2-carboxylic acid methyl ester The title compound is prepared analogously to Example 1 from (1R,2R)-1,2-epoxy-1-(3-trifluoromethylphenyl)-8-[4-acetyl-3-hydroxy-2-(3,3,3-trifluoropropyl)-phenoxy]-octa-3(E),5(Z)-diene; light-yellow oil; R$_f$=0.34 (hexane/ethyl acetate = 1:1).

The starting material is prepared, for example, as follows:

a)
(1R,2R)-1,2-epoxy-1-(3-trifluoromethylphenyl)-8-[4-acetyl-3-hydroxy-2-(3,3,3-trifluoropropyl)-phenoxy]-octa-3(E),5(Z)-diene The title compound is prepared analogously to Example 1d) from 3-[4-acetyl-3-hydroxy-2-(3,3,3-trifluoropropyl)-phenoxy]-propyltriphenylphosphonium bromide and (4R,5R)-4,5-epoxy-5-(3-trifluoromethylphenyl)-pent-2(E)-enal (Example 1b); light-yellow oil; $[\alpha]_D^{20}$ (chloroform, 0.406%) = −58.6° ±2.5°; $R_f$=0.45 (hexane/ethyl acetate=7:3). IR (methylene chloride): 2945, 1670, 1610, 1310, 1055 cm$^{-1}$.

b)
3-[4-acetyl-3-hydroxy-2-(3,3,3-trifluoropropyl)-phenoxy]-propyltriphenylphosphonium bromide The title compound is prepared analogously to Example 1c) from 3-[4-acetyl-3-hydroxy-2-(3,3,3-trifluoropropyl)-phenoxy]-propyl bromide. M.p. 184°–185°.

EXAMPLE 49

Sodium salt of (1R,2S)-1-hydroxy-1-(3-trifluoromethylphenyl)-8-[4-acetyl-3-hydroxy-2-(3,3,3-trifluoropropyl)-phenoxy]-octa-3(E),5(Z)-dien-2-yl-7-thio-4-oxo-4H-1-benzopyrane-2-carboxylic acid The title compound is prepared analogously to Example 2 from the corresponding methyl ester (Example 48); m.p. 238°–240°; $[\alpha]_D^{20}$ (methanol, 0.150%)=208° ±6.6°; UV (MeOH): $\lambda_{max}(\epsilon)$=216 (50040), 230 (sh), 267 (28960), 280 (sh), 320 (16020).

EXAMPLE 50

(1R,2S)-1-hydroxy-1-(3-methylphenyl)-8-[4-acetyl-3-hydroxy-2-(3,3,3-trifluoropropyl)-phenoxy]-octa-3(E),5(Z)-dien-2-yl-7-thio-4-oxo-4H-1-benzopyrane-2-carboxylic acid methyl ester The title compound is prepared analogously to Example 1 from (1R,2R)-1,2-epoxy-1-(3-methylphenyl)-8-[4-acetyl-3-hydroxy-2-(3,3,3-trifluoropropyl)-phenoxy]-octa-3(E),5(Z)-diene; light-yellow, viscous oil; $R_f$=0.41 (hexane/ethyl acetate=1:1). $[\alpha]_D^{20}$ (chloroform, 0.155%)=32.3° ±6.5°. UV (chloroform): $\lambda_{max}(\epsilon)$=271 (32320), 318 (16100).

The starting material is prepared, for example, as follows:

a)
(1R,2R)-1,2-epoxy-1-(3-methylphenyl)-8-[4-acetyl-3-hydroxy-2-(3,3,3-trifluoropropyl)-phenoxy]-octa-3(E),5(Z)-diene The title compound is prepared analogously to Example 1d) from 3-[4-acetyl-3-hydroxy-2-(3,3,3-trifluoropropyl)-phenoxy]-propyltriphenylphosphonium bromide (Example 48b) and (4R,5R)-4,5-epoxy-5-(3-methylphenyl)-pent-2(E)-enal (Example 9b), light-yellow oil; $R_f$=0.38 (hexane/ethyl acetate=3:2).

EXAMPLE 51

Sodium salt of (1R,2S)-1-hydroxy-1-(3-methylphenyl)-8-[4-acetyl-3-hydroxy-2-(3,3,3-trifluoropropyl)-phenoxy]-octa-3(E),5(Z)-dien-2-yl-7-thio-4-oxo-4H-1-benzopyrane-2-carboxylic acid The title compound is prepared analogously to Example 2 from the corresponding methyl ester (Example 50); m.p. 233°–235°; $[\alpha]_D^{20}$ (methanol, 0.195%)=69.7° ±5.1°; UV (MeOH): $\lambda_{max}(\epsilon)$=218 (52320), 230 (sh), 267 (29040), 280 (sh), 320 (16000).

EXAMPLE 52

(1R,2S)-1-hydroxy-1-(2-trifluoromethylphenyl)-8-(4-acetyl-3-hydroxy-2-propylphenoxy)-octa-3(E),5(Z)-dien-2-yl-7-thio-4-oxo-4H-1-benzopyrane-2-carboxylic acid methyl ester The title compound is prepared analogously to Example 1 from (1R,2R)-1,2-epoxy-1-(2-trifluoromethylphenyl)-8-(4-acetyl-3-hydroxy-2-propylphenoxy)-octa-3(E),5(Z)-diene; m.p. 66°–68°; $R_f$=0.23 (hexane/ethyl acetate=3:2). $[\alpha]_D^{20}$ (methanol, 0.150%)=22.0° ±6.7°; UV (MeOH): $\lambda_{max}(\epsilon)$=216 (50000), 238 (sh), 271 (27860), 285 (sh), 324 (13900).

The starting material is prepared, for example, as follows:

a)
(1R,2R)-1,2-epoxy-1-(2-trifluoromethylphenyl)-8-(4-acetyl-3-hydroxy-2-propylphenoxy)-octa-3(E),5(Z)-diene The title compound is prepared analogously to Example 1d) from 3-(4-acetyl-3-hydroxy-2-propylphenoxy)-propyltriphenylphosphonium bromide (Example 1c) and (4R,5R)-4,5-epoxy-5-(2-trifluoromethylphenyl)-pent-2(E)-enal; light-brown oil; $[\alpha]_D^{20}$ (chloroform, 0.207%)=−5.8° ±4.8° $R_f$=0.25 (hexane/ethyl acetate=4:1).

b)
(4R,5R)-4,5-epoxy-5-(2-trifluoromethylphenyl)-pent-2(E)-enal

The title compound is prepared analogously to Example 1b) from (2R,3R)-2,3-epoxy-3-(2-trifluoromethylphenyl)-propanol; yellow crystals; $R_f$=0.36 (hexane/ethyl acetate=4:1). $[\alpha]_D^{20}$ (methanol, 0.165%)=23.0±6.1; UV (MeOH): $\lambda_{max}(\epsilon)$=216 (14400), 235 (17240).

c)
(2R,3R)-2,3-epoxy-3-(2-trifluoromethylphenyl)-propanol

The title compound is prepared analogously to Example 1a) from 3-(2-trifluoromethylphenyl)-prop-2(E)-enol; colourless crystals; $R_f$=0.38 (hexane/ethyl acetate=3:2); IR (methylene chloride): 3600, 3050, 2990, 2920, 2870, 1610, 1585, 1320, 1170, 1125 cm$^{-1}$.

EXAMPLE 53

Sodium salt of (1R,2S)-1-hydroxy-1-(2-trifluoromethylphenyl)-8-(4-acetyl-3-hydroxy-2-propylphenoxy)-octa-3(E),5(Z)-dien-2-yl-7-thio-4-oxo-4H-1-benzopyrane-2-carboxylic acid The title compound is prepared analogously to Example 2 from the corresponding methyl ester (Example 52); m.p. 155°–157°; $[\alpha]_D^{20}$ (methanol, 0.180%)=12.8° ±5.6°; UV (MeOH): $\lambda_{max}(\epsilon)$=219 (48400), 230 (sh), 266 (25480), 284 (22540), 325 (sh).

EXAMPLE 54

(1S,2R)-1-hydroxy-1-(2-trifluoromethylphenyl)-8-(4-acetyl-3-hydroxy-2-propylphenoxy)-octa-3(E),5(Z)-dien-2-yl-7-thio-4-oxo-4H-1-benzopyrane-2-carboxylic acid methyl ester The title compound is prepared analogously to Example 1 from (1S,2S)-1,2-epoxy-1-(2-trifluoromethylphenyl)-8-(4-acetyl-3-hydroxy-2-propylphenoxy)-octa-3(E),5(Z)-diene; m.p. 71°-73°; $R_f=0.25$ (hexane/ethyl acetate=3:2). $[\alpha]_D^{20}$ (methanol, 0.170%)= $-27.1°\pm5.9°$; UV (MeOH): $\lambda_{max}(\epsilon)=216$ (51040), 235 (sh), 271 (28140), 285 (sh), 324 (13500).

The starting material is prepared, for example, as follows:

a)

(1S,2S)-1,2-epoxy-1-(2-trifluoromethylphenyl)-8-(4-acetyl-3-hydroxy-2-propylphenoxy)-octa-3(E),5(Z)-diene The title compound is prepared analogously to Example 1d) from 3-(4-acetyl-3-hydroxy-2-propylphenoxy)-propyl-triphenylphosphonium bromide (Example 1c) and (4S,5S)-4,5-epoxy-5-(2-trifluoromethylphenyl)-pent-2(E)-enal; reddish oil; $[\alpha]_D^{20}$ (chloroform, 0.207%)=$5.4°\pm4.8°$; $R_f=0.29$ (hexane/ethyl acetate=4:1).

b)

(4S,5S)-4,5-epoxy-5-(2-trifluoromethylphenyl)-pent-2(E)-enal

The title compound is prepared analogously to Example 1b) from (2S,3S)-2,3-epoxy-3-(2-trifluoromethylphenyl)-propanol; yellow crystals; $R_f=0.38$ (hexane/ethyl acetate=4:1); $[\alpha]_D^{20}$ (methanol, 0.180%)= $-25.0°\pm5.6°$; UV (MeOH): $\lambda_{max}(\epsilon)=215$ (13960), 236 (17060).

c)

(2S,3S)-2,3-epoxy-3-(2-trifluoromethylphenyl)-propanol

The title compound is prepared analogously to Example 1a) from 3-(2-trifluoromethylphenyl)-prop-2(E)-enol; colourless crystals; $R_f=0.35$ (hexane/ethyl acetate=3:2). IR (methylene chloride): 3600, 3050, 2990, 2920, 2870, 1610, 1585, 1320, 1170, 1125 cm$^{-1}$.

EXAMPLE 55

Sodium salt of (1S,2R)-1-hydroxy-1-(2-trifluoromethylphenyl)-8-(4-acetyl-3-hydroxy-2-propylphenoxy)-octa-3(E),5(Z)-dien-2-yl-7-thio-4-oxo-4H-1-benzopyrane-2-carboxylic acid The title compound is prepared analogously to Example 2 from the corresponding methyl ester (Example 54); m.p. 182°-184°; $[\alpha]_D^{20}$ (methanol, 0.205%)= $-16.6°\pm4.9°$; UV (MeOH): $\lambda_{max}(\epsilon)=219$ (47680), 235 (sh), 266 (24960), 284 (22100), 330 (sh).

EXAMPLE 56

(1R,2S)-1-hydroxy-1-(4-trifluoromethylphenyl)-8-(4-acetyl-3-hydroxy-2-propylphenoxy)-octa-3(E),5(Z)-dien-2-yl-7-thio-4-oxo-4H-1-benzopyrane-2-carboxylic acid methyl ester The title compound is prepared analogously to Example 1 from (1R,2R)-1,2-epoxy-1-(4-trifluoromethylphenyl)-8-(4-acetyl-3-hydroxy-2-propylphenoxy)-octa-3(E),5(Z)-diene; m.p. 68°-70°; $R_f=0.16$ (hexane/ethyl acetate=3:2). $[\alpha]_D^{20}$ (methanol, 0.155%)=$110.3°\pm6.5°$; UV (MeOH): $\lambda_{max}(\epsilon)=217$ (52880), 236 (sh), 270 (28880), 285 (sh), 326 (13700).

The starting material is prepared, for example, as follows:

a)

(1R,2R)-1,2-epoxy-1-(4-trifluoromethylphenyl)-8-(4-acetyl-3-hydroxy-2-propylphenoxy)-octa-3(E),5(Z)-diene The title compound is prepared analogously to Example 1d) from 3-(4-acetyl-3-hydroxy-2-propylphenoxy)-propyltriphenylphosphonium bromide (Example 1c) and (4R,5R)-4,5-epoxy-5-(4-trifluoromethylphenyl)-pent-2(E)-enal; yellow oil; $[\alpha]_D^{20}$ (chloroform, 0.220%)=$6.5°\pm4.5°$; $R_f=0.35$ (hexane/ethyl acetate=4:1).

b)

(4R,5R)-4,5-epoxy-5-(4-trifluoromethylphenyl)-pent-2(E)-enal

The title compound is prepared analogously to Example 1b) from (2R,3R)-2,3-epoxy-3-(4-trifluoromethylphenyl)-propanol; yellow crystals; m.p. 67°-70°; $R_f=0.24$ (hexane/ethyl acetate=4:1). $[\alpha]_D^{20}$ (methanol, 0.150%)=$171.3°\pm6.7°$; UV (MeOH): $\lambda_{max}(\epsilon)=237$ (19660).

c)

(2R,3R)-2,3-epoxy-3-(4-trifluoromethylphenyl)-propanol

The title compound is prepared analogously to Example 1a) from 3-(4-trifluoromethylphenyl)-prop-2(E)-enol; colourless crystals; $R_f=0.25$ (hexane/ethyl acetate=3:2). IR (methylene chloride): 3550, 3010, 2950, 2880, 2830, 1605, 1310, 1150, 1110, 1050 cm$^{-1}$.

EXAMPLE 57

Sodium salt of (1R,2S)-1-hydroxy-1-(4-trifluoromethylphenyl)-8-(4-acetyl-3-hydroxy-2-propylphenoxy)-octa-3(E),5(Z)-dien-2-yl-7-thio-4-oxo-4H-1-benzopyrane-2-carboxylic acid The title compound is prepared analogously to Example 2 from the corresponding methyl ester (Example 56); m.p. 229°-231°; $[\alpha]_D^{20}$ (methanol, 0.160%)=$118.8°\pm6.3°$; UV (MeOH): $\lambda_{max}(\epsilon)=220$ (53060), 235 (sh), 267 (27280), 284 (23880), 320 (16300).

EXAMPLE 58

(1S,2R)-1-hydroxy-1-(4-trifluoromethylphenyl)-8-(4-acetyl-3-hydroxy-3-propylphenoxy)-octa-3(E),5(Z)-dien-2-yl-7-thio-4-oxo-4H-1-benzopyrane-2-carboxylic acid methyl ester The title compound is prepared analogously to Example 1 from (1S,2S)-1,2-epoxy-1-(4-trifluoromethylphenyl)-8-(4-acetyl-3-hydroxy-2-propylphenoxy)-octa-3(E),5(Z)-diene; m.p. 67°-69°; $R_f=0.13$ (hexane/ethyl acetate=3:2); $[\alpha]_D^{20}$ (methanol, 0.155%)=$109.7°\pm6.5°$; UV (MeOH): $\lambda_{max}(\epsilon)=217$ (52640), 235 (sh), 270 (28660), 285 (sh), 326 (13680).

The starting material is prepared, for example, as follows:

a)
(1S,2S)-1,2-epoxy-1-(4-trifluoromethylphenyl)-8-(4-acetyl-3-hydroxy-2-propylphenoxy)-octa-3(E),5(Z)-diene The title compound is prepared analogously to Example 1d) from 3-(4-acetyl-3-hydroxy-2-propylphenoxy)-propyl-triphenylphosphonium bromide (Example 1c) and (4S,5S)-4,5-epoxy-5-(4-trifluoromethylphenyl)-pent-2(E)-enal; reddish oil; $[\alpha]_D^{20}$ (chloroform, 0.199%) = −5.4°±5.0°; $R_f$=0.23 (hexane/ethyl acetate=4:1).

b)
(4S,5S)-4,5-epoxy-5-(4-trifluoromethylphenyl)-pent-2(E)-enal

The title compound is prepared analogously to Example 1b) from (2S,3S)-2,3-epoxy-3-(4-trifluoromethylphenyl)-propanol; yellow crystals; m.p. 67°–69°. $R_f$=0.18 (hexane/ethyl acetate=4:1). $[\alpha]_D^{20}$ (methanol, 0.150%) = −180.0°±6.7°; UV (MeOH): $\lambda_{max}(\epsilon)$=236 (19740).

c)
(2S,3S)-2,3-epoxy-3-(4-trifluoromethylphenyl)-propanol

The title compound is prepared analogously to Example 1a) from 3-(4-trifluoromethylphenyl)-prop-2(E)-enol; colourless crystals; $R_f$=0.23 (hexane/ethyl acetate=3:2). IR (methylene chloride): 3550, 3010, 2950, 2880, 2830, 1605, 1310, 1150, 1110, 1050 cm⁻¹.

EXAMPLE 59
Sodium salt of (1S,2R)-1-hydroxy-1-(4-trifluoromethylphenyl)-8-(4-acetyl-3-hydroxy-2-propylphenoxy)-octa-3(E),5(Z)-dien-2-yl-7-thio-4-oxo-4H-1-benzopyrane-2-carboxylic acid The title compound is prepared analogously to Example 2 from the corresponding methyl ester (Example 58); m.p. 228°–230°; $[\alpha]_D^{20}$ (methanol, 0.175%) = −99.4°±5.7°; UV (MeOH): $\lambda_{max}(\epsilon)$=220 (49800), 235 (sh), 267 (25320), 284 (22200), 320 (15600).

EXAMPLE 60
(1R,2S)-1-hydroxy-1-(3-trifluoromethylphenyl)-8-(4-acetyl-3-hydroxy-2-propylphenoxy)-octa-3(Z)-en-2-yl-7-thio-4-oxo-4H-1-benzopyrane-2-carboxylic acid methyl ester The title compound is prepared analogously to Example 1 from (1R,2R)-1,2-epoxy-1-(3-trifluoromethylphenyl)-8-(4-acetyl-3-hydroxy-2-propylphenoxy)-octa-3(Z)-ene; colourless oil; $R_f$=0.41 (hexane/ethyl acetate=1:1); $[\alpha]_D^{20}$ (chloroform, 0.150%)=46.7°±6.7°; UV (MeOH): $\lambda_{max}(\epsilon)$=271 (22760), 288 (20060), 270 (28880), 324 (14460).

The starting material is prepared, for example, as follows:

a)
(1R,2R)-1,2-epoxy-1-(3-trifluoromethylphenyl)-8-(4-acetyl-3-hydroxy-2-propylphenoxy)-octa-3(Z)-ene The title compound is prepared analogously to Example 1d) from 3-(4-acetyl-3-hydroxy-2-propylphenoxy)-pentyl-triphenylphosphonium bromide (Example 29a) and (2S,3R)-2,3-epoxy-3-(3-trifluoromethylphenyl)-propanal (Example 5a); light-yellow oil; $[\alpha]_D^{20}$ (chloroform, 0.221%)=25.3°±4.5°; $R_f$=0.56 (hexane/ethyl acetate=3:2).

EXAMPLE 61
Sodium salt of (1R,2S)-1-hydroxy-1-(3-trifluoromethylphenyl)-8-(4-acetyl-3-hydroxy-2-propylphenoxy)-octa-3(Z)-en-2-yl-7-thio-4-oxo-4H-1-benzopyrane-2-carboxylic acid The title compound is prepared analogously to Example 2 from the corresponding methyl ester (Example 60); m.p. 231°–233°; $[\alpha]_D^{20}$ (methanol, 0.190%)=51.1°±5.3°; UV (MeOH): $\lambda_{max}(\epsilon)$=215 (42320), 267 (22220), 286 (20800), 320 (sh).

EXAMPLE 62
(1R,2S)-1-hydroxy-1-(3-trifluoromethylphenyl)-9-(4-acetyl-3-hydroxy-2-propylphenoxy)-nona-3(E),5(Z)-dien-2-yl-7-thio-4-oxo-4H-1-benzopyrane-2-carboxylic acid methyl ester The title compound is prepared analogously to Example 1 from (1R,2R)-1,2-epoxy-1-(3-trifluoromethylphenyl)-9-(4-acetyl-3-hydroxy-2-propylphenoxy)-nona-3(E),5(Z)-diene; light-yellow viscous oil; $[\alpha]_D^{20}$ (chloroform, 0.155%)=44.5°±6.5°; $R_f$=0.50 (hexane/ethyl acetate=1:1); UV (CHCl₃): $\lambda_{max}(\epsilon)$=270 (26800), 284 (23100), 323 (14480).

The starting material is prepared, for example, as follows:

a)
3-(4-acetyl-3-hydroxy-2-propylphenoxy)-butyl-triphenylphosphonium bromide The title compound is prepared analogously to Example 1c) from 3-(4-acetyl-3-hydroxy-2-propylphenoxy)-butyl bromide; m.p. 167°–169°.

b)
(1R,2R)-1,2-epoxy-1-(3-trifluoromethylphenyl)-9-(4-acetyl-3-hydroxy-2-propylphenoxy)-nona-3(E),5(Z)-diene The title compound is prepared analogously to Example 1d) from 5-(4-acetyl-3-hydroxy-2-propylphenoxy)-butyl-triphenylphosphonium bromide and (4R,5R)-4,5-epoxy-5-(3-trifluoromethylphenyl)-pent-2(E)-enal (Example 1b); light-yellow oil; $[\alpha]_D^{20}$ (chloroform, 0.308%)=40.7°±3.2°; $R_f$=0.70 (hexane/ethyl acetate=3:2); IR (methylene chloride): 2950, 2860, 1625, 1325, 1120 cm⁻¹.

EXAMPLE 63
Sodium salt of (1R,2S)-1-hydroxy-1-(3-trifluoromethylphenyl)-9-(4-acetyl-3-hydroxy-2-propylphenoxy)-nona-3(E),5(Z)-dien-2-yl-7-thio-4-oxo-4H-1-benzopyrane-2-carboxylic acid The title compound is prepared analogously to Example 2 from the corresponding methyl ester (Example 62); m.p. 204°–206°; $[\alpha]_D^{20}$ (chloroform, 0.289%)=8.0°±3.5°; $[\alpha]_D^{20}$=55.5°±6.5° (methanol, 0.155%); UV (methanol): $\lambda_{max}(\epsilon)$=219 (49320), 232 (sh), 266 (25800), 285 (22060), 330 (sh).

EXAMPLE 64

(1R,2S)-1-hydroxy-1-(3-trifluoromethylphenyl)-11-(4-acetyl-3-hydroxy-2-propylphenoxy)-undeca-3(E),5(Z)-dien-2-yl-7-thio-4-oxo-4H-1-benzopyrane-2-carboxylic acid methyl ester The title compound is prepared analogously to Example 1 from (1R,2R)-1,2-epoxy-1-(3-trifluoromethylphenyl)-11-(4-acetyl-3-hydroxy-2-propylphenoxy)-undeca-3(E),5(Z)-diene; light-yellow viscous oil; $[\alpha]_D^{20}$ (chloroform, 0.160%) = 48.1° ± 6.3°; $R_f$ = 0.50 (hexane/ethyl acetate = 1:1). UV (CHCl$_3$): $\lambda_{max}(\epsilon)$ = 270 (27120), 286 (23300), 323 (14740).

The starting material is prepared, for example, as follows:

a) 3-(4-acetyl-3-hydroxy-2-propylphenoxy)-hexyl-triphenylphosphonium bromide The title compound is prepared analogously to Example 1c) from 3-(4-acetyl-3-hydroxy-2-propylphenoxy)-hexyl bromide; the compound crystallises very slowly.

b) (1R,2R)-1,2-epoxy-1-(3-trifluoromethylphenyl)-11-(4-acetyl-3-hydroxy-2-propylphenoxy)-undeca-3(E),5(Z)-diene The title compound is prepared analogously to Example 1d from 5-(4-acetyl-3-hydroxy-2-propylphenoxy)-hexyl-triphenylphosphonium bromide and (4R,5R)-4,5-epoxy-5-(3-trifluoromethylphenyl)-pent-2(E)enal (Example 1b); light-yellow oil; $[\alpha]_D^{20}$ (chloroform, 0.450%) = 41.1° ± 2.2°; $R_f$ = 0.66 (hexane/ethyl acetate = 3:2); IR (methylene chloride): 2960, 2860, 1625, 1325, 1120 cm$^{-1}$.

EXAMPLE 65

Sodium salt of (1R,2S)-1-hydroxy-1-(3-trifluoromethylphenyl)-11-(4-acetyl-3-hydroxy-2-propylphenoxy)-undeca-3(E),5(Z)-dien-2-yl-7-thio-4-oxo-4H-1-benzopyrane-2-carboxylic acid The title compound is prepared analogously to Example 2 from the corresponding methyl ester (Example 64); m.p. 216°-218°; $[\alpha]_D^{20}$ (chloroform, 0.258%) = 34.9° ± 3.9°; $[\alpha]_D^{20}$ 73.8° ± 6.3° (methanol, 0.160%); UV (methanol): $\lambda_{max}(\epsilon)$ = 219 (50140), 232 (sh), 266 (26120), 286 (22460) 320 (15600).

EXAMPLE 66

(1R,2S)-1-hydroxy-1-phenyl-8-(4-acetyl-3-hydroxy-2-propylphenoxy)-octa-3(E),5(Z)-dien-2-yl-7-thio-4-oxo-4H-1-benzopyrane-2-carboxylic acid methyl ester The title compound is prepared analogously to Example 1 from (1R,2R)-1,2-epoxy-1-phenyl-8-(4-acetyl-3-hydroxy-2-propylphenoxy)-octa-3(E),5(Z)-diene; light-yellow foam; $R_f$ = 0.41 (hexane/ethyl acetate = 1:1); $[\alpha]_D^{20}$ 47.3° ± 2.6° (chloroform, 0.385%).

The starting material is prepared, for example, as follows:

a) (1R,2R)-1,2-epoxy-1-phenyl-8-(4-acetyl-3-hydroxy-2-propylphenoxy)octa-3(E),5(Z)-diene The title compound is prepared analogously to Example 1d) from 3-(4-acetyl-3-hydroxy-2-propylphenoxy)-propyl-triphenylphosphonium bromide (Example 1c) and (4R,5R)-4,5-epoxy-5-phenyl-pent-2(E)-enal; light-yellow oil; $R_f$ = 0.60 (hexane/ethyl acetate = 3:2).

b) (4R,5R)-4,5-epoxy-5-phenyl-pent-2(E)-enal

The title compound is prepared analogously to Example 1b) from (2R,3R)-2,3-epoxy-3-phenyl-propanol; yellow oil which crystallises on standing; $R_f$ = 0.38 (hexane/ethyl acetate = 3:2); $[\alpha]_D^{20}$ = 185° ± 5.0° (chloroform, 0.200%).

c) (2R,3R)-2,3-epoxy-3-phenyl-propanol

The title compound is prepared analogously to Example 1a) from 3-phenyl-prop-2(E)-enol; colourless oil which crystallises at low temperature. $R_f$ = 0.49 (hexane/ethyl acetate = 1:1); IR (methylene chloride): 3590, 3040, 2980, 2920, 2870, 1605, 1080, 1070 cm$^{-1}$. $[\alpha]_D^{20}$ (chloroform, 0.279%) = 47.7° ± 3.6°.

EXAMPLE 67

Sodium salt of (1R,2S)-1-hydroxy-1-phenyl-8-(4-acetyl-3-hydroxy-2-propylphenoxy)-octa-3(E),5(Z)-dien-2-yl-7-thio-4-oxo-4H-1-benzopyrane-2-carboxylic acid The title compound is prepared analogously to Example 2 from the corresponding methyl ester (Example 66); m.p. 219°-221°; $[\alpha]_D^{20}$ (chloroform, 0.160%) = 103.1° ± 6.3°; UV (methanol): $\lambda_{max}(\epsilon)$ = 221 (51180), 232 (sh), 267 (27040), 284 (23840), 321 (16200); UV (chloroform): $\lambda_{max}(\epsilon)$ = 274 (26080), 286 (sh), 330 (sh).

EXAMPLE 68

(1R,2S)-1-hydroxy-1-(3-trifluoromethylphenyl)-8-(3-acetyl-4-hydroxy-5-propylphenoxy)-octa-3(E),5(Z)-dien-2-yl-7-thio-4-oxo-4H-1-benzopyrane-2-carboxylic acid methyl ester The title compound is prepared analogously to Example 1 from (1R,2R)-1,2-epoxy-1-(3-trifluoromethylphenyl)-8-(3-acetyl-4-hydroxy-5-propylphenoxy)-octa-3(E),5(Z)-diene; $R_f$ = 0.21 (hexane/ethyl acetate, 3:2).

The starting material is prepared, for example, as follows:

a) 3-(3-acetyl-4-hydroxy-5-propylphenoxy)-propyl bromide 6.2 g of potassium carbonate and 0.5 g of potassium iodide are added to a solution of 5.8 g of 2,5-dihydroxy-3-propyl-acetophenone and 6.1 ml of 1,3-dibromopropane in 60 ml of methyl ethyl ketone. The reaction mixture is heated at reflux for 24 hours, and then poured onto 300 ml of ice-water, rendered acidic with hydrochloric acid and extracted with dichloromethane (3 × 150 ml). The combined extracts are washed with 50 ml of water and dried over sodium sulfate. After filtration and concentration by evaporation in vacuo, the residue is chromatographed on 400 g of silica gel with dichloromethane. In the first fraction the title compound is eluted which, after concentration by evaporation, is obtained in the form of light-yellow crystals having a melting point of 69°-70°.

b) 3-(3-acetyl-4-hydroxy-5-propylphenoxy)-propyl-triphenylphosphonium bromide The title compound is prepared analogously to Example 1c) from 3-(3-acetyl-4-hydroxy-5-propylphenoxy)-propyl bromide and triphenylphosphine; m.p. 103°–105°.

c)
(1R,2R)-1,2-epoxy-1-(3-trifluoromethylphenyl)-8-(3-acetyl-4-hydroxy-5-propylphenoxy)-octa-3(E),5(Z)-diene The title compound is prepared analogously to Example 1d) from 3-(3-acetyl-4-hydroxy-5-propylphenoxy)-propyl-triphenylphosphonium bromide and (4R,5R)-4,5-epoxy-5-(3-trifluoromethylphenyl)-pent-2(E)-enal; $R_f$=0.54 (hexane/ethyl acetate 2:1).

EXAMPLE 69

Sodium salt of (1R,2S)-1-hydroxy-1-(3-trifluoromethylphenyl)-8-(3-acetyl-4-hydroxy-5-propylphenoxy)-octa-3(E),5(Z)-dien-2-yl-7-thio-4-oxo-4H-1-benzopyrane-2-carboxylic acid The title compound is prepared analogously to Example 2 from (1R,2S)-1-hydroxy-1-(3-trifluoromethylphenyl)-8-(3-acetyl-4-hydroxy-5-propylphenoxy)-octa-3(E),5(Z)-dien-2-yl-7-thio-4-oxo-4H-1-benzopyrane-2-carboxylic acid methyl ester; yellow foam; $^1$H-NMR (CD$_3$OD): δ=7.91, 7.76–7.56, 7.50, 7.36, 7.05, 6.82, 6.41, 6.00, 5.75, 5.47, 5.12, 4.45, 3.78, 2.65–2.35, 1.88, 1.58, 0.94 ppm.

EXAMPLE 70

(1R,2S)-1-hydroxy-1-(3-chlorophenyl)-8-(4-acetyl-3-hydroxy-2-propylphenoxy)-octa-3(E),5(Z)-dien-2-yl-7-thio-4-oxo-4H-1-benzopyrane-2-carboxylic acid methyl ester The title compound is prepared analogously to Example 1 from (1R,2R)-1,2-epoxy-1-(3-chlorophenyl)-8-(4-acetyl-3-hydroxy-2-propylphenoxy)octa-3(E),5(Z)-diene; m.p. 76°–77°; $[α]_D^{20}$ (chloroform, 0.215%)=51.2°±4.7°; UV (chloroform): $λ_{max}(ε)$=271 (28160), 285 (sh), 321 (15380).

The starting material is prepared, for example, as follows:

a)
(1R,2R)-1,2-epoxy-1-(3-chlorophenyl)-8-(4-acetyl-3-hydroxy-2-propylphenoxy)-octa-3(E),5(Z)-diene The title compound is prepared analogously to Example 1d) from 3-(4-acetyl-3-hydroxy-2-propylphenoxy)-propyl-triphenylphosphonium bromide (Example 1c) and (4R,5R)-4,5-epoxy-5-(3-chlorophenyl)-pent-2(E)-enal; light-yellow oil; $[α]_D^{20}$ (chloroform, 0.541%)=63.9°±1.8°.

b)
(4R,5R)-4,5-epoxy-5-(3-chlorophenyl)-pent-2(E)-enal

The title compound is prepared analogously to Example 1b) from (2R,3R)-2,3-epoxy-3-(3-chlorophenyl)-propanol; dark-yellow oil; $R_f$=0.23 (hexane/ethyl acetate=4:1). $[α]_D^{20}$ (chloroform, 0.30%)=184.7°±3.3.

c) (2R,3R)-2,3-epoxy-3-(3-chlorophenyl)-propanol

The title compound is prepared analogously to Example 1a) from 3-(3-chlorophenyl)-prop-2(E)-enol; light-yellow oil; $R_f$=0.22 (hexane/ethyl acetate=7:3). IR (methylene chloride): 3580, 3040, 2980, 2910, 2860, 1600, 1570, 1070 cm$^{-1}$. $[α]_D^{20}$ (chloroform, 0.334%)=47.3°±3.0°.

EXAMPLE 71

Sodium salt of (1R,2S)-1-hydroxy-1-(3-chlorophenyl)-8-(4-acetyl-3-hydroxy-2-propylphenoxy)-octa-3(E),5(Z)-dien-2-yl-7-thio-4-oxo-4H-1-benzopyrane-2-carboxylic acid The title compound is prepared analogously to Example 2 from the corresponding methyl ester (Example 70); m.p. 217°–219°; $[α]_D^{20}$ (methanol, 0.160%)=107.5°±6.3°; UV (methanol): $λ_{max}(ε)$=219 (55060), 235 (sh), 267 (27340), 284 (23920), 320 (16500).

EXAMPLE 72

(1R,2S)-1-hydroxy-1-(3-chlorophenyl)-10-(4-acetyl-3-hydroxy-2-propylphenoxy)-deca-3(E),5(Z)-dien-2-yl-7-thio-4-oxo-4H-1-benzopyrane-2-carboxylic acid methyl ester The title compound is prepared analogously to Example 1 from (1R,2R)-1,2-epoxy-1-(3-chlorophenyl)-10-(4-acetyl-3-hydroxy-2-propylphenoxy)-deca-3(E),5(Z)-diene; m.p. 61°–62°. $[α]_{D20}$ (chloroform, 0.170%)=52.9°±5.9°; UV (chloroform): $λ_{max}(ε)$=271 (27120), 286 (24800), 322 (15400).

The starting material is prepared, for example, as follows:

a)
(1R,2R)-1,2-epoxy-1-(3-chlorophenyl)-10-(4-acetyl-3-hydroxy-2-propylphenoxy)-deca-3(E),5(Z)-diene The title compound is prepared analogously to Example 1d) from 3-(4-acetyl-3-hydroxy-2-propylphenoxy)-pentyl-triphenylphosphonium bromide (Example 29a) and (4R,5R)-4,5-epoxy-5-(3-chlorophenyl)-pent-2(E)-enal (Example 70b); light-yellow oil; $[α]_D^{20}$ (chloroform, 0.391%)=61.4°±2.5°.

EXAMPLE 73

Sodium salt of (1R,2S)-1-hydroxy-1-(3-chlorophenyl)-10-(4-acetyl-3-hydroxy-2-propylphenoxy)-deca-3(E),5(Z)-dien-2-yl-7-thio-4-oxo-4H-1-benzopyrane-2-carboxylic acid The title compound is prepared analogously to Example 2 from the corresponding methyl ester (Example 72); m.p. 204°–206°; $[α]_D^{20}$ (methanol, 0.205%)=58.5°±4.9°; UV (MeOH): $λ_{max}(ε)$=218 (27940), 267 (13140), 285 (11600), 320 (sh).

EXAMPLE 74

(1R,2S)-1-hydroxy-1-(3-methoxyphenyl)-8-(4-acetyl-3-hydroxy-2-propylphenoxy)-octa-3(E),5(Z)-dien-2-yl-7-thio-4-oxo-4H-1-benzopyrane-2-carboxylic acid methyl ester The title compound is prepared analogously to Example 1 from (1R,2R)-1,2-epoxy-1-(3-methoxyphenyl)-8-(4-acetyl-3-hydroxy-2-propylphenoxy)octa-3(E),5(Z)-diene; m.p. 65°–67°; UV (chloroform): $λ_{max}(c)$=271 (30360), 285 (sh), 323 (16600).

The starting material is prepared, for example, as follows:

a)
(1R,2R)-1,2-epoxy-1-(3-methoxyphenyl)-8-(4-acetyl-3-hydroxy-2-propylphenoxy)-octa-3(E),5(Z)-diene The title compound is prepared analogously to Example 1d) from 3-(4-acetyl-3-hydroxy-2-propylphenoxy)-propyl-triphenylphosphonium bromide (Example 1c) and (4R,5R)-4,5-epoxy-5-(3-methoxyphenyl)-pent-2(E)-enal; light-yellow oil; $[\alpha]_D^{20}$ (chloroform, 0.315%)=78.4±3.2.

b)
(4R,5R)-4,5-epoxy-5-(3-methoxyphenyl)-pent-2(E)-enal

The title compound is prepared analogously to Example 1b) from (2R,3R)-2,3-epoxy-3-(3-methoxyphenyl)-propanol; yellow oil; $R_f$=0.41 (hexane/ethyl acetate=3:2); $[\alpha]_D^{20}$ (chloroform, 0.567%)=168.9°±1.8°.

c) (2R,3R)-2,3-epoxy-3-(3-methoxyphenyl)-propanol

The title compound is prepared analogously to Example 1a) from 3-(3-methoxyphenyl)-prop-2(E)-enol; light-yellow oil; $R_f$=0.31 (hexane/ethyl acetate=3:2). IR (methylene chloride): 3550, 2890, 1580, 1565, 1465, 1445, 1130 cm$^{-1}$.

EXAMPLE 75

Sodium salt of (1R,2S)-1-hydroxy-1-(3-methoxyphenyl)-8-(4-acetyl-3-hydroxy-2-propylphenoxy)-octa-3(E),5(Z)-dien-2-yl-7-thio-4-oxo-4H-1-benzopyrane-2-carboxylic acid The title compound is prepared analogously to Example 2 from the corresponding methyl ester (Example 74); m.p. 206°–208°; $[\alpha]_D^{20}$ (methanol, 0.293%)=99.7°±3.4°; UV (methanol): $\lambda_{max}(\epsilon)$=221 (57840), 235 (sh), 268 (29360), 282 (26400), 320 (16800).

EXAMPLE 76

(1R,2S)-1-hydroxy-1-(3-methoxyphenyl)-10-(4-acetyl-3-hydroxy-2-propylphenoxy)-deca-3(E),5(Z)-dien-2-yl-7-thio-4-oxo-4H-1-benzopyrane-2-carboxylic acid methyl ester The title compound is prepared analogously to Example 1 from (1R,2R)-1,2-epoxy-1-(3-methoxyphenyl)-10-(4-acetyl-3-hydroxy-2-propylphenoxy)deca-3(E),5(Z)-diene; m.p. 53° (partly sublimes); UV (chloroform): $\lambda_{max}(\epsilon)$=272 (29920), 285 (sh), 323 (15540); $[\alpha]_D^{20}$ (chloroform, 0.180%)=44.4°±5.6°.

The starting material is prepared, for example, as follows:

a)
(1R,2R)-1,2-epoxy-1-(3-methoxyphenyl)-10-(4-acetyl-3-hydroxy-2-propylphenoxy)-deca-3(E),5(Z)-diene The title compound is prepared analogously to Example 1d) from 3-(4-acetyl-3-hydroxy-2-propylphenoxy)-pentyl-triphenylphosphonium bromide (Example 29a) and (4R,5R)-4,5-epoxy-5-(3-methoxyphenyl)-pent-2(E)-enal (Example 74b); light-yellow oil; $[\alpha]_D$(-chloroform, 0.375%)=72.5±2.7.

EXAMPLE 77

Sodium salt of (1R,2S)-1-hydroxy-1-(3-methoxyphenyl)-10-(4-acetyl-3-hydroxy-2-propylphenoxy)-deca-3(E),5(Z)-dien-2-yl-7-thio-4-oxo-4H-1-benzopyrane-2-carboxylic acid The title compound is prepared analogously to Example 2 from the corresponding methyl ester (Example 76); m.p. 187°–188°; $[\alpha]_D^{20}$ (methanol, 0.150%)=72.0°±6.7°; UV (methanol): $\lambda_{max}(\epsilon)$=222 (55780), 268 (27820), 282 (25200), 321 (16200).

EXAMPLE 78

(1R,2S)-1-hydroxy-1-(3-trifluoromethylphenyl)-8-(4-trifluoroacetyl-3-hydroxyphenoxy)-octa-3(E),5(Z)-dien-2-yl-7-thio-4-oxo-4H-1-benzopyrane-2-carboxylic acid methyl ester The title compound is prepared analogously to Example 1 from (1R,2R)-1,2-epoxy-(3-trifluoromethylphenyl)-8-(4-trifluoroacetyl-3-hydroxyphenoxy)-octa-3(E),5(Z)-diene; $R_f$=0.23 (hexane/ethyl acetate 3:2). The starting material is prepared, for example, as follows:

a) 3-(4-trifluoroacetyl-3-hydroxyphenoxy)-propyl bromide

The title compound is prepared analogously to Example 68a) from 2,4-dihydroxytrifluoroacetophenone and is obtained in the form of a light-yellow oil; IR (dichloromethane): 3150, 2940, 1645, 1625, 1380, 1210, 1150, 1125, 1020, 940 cm$^{-1}$.

b)
3-(4-trifluoroacetyl-3-hydroxyphenoxy)-propyl-triphenylphosphonium bromide

The title compound is prepared analogously to Example 1c) from 3-(4-trifluoroacetyl-3-hydroxyphenoxy)-propyl bromide and triphenylphosphine; m.p. 125°–130° C.

c)
(1R,2R)-1,2-epoxy-1-(3-trifluoromethylphenyl)-8-(4-trifluoroacetyl-3-hydroxyphenoxy)-octa-3(E),5(Z)-diene The title compound is prepared analogously to Example 1d) from 3-(4-trifluoroacetyl-3-hydroxyphenoxy)-propyl-triphenylphosphonium bromide and (4R,5R)-4,5-epoxy-5-(3-trifluoromethylphenyl)-pent-2(E)enal; $R_f$=0.56 (hexane/ethyl acetate 2:1).

EXAMPLE 79

Sodium salt of (1R,2S)-1-hydroxy-1-(3-trifluoromethylphenyl)-8-(4-trifluoroacetyl-3-hydroxyphenoxy)-octa-3(E),5(Z)-dien-2-yl-7-thio-4-oxo-4H-1-benzopyrane-2-carboxylic acid 10 ml of 0.1N aqueous sodium hydroxide solution are added to a solution, cooled to 10° C., of 708 mg of the methyl ester of the title compound (see Example 78) in 25 ml of tetrahydrofuran. The reaction mixture is stirred at room temperature for 24 hours, freed of solvent in vacuo and the residue is taken up in water. After filtration until clear, the solution is lyophilised. The title compound is obtained in the form of an olive-green amorphous powder. $^1$H-NMR (CD$_3$OD):± =7.94, 7.78–7.46, 7.36, 6.90, 6.36, 6.04, 5.74, 5.42, 5.12, 4.42, 3.86 ppm.

EXAMPLE 80

(1R,2S)-1-hydroxy-1-(3-trifluoromethylphenyl)-8-(4-trifluoroacetyl-3-hydroxy-2-propylphenoxy)-octa-3(E),5(Z)dien-2-yl-7-thio-4-oxo-4H-1-benzopyrane-2-carboxylic acid methyl ester The title compound is prepared analogously to Example 1 from (1R,2R)-1,2-epoxy-1-(3-trifluoromethylphenyl)-8-(4-trifluoroacetyl-3-hydroxy-2-propylphenoxy)-octa-3(E),5(Z)-diene; $R_f$=0.18 (toluene/ethyl acetate 5:1). The starting material is prepared, for example, as follows:

a)

3-(4-trifluoroacetyl-3-hydroxy-2-propylphenoxy)-propyl bromide

The title compound is prepared analogously to Example 68a) from 2,4-dihydroxy-3-propyl-trifluoroacetophenone and is obtained in the form of a yellow oil; IR (dichloromethane): 3150, 2950, 2860, 1640, 1620, 1500, 1295, 1210, 1150, 1120, 1070 cm$^{-1}$.

b)

3-(4-trifluoroacetyl-3-hydroxy-2-propylphenoxy)-propyl-triphenylphosphonium bromide The title compound is prepared analogously to Example 1c) from 3-(4-trifluoroacetyl-3-hydroxy-2-propylphenoxy)-propyl bromide and triphenylphosphine; m.p. 170°-190° C.

c)

(1R,2R)-1,2-epoxy-1-(3-trifluoromethylphenyl)-8-(4-trifluoroacetyl-3-hydroxy-2-propylphenoxy)-octa-3(E),5(Z)-diene The title compound is prepared analogously to Example 1d) from 3-(4-trifluoroacetyl-3-hydroxy-2-propylphenoxy)-propyl-triphenylphosphonium bromide and (4R,5R)-4,5-epoxy-5-(3-trifluoromethylphenyl)-pent-2(E)enal; R$_f$=0.55 (hexane/ethyl acetate 2:1).

EXAMPLE 81

Sodium salt of (1R,2S)-1-hydroxy-1-(3-trifluoromethylphenyl)-8-(4-trifluoroacetyl-3-hydroxy-2-propylphenoxy)-octa-3(E),5(Z)-dien-2-yl-7-thio-4-oxo-4H-1-benzopyrane-2-carboxylic acid 6.6 ml of 0.1N aqueous sodium hydroxide solution are added to a solution, cooled to 10° C., of 500 mg of the methyl ester of the title compound (see Example 80) in 20 ml of tetrahydrofuran. The reaction mixture is stirred for 1 hour at 10° C., freed of tetrahydrofuran in vacuo and the solution that remains is lyophilised. The title compound is obtained in the form of a yellowish-green amorphous powder; $^1$H-NMR (CD$_3$OD): δ=7.93, 7.77-7.60, 7.50, 7.36, 6.92, 6.43, 6.04, 5.73, 5.47, 5.13, 4.47, 4.00, 2.50, 2.38, 0.72 ppm.

EXAMPLE 82

(1R,2S)-1-hydroxy-1-(3-trifluoromethylphenyl)-8-(4-acetyl-3-hydroxy-2-propylphenylthio)-octa-3(E),5(Z)-dien-2-yl-7-thio-4-oxo-4H-benzopyrane-2-carboxylic acid methyl ester The title compound is prepared analogously to Example 1 from (1R,2S)-1,2-epoxy-1-(3-trifluoromethylphenyl)-8-(4-acetyl-3-hydroxy-2-propylphenylthio)-octa-3(E),5(Z)-diene; R$_f$=0.19 (hexane/ethyl acetate 3:2). The starting material is prepared, for example, as follows:

a) 3-(4-acetyl-3-hydroxy-2-propylphenylthio)-propyl bromide

The title compound is prepared analogously to Example 68a) from 2-hydroxy-4-mercapto-acetophenone; light-yellow oil.

b)

3-(4-acetyl-3-hydroxy-2-propylphenylthio)-propyl-triphenylphosphonium bromide

The title compound is prepared analogously to Example 1 from 3-(4-acetyl-3-hydroxy-2-propylphenylthio)-propyl bromide and triphenylphosphine.

c)

(1R,2S)-1,2-epoxy-1-(3-trifluoromethylphenyl)-8-(4-acetyl-3-hydroxy-2-propylphenylthio)-octa-3(E),5(Z)-diene The title compound is prepared analogously to Example 1d) from 3-(4-acetyl-3-hydroxy-2-propylphenylthio)-propyl-triphenylphosphonium bromide and (4R,5R)-4,5-epoxy-5-(3-trifluoromethylphenyl)-pent-2(E)enal.

EXAMPLE 83

Sodium salt of (1R,2S)-1-hydroxy-1-(3-trifluoromethylphenyl)-8-(4-acetyl-3-hydroxy-2-propylphenylthio)-octa-3(E),5(Z)-dien-2-yl-7-thio-4-oxo-4H-benzopyrane-2-carboxylic acid The title compound is prepared analogously to Example 2 from the corresponding methyl ester (Example 82).

EXAMPLE 84

(1R,1S)-1-hydroxy-1-(3-trifluoromethylphenyl)-10-(4-acetyl-3-hydroxy-2-propylphenylthio)-deca-3(E),5(Z)-dien-2-yl-7-thio-4-oxo-4H-benzopyrane-2-carboxylic acid methyl ester The title compound is prepared analogously to Example 1 from (1R,2S)-1,2-epoxy-1-(3-trifluoromethylphenyl)-10-(4-acetyl-3-hydroxy-2-propylphenylthio)-deca-3(E),5(Z)-diene; R$_f$=0.17 (hexane/ethyl acetate 3:2). The starting material can be prepared, for example, as follows:

a) 5-(4-acetyl-3-hydroxy-2-propylphenylthio)-pentyl bromide

The title compound is prepared analogously to Example 68a) from 2-hydroxy-4-mercapto-acetophenone; light-yellow oil.

b)

5-(4-acetyl-3-hydroxy-2-propylphenylthio)-pentyl-triphenylphosphonium bromide

The title compound is prepared analogously to Example 1 from 5-(4-acetyl-3-hydroxy-2-propylphenylthio)-pentyl bromide and triphenylphosphine.

c)

(1R,1S)-1,2-epoxy-1-(3-trifluoromethylphenyl)-10-(4-acetyl-3-hydroxy-2-propylphenylthio)-deca-3(E),5(Z)-diene The title compound is prepared analogously to Example 1d) from 5-(4-acetyl-3-hydroxy-2-propylphenylthio)-pentyl-triphenylphosphonium bromide and (4R,5R)-4,5-epoxy-5-(3-trifluoromethylphenyl)-pent-2(E)enol.

EXAMPLE 85

Sodium salt of
(1R,1S)-1-hydroxy-1-(3-trifluoromethylphenyl)-10-(4-acetyl-3-hydroxy-2-propylphenylthio)-deca-3(E),5(Z)-dien-2-yl-7-thio-4-oxo-4H-benzopyrane-2-carboxylic acid The title compound is prepared analogously to Example 2 from the corresponding methyl ester (Example 84).

EXAMPLE 86

(5R,6S)-1,1,1-trifluoro-5-hydroxy-12-(4-acetyl-3-hydroxy-2-propylphenoxy)-dodeca-7(E),9(Z)-dien-6-yl-7-thio-4-oxo-4H-1-benzopyrane-2-carboxylic acid methyl ester The title compound is prepared analogously to Example 1 from (5R,6R)-5,6-epoxy-1,1,1-trifluoro-12-(4-acetyl-3-hydroxy-2-propylphenoxy)dodeca-7(E),9(Z)-diene; light-yellow foam; $R_f=0.24$ (hexane/ethyl acetate=3:2).

The starting material is prepared, for example, as follows:

a) (2R,3R)-2,3-epoxy-7,7,7-trifluoro-heptanol

The title compound is prepared analogously to Example 1a) from 7,7,7-trifluoro-hept-2(E)-enol; light-yellow oil; $R_f=0.38$ (hexane/ethyl acetate=3:2). $[\alpha]_D^{20}$ (chloroform, 0.490%)=15.3°±2.0°. IR (methylene chloride): 3550, 3430, 2900, 1180, 1125 cm$^{-1}$.

b) (4R,5R)-4,5-epoxy-9,9,9-trifluoro-non-2(E)-enal

The title compound is prepared analogously to Example 1b) from (2R,3R)-2,3-epoxy-7,7,7-trifluoro-heptanol; oil, which crystallises in the refrigerator. $R_f=0.63$ (hexane/ethyl acetate=1:1). $[\alpha]_D^{20}$ (chloroform, 0.210%)=19.5°±4.8°.

c) (5R,6R)-5,6-epoxy-1,1,1-trifluoro-12-(4-acetyl-3-hydroxy-2-propylphenoxy)-dodeca-7(E),9(Z)-diene The title compound is prepared analogously to Example 1d) from 3-(4-acetyl-3-hydroxy-2-propylphenoxy)-propyltriphenylphosphonium bromide (Example 1c) and (4R,5R)-4,5-epoxy-9,9,9-trifluoro-non-2(E)enal; yellow oil; $R_f=0.56$ (hexane/ethyl acetate=3:2).

EXAMPLE 87

Sodium salt of
(5R,6S)-1,1,1-trifluoro-5-hydroxy-12-(4-acetyl-3-hydroxy-2-propylphenoxy)-dodeca-7(E),9(Z)-dien-6-yl-7-thio-4-oxo-4H-1-benzopyrane-2-carboxylic acid The title compound is prepared analogously to Example 2 from the corresponding methyl ester (Example 86); m.p. 190°-191°; $[\alpha]_D^{20}$ (methanol, 0.268%)=105.2°±3.7°; UV (methanol): $\lambda_{max}(\epsilon)=222$ (48800), 235 (sh), 267 (25920), 285 (22920), 320 (16000).

EXAMPLE 88

(4R,5S)-1,1,1-trifluoro-4-hydroxy-13-(4-acetyl-3-hydroxy-2-propylphenoxy)-trideca-6(E),8(Z)-dien-5-yl-7-thio-4-oxo-4H-benzopyrane-2-carboxylic acid methyl ester The title compound is prepared analogously to Example 1 from (4R,5R)-4,5-epoxy-1,1,1-trifluoro-13-(4-acetyl-3-hydroxy-2-propylphenoxy)-trideca-6(E),8(Z)-diene; yellow oil. The starting material is prepared, for example, as follows:

a) (4R,5R)-4,5-epoxy-8,8,8-trifluoro-oct-2(E)-enal

The title compound is prepared analogously to Example 1b) from (2R,3R)-2,3-epoxy-6,6,6-trifluoro-hexanol; light-yellow oil which crystallises in the refrigerator; $R_f=0.53$ (hexane/ethyl acetate=3:2). $[\alpha]_D^{20}$ (chloroform, 0.290%)=21.7°±3.4°. IR (methylene chloride): 3050, 2980, 2930, 2810, 2730, 1690, 1640, 1145 cm$^{-1}$.

b) (4R,5R)-4,5-epoxy-1,1,1-trifluoro-13-(4-acetyl-3-hydroxy-2-propylphenoxy)-trideca-6(E),8(Z)-diene The title compound is prepared analogously to Example 1d) from 3-(4-acetyl-3-hydroxy-2-propylphenoxy)-pentyl-triphenylphosphonium bromide (Example 29a) and (4R,5R)-4,5-epoxy-8,8,8-trifluoro-oct-2(E)-enal; yellow oil; $R_f=0.69$ (hexane/ethyl acetate=3:2).

EXAMPLE 89

Sodium salt of
(4R,5R)-1,1,1-trifluoro-4-hydroxy-13-(4-acetyl-3-hydroxy-2-propylphenoxy)-trideca-6(E),8(Z)-dien-5-yl-7-thio-4-oxo-4H-1-benzopyrane-2-carboxylic acid The title compound is prepared analogously to Example 2 from the corresponding methyl ester (Example 88); m.p. 150°-152°; $[\alpha]_D^{20}$ (methanol, 0.265%)=72.5°±3.8°; UV (methanol): $\lambda_{max}(\epsilon)=221$ (44680), 231 (sh), 266 (22560), 285 (20560), 330 (sh).

EXAMPLE 90

(4R,5S)-1,1,1-trifluoro-4-hydroxy-13-(4-acetyl-3-hydroxy-2-propylphenoxy)-dodeca-6(E),8(Z)-dien-5-yl-7-thio-4-oxo-4H-1-benzopyrane-2-carboxylic acid methyl ester The title compound is prepared analogously to Example 1 from (4R,5R)-4,5-epoxy-1,1,1-trifluoro-12-(4-acetyl-3-hydroxy-2-propylphenoxy)dodeca-6(E),8(Z)-diene; yellow oil; $R_f=0.31$ (hexane/ethyl acetate=3:2). The starting material is prepared, for example, as follows:

a) (4R,5R)-4,5-epoxy-1,1,1-trifluoro-12-(4-acetyl-3-hydroxy-2-propylphenoxy)-dodeca-6(E),8(Z)-diene The title compound is prepared analogously to Example 1d) from 3-(4-acetyl-3-hydroxy-2-propylphenoxy)-butyl-triphenylphosphonium bromide (Example 62b) and (4R,5R)-4,5-epoxy-8,8,8-trifluoro-oct-2(E)enal (Example 86b); yellow oil; $R_f=0.64$ (hexane/ethyl acetate=3:2).

EXAMPLE 91

Sodium salt of
(4R,5S)-1,1,1-trifluoro-4-hydroxy-12-(4-acetyl-3-hydroxy-2-propylphenoxy)-dodeca-6(E),8(Z)-dien-5-yl-7-thio-4-oxo-4H-1-benzopyrane-2-carboxylic acid The title compound is prepared analogously to Example 2 from the corresponding methyl ester (Example 90); m.p. 180°-182°; $[\alpha]_D^{20}$ (methanol, 0.292%)=77.1°±3.4°; UV (methanol): $\lambda_{max}(\epsilon)=222$ (47480), 231 (sh), 267 (24840), 285 (22120), 321 (15800).

EXAMPLE 92

(5R,6S)-5-hydroxy-12-(4-acetyl-3-hydroxy-2-propyl-phenoxy)dodeca-7(E),9(Z)-dien-5-yl-7-thio-4-oxo-4H-1-benzopyrane-2-carboxylic acid methyl ester The title compound is prepared analogously to Example 1 from (5R,6R)-5,6-epoxy-12-(4-acetyl-3-hydroxy-2-propylphenoxy)-dodeca-7(E),9(Z)diene; light-yellow foam; $R_f$=0.43 (hexane/ethyl acetate=1:1); $[\alpha]_D^{20}$ (methanol, 0.150%)=22.0°±6.7°; IR (methylene chloride): 3580, 2950, 1745, 1655, 1625, 1600 cm$^{-1}$. The starting material is prepared, for example, as follows:

a) (4R,5R)-4,5-epoxy-non-2(E)-enal

The title compound is prepared analogously to Example 1b) from (2R,3R)-2,3-epoxy-heptanol; yellow oil; $R_f$=0.29 (hexane/ethyl acetate =4:1); $[\alpha]_D^{20}$ (chloroform, 0.390%)=21.3°±2.6°; IR (methylene chloride): 2950, 2920, 2860, 1690, 1640, 1100, 970 cm$^{-1}$.

b) (5R,6R)-5,6-epoxy-12-(4-acetyl-3-hydroxy-2-propyl-phenoxy)-dodeca-7(E),9(Z)-diene The title compound is prepared analogously to Example 1d) from 3-(4-acetyl-3-hydroxy-2-propylphenoxy)-propyl-triphenylphosphonium bromide (Example 1c) and (4R,5R)-4,5-epoxy-non-2(E)-enal; light-yellow oil; $[\alpha]_D^{20}$ (chloroform, 0.650%)=23.7°±1.5°.

EXAMPLE 93

Sodium salt of (5R,6S)-5-hydroxy-12-(4-acetyl-3-hydroxy-2-propyl-phenoxy)-dodeca-7(E),9(Z)-dien-6-yl-7-thio-4-oxo-4H-1-benzopyrane-3-carboxylic acid The title compound is prepared analogously to Example 2 from the corresponding methyl ester (Example 92); m.p. 205°-207°; $[\alpha]_D^{20}$ (methanol, 0.278%)=115.1°±3.6°; UV (methanol): $\lambda_{max}(\epsilon)$=222 (50960), 232 (sh), 267 (27400), 285 (24000), 321 (16400).

EXAMPLE 94

(5R,6S)-5-hydroxy-12-(4-acetyl-3-hydroxy-2-propyl-phenoxy)dodeca-7(E),9(Z)-dien-6-yl-7-thio-4-oxo-4H-1-benzopyrane-2-carboxylic acid methyl ester The title compound is prepared analogously to Example 1 from (5S,6S)-5,6-epoxy-12-(4-acetyl-3-hydroxy-2-propylphenoxy)-dodeca-7(E),9(Z)-diene; colourless foam; $[\alpha]_D^{20}$ (methanol, 0.260%)=136.2°±3.8°; UV (methanol): $\lambda_{max}(\epsilon)$=221 (48040), 271 (28320), 327 (13200). The starting material is prepared, for example, as follows:

a) (4S,5S)-4,5-epoxy-non-2(E)-enal

The title compound is prepared analogously to Example 1b) from (2S,3S)-2,3-epoxy-heptanol; yellow oil; $R_f$=0.27 (hexane/ethyl acetate=5:1); $[\alpha]_D^{20}$ (chloroform, 0.325%)=23.1°±3.0°.

b) (5S,6S)-5,6-epoxy-12-(4-acetyl-3-hydroxy-2-propyl-phenoxy)-dodeca-7(E),9(Z)-diene The title compound is prepared analogously to Example 1d) from 3-(4-acetyl-3-hydroxy-2-propylphenoxy)-propyltriphenylphosphonium bromide (Example 1c) and (4S,5S)-4,5-epoxy-non-2(E)-enal; light-yellow oil; $[\alpha]_D^{20}$ (chloroform, 0.600%)=24.8°±1.6°.

EXAMPLE 95

Sodium salt of (5S,6R)-5-hydroxy-12-(4-acetyl-3-hydroxy-2-propyl-phenoxy)-dodeca-7(E),9(Z)-dien-6-yl-7-thio-4-oxo-4H-1-benzopyrane-2-carboxylic acid The title compound is prepared analogously to Example 2 from the corresponding methyl ester (Example 94); m.p. 204°-206°; $[\alpha]_D^{20}$ (methanol, 0.570%)=121.1°±1.8°; UV (methanol): $\lambda_{max}(\epsilon)$=222 (51240), 235 (sh), 267 (27360), 284 (21400), 320 (16400).

EXAMPLE 96

(5R,6S)-5-hydroxy-14-(4-acetyl-3-hydroxy-2-propyl-phenoxy)tetradeca-7(E),9(Z)-dien-6-yl-7-thio-4-oxo-4H-1-benzopyrane-2-carboxylic acid methyl ester The title compound is prepared analogously to Example 1 from (5R,6R)-5,6-epoxy-14-(4-acetyl-3-hydroxy-2-propylphenoxy)-tetradeca-7(E),9(Z)-diene; light-yellow viscous oil; $[\alpha]_D^{20}$ (chloroform, 0.424%)=66.5°±2.4°; UV (chloroform): $\lambda_{max}(\epsilon)$=270 (28560), 288 (sh), 325 (15240). The starting material is prepared, for example, as follows:

a) (5R,6R)-5,6-epoxy-14-(4-acetyl-3-hydroxy-2-propyl-phenoxy)-tetradeca-7(E),9(Z)-diene The title compound is prepared analogously to Example 1d) from 3-(4-acetyl-3-hydroxy-2-propylphenoxy)-pentyl-triphenylphosphonium bromide (Example 29a) and (4R,5R)-4,5-epoxy-non-2(E)-enal (Example 92a); light-yellow oil; $[\alpha]_D^{20}$ (chloroform, 0.441%)=20.6°±2.3°.

EXAMPLE 97

Sodium salt of (5R,6S)-5-hydroxy-14-(4-acetyl-3-hydroxy-2-propyl-phenoxy)-tetradeca-7(E),9(Z)-dien-6-yl-7-thio-4-oxo-4H-1-benzopyrane-2-carboxylic acid The title compound is prepared analogously to Example 2 from the corresponding methyl ester (Example 96); m.p. 193°-195°; $[\alpha]_D^{20}$ (methanol, 0.284%)=71.1°±3.5°. UV (methanol): $\lambda_{max}(\epsilon)$=222 (49320), 232 (sh), 267 (25520), 286 (22680), 321 (16000).

EXAMPLE 98

(5S,6R)-5-hydroxy-14-(4-acetyl-3-hydroxy-2-propyl-phenoxy)-tetradeca-7(E),9(Z)-dien-6-yl-7-thio-4-oxo-4H-1-benzopyrane-2-carboxylic acid methyl ester The title compound is prepared analogously to Example 1 from (5S,6S)-5,6-epoxy-14-(4-acetyl-3-hydroxy-2-propylphenoxy)-tetradeca-7(E),9(Z)-diene; light-yellow viscous mass; $[\alpha]_D^{20}$ (chloroform, 0.463%)=79.0°±2.2°; UV (chloroform): $\lambda_{max}(\epsilon)$=270 (27120), 288 (sh), 326 (14960). The starting material is prepared, for example, as follows:

a) (5S,6S)-5,6-epoxy-14-(4-acetyl-3-hydroxy-2-propyl-phenoxy)-tetradeca-7(E),9(Z)-diene The title compound is prepared analogously to Example 1d) from 3-(4-acetyl-3-hydroxy-2-propylphenoxy)-pentyl-triphenylphosphonium bromide (Example 29a) and (4S,5S)-4,5-epoxy-non-2(E)-enal (Example 94a); light-yellow oil; $[\alpha]_D^{20}$ (chloroform, 0.472%) = 18.8°±2.1°.

EXAMPLE 99

Sodium salt of (5S,6R)-5-hydroxy-14-(4-acetyl-3-hydroxy-2-propylphenoxy)-tetradeca-7(E),9(Z)-dien-6-yl-7-thio-4-oxo-4H-1-benzopyrane-2-carboxylic acid The title compound is prepared analogously to Example 2 from the corresponding methyl ester (Example 98); m.p. 193°-195°; $[\alpha]_D^{20}$ (methanol, 0.296%) = 65.9°±3.4°. UV (methanol): $\lambda_{max}(\epsilon) = 222$ (49760), 232 (sh), 267 (25800), 285 (22520), 320 (16000).

EXAMPLE 100

(5R,6S)-1,1,1-trifluoro-5-hydroxy-14-(4-acetyl-3-hydroxy-2-propylphenoxy)-tetradeca-7(E),9(Z)-dien-6-yl-7-thio-4- oxo-4H-1-benzopyrane-2-carboxylic acid methyl ester The title compound is prepared analogously to Example 1 from (5R,6R)-5,6-epoxy-1,1,1-trifluoro-14-(4-acetyl-3-hydroxy-2-propylphenoxy)-tetradeca-7(E),9(Z)-diene; light-yellow oil; $R_f = 0.32$ (hexane/ethyl acetate = 3:2).

The starting material is prepared, for example, as follows:

a) (5R,6R)-5,6-epoxy-1,1,1-trifluoro-14-(4-acetyl-3-hydroxy-2-propylphenoxy)-tetradeca-7(E),9(Z)-diene The title compound is prepared analogously to Example 1d) from 3-(4-acetyl-3-hydroxy-2-propylphenoxy)-pentyl-triphenylphosphonium bromide (Example 29a) and (4R,5R)-4,5-epoxy-9,9,9-trifluoro-2(E)-enal (Example 86a); yellow oil; $R_f = 0.72$ (hexane/ethyl acetate = 3:2).

EXAMPLE 101

Sodium salt of (5R,6S)-1,1,1-trifluoro-5-hydroxy-14-(4-acetyl-3-hydroxy-2-propylphenoxy)-tetradeca-7(E),9(Z)-dien-6-yl-7-thio-4-oxo-4H-1-benzopyrane-2-carboxylic acid The title compound is prepared analogously to Example 2 from the corresponding methyl ester (Example 100); UV (methanol): $\lambda_{max}(\epsilon) = 222$ (48800), 235 (sh), 267 (25920), 285 (22920), 320 (16000).

EXAMPLE 102

7-[(6R,7S)-15-(4-Acetyl-3-hydroxy-2-propylphenoxy)-1,1,1,2,2-pentafluoro-6-hydroxy-pentadeca-8(E),10(Z)-dien-7-ylthio]-4-oxo-4H-1-benzopyrane-2-carboxylic acid methyl ester A solution of 1.49 g of (6R,7S)-15-(4-acetyl-3-hydroxy-2-propyl-phenoxy)-6,7-epoxy-1,1,1,2,2-pentafluoropentadeca-8(E),10(Z)-diene in 100 ml of absolute methanol is stirred under argon with 3.3 ml of triethylamine and 1.05 g of 7-mercaptochromone-2-carboxylic acid methyl ester for 20 hours at room temperature and then concentrated by evaporation. The residue is dissolved in ethyl acetate and filtered over silica gel. The filtrate is washed with 25 ml of 1N hydrochloric acid and then four times using 25 ml of saturated sodium chloride solution each time, dried over sodium sulfate and concentrated by evaporation. Purification of the residue by chromatography on silica gel with hexane/ethyl acetate (3:2) as eluant yields the title compound in the form of a light-yellow foam; m.p.: 48°-49° C.; $R_f$ (hexane:-ethyl acetate 3:2): = 0.33; $[\alpha]_D^{20}$ (CHCl$_3$, 0.230%) = 67.4±4.3.; UV spectrum (CHCl$_3$): $\lambda_{max}$ ($\epsilon$) = 271 (25120), 285 (22080), 324 (14000). The starting materials are prepared as follows:

a) 5,5,5,4,4-Pentafluoro-1-pentene

Method A: In a 1 liter capacity three-necked flask having a dry ice cooler and a gas introduction tube, 39.5 g (160 mmol) of gaseous pentafluoroethyl iodide are introduced at 20° within a period of 20 minutes into a suspension of 20.2 g (180 mmol) of activated cadmium powder in 100 ml of dry dimethylformamide. After an induction period of 5 minutes a strongly exothermic reaction begins. The reaction mixture is stirred at room temperature for 1 hour and then filtered over filter flocks under nitrogen. The light-green organocadmium solution is then transmetallated at 0 with 17.2 g (120 mmol) of copper(I) bromide in 100 ml of dry hexamethylphosphoric acid triamide. After stirring for 10 minutes at 0, 12.1 g (100 mmol) of allyl bromide are added dropwise within a period of 15 minutes and the mixture is stirred for 2 hours at 25°. 250 ml of cold 1N hydrochloric acid are then added to the cloudy reaction solution. The product is distilled directly from the reaction flask via a Vigreux column. The title compound distils over in the form of a colourless liquid at b.p. 42°-44° C. $^1$H-NMR spectrum (CDCl$_3$; 300 MHz): 5.33 (br.s; 1H); 5.28 (m; 1H), 5.81 (t x d x q; J 16.1; 7.0; $\approx$1; 1H), 2.89 (t x d x q; J 17.2; 7.0; $\approx$0.5; 2H).

Method B: As described under method A, 39.5 g (160 mmol) of pentafluoroethyl iodide are introduced under inert conditions over a period of 20 minutes at room temperature into a suspension of 11.8 g (180 mmol) of activated zinc dust and 160 ml of dimethoxyethane. After approximately 5 minutes, a strongly exothermic reaction begins and a yellowish green suspension is formed. The reaction mixture is stirred for 1 hour at 25° and then filtered under inert conditions. There are then added to the light-green filtrate first 18.6 g (160 mmol) of N,N,N',N'-tetramethylethylenediamine, then, at 0., 17.2 g (120 mmol) of copper(I) bromide followed by 12.1 g (100 mmol) of allyl bromide. After stirring for 5 hours at 50., the reaction solution is mixed at room temperature with 250 ml of 1N hydrochloric acid and the product is distilled off directly from the reaction vessel. The title compound distils over in the form of a colourless liquid at b.p. 41°-45° C.

b) 6,6,6,5,5-Pentafluoro-hexan-1-al

In a pressurised autoclave, 1.3 g (3.8 mmol) of dicobalt octacarbonyl are dissolved under inert conditions in 50 ml of absolute benzene. Then, at −50°, 29.0 g (180 mmol) of 5,5,5,4,4-pentafluoro-1-pentene are added and, in each case at 60 bar, carbon monoxide and hydrogen are introduced under pressure until saturation point is reached. The reaction mixture is heated to 100° and maintained at that temperature and at a pressure of 160 bar for 5 hours. The reaction mixture is then cooled and 10 ml (~20 mmol) of the violet solution are subjected to fractional distillation. The boiling point of the thermolabile and air-sensitive aldehyde is 92°-93° (120 mbar), $^1$H-NMR spectrum (CDCl$_3$; 300 MHz): 9.77 (s: 1H); 2.61 (t; J 7.0; 2H); 2.19 (m; 2H), 1.91 (quint; J 7.0; 2H).

c) 8,8,8,7,7-Pentafluoro-2(E)-octenoic acid ethyl ester 17.4 g (50 mmol) of ethoxycarbonylmethylene-triphenylphosphorane are added to 40 ml (60 mmol) of the benzenic 6,6,6,5,5-pentafluorohexan-1-al solution (reaction solution from the preceding step) and maintained at reflux for 14 hours. The benzene is then distilled off in a rotary evaporator and the residue is separated from the triphenylphosphine oxide by flash chromatography over a column of silica gel (eluant: petroleum ether). The precipitated product is subjected to fractional distillation. The transester distils over at b.p.=103°-105° (28 mbar) in the form of a colourless liquid. (The first fraction contains small amounts of cis-ester; E/Z ratio before the distillation: 93:7). $^1$H-NMR spectrum, E-compound (CDCl$_3$; 60 MHz): 6.70 (d x t; J 15.5; 7; 1H), 5.67 (d; J 15.5; 1H), 4.07 (q; J 7; 2H), 2.2 (m; 2H), 1.8 (m; 4H), 1.24 (t; J 7).

$^1$H-NMR spectrum, Z-compound (CDCl$_3$; 60 MHz): 6.73 (d x t; J 12; 7; 1H), 5.85 (d; J 12; 1H), 4.06 (q; J 7; 2H), 2.6 (m; 2H), 1.9 (m; 4H), 1.12 (t; J 7, 3H).

d) 7,7,8,8,8-Pentafluoro-oct-2(E)-enol 380 ml of diisobutylaluminium hydride (1-molar in hexane) are added dropwise to a solution of 40.0 g of 7,7,8,8,8-pentafluoro-oct-2(E)ene-carboxylic acid ethyl ester in 300 ml of ether and the mixture is stirred for 2 hours at room temperature at 0°-5°. The resulting solution is poured onto a mixture of 480 ml of ice/water and 95 ml of concentrated hydrochloric acid (cooling, exothermic!). The mixture is stirred vigorously until two phases have formed. The organic phase is washed three times with saturated sodium chloride solution, dried over magnesium sulfate and concentrated by evaporation. The light-yellow oil that remains is distilled under a water-jet vacuum, yielding the title compound of b.p.=81°-86° C. (at 14 mm Hg); R$_f$ (hexane:ethyl acetate 3:2)=0.52; IR spectrum (CH$_2$Cl$_2$): 3600, 2950, 2860, 1450, 1380, 1200, 1130, 1030, 970, 650 cm$^{-1}$.

e) (2R,3R)-2,3-Epoxy-7,7,8,8,8-pentafluoro-octanol

Under totally anhydrous conditions and an argon atmosphere, a solution of 13.3 ml of tetraisopropyl orthotitanate in 100 ml of dichloromethane is cooled to −80°, and 9.1 ml of D(−)tartaric acid diethyl ester and 14.0 g of 7,7,8,8,8-pentafluoro-oct-2(E)enol in a small amount of dichloromethane are added. After stirring for 10 minutes at −80°, 61.7 ml of a 2.7-molar tert.-butyl hydroperoxide solution in toluene are added, the temperature rising to −68°. The temperature is then allowed to rise to 0° within a period of 2 hours, and the resulting yellow solution is poured slowly into a solution of 41.5 g of iron(II) sulfate and 16.0 g of L(+)-tartaric acid in 150 ml of water (cooling, exothermic!) and stirred for 30 minutes at 5°-10°.

The aqueous phase is separated off and extracted four times using 100 ml of ether each time. The combined organic extracts are dried over sodium sulfate and concentrated by evaporation. The residue is dissolved in 100 ml of ether and cooled to 0°-5°, and a suspension of 7.0 g of sodium hydroxide in 250 ml of saturated sodium chloride solution is added and the mixture is stirred for 1 hour at 0°-5°. The aqueous phase is separated off and extracted four times using 50 ml of ether each time. The combined ether phases are dried over sodium sulfate and concentrated by evaporation. The residue is purified by chromatography on silica gel using hexane/ethyl acetate (1:1) as eluant. The title compound is obtained in the form of a light-yellow oil: [α]$_D^{20}$ (CHCl$_3$, 0.49%)=15.3°±2.0°; R$_f$ (hexane:ethyl acetate 1:1): =0.36; IR spectrum (CH$_2$Cl$_2$): 3550, 2900, 1440, 1370, 1180, 1130, 1010, 870, 635 cm$^1$.

f) (4R,5R)-4,5-Epoxy-9,9,10,10,10-pentafluoro-dec-2(E)-enal 5.6 ml of pyridine, 2.3 ml of trifluoroacetic acid and 37.0 g of N,N-dicyclohexyl carbodiimide are added under argon to a solution of 11.0 g of (2R,3R)-2,3-epoxy-7,7,8,8,8-pentafluoro-octanol in 200 ml of dimethyl sulfoxide and the mixture is stirred at room temperature for 3 hours. After the addition of 23.6 g of formylmethylenetriphenylphosphorane, stirring is continued for a further 18 hours at room temperature; 500 ml of ethyl acetate are added and after 10 minutes the mixture is poured onto 1 liter of saturated sodium chloride solution. The resulting suspension is stirred for 15 minutes and filtered through a P4-frit. In the filtrate the aqueous phase is extracted three times using 100 ml of ethyl acetate each time. The combined organic phases are washed three times with saturated sodium chloride solution, dried over sodium sulfate and concentrated by evaporation. The residue is filtered over silica gel using ether/hexane (4:1+1% triethylamine) as eluant. The filtrate is concentrated by evaporation and the residue is filtered first over a column filled with 2 kg of silica gel and then chromatographed over a column filled with 500 g of silica gel using hexane/ethyl acetate (3:2) as eluant. The title compound is thus obtained in the form of a yellow oil; R$_f$ (hexane:ethyl acetate 1:1)=0.61; [α]$_D^{20}$ (0.21% in CDCl$_3$)=+19.5°±4.8°.

g) (6R,7S)-15-(4-Acetyl-3-hydroxy-2-propyl-phenoxy)-6,7-epoxy-1,1,1,2,2-pentafluoro-pentadeca-8(E),10(Z)-diene A suspension of 4.0 g of 5-(4-acetyl-3-hydroxy-2-propylphenoxy)-pentyl-triphenylphosphonium bromide in 150 ml of absolute tetrahydrofuran is stirred at room temperature under argon for 2.5 hours with 1.0 g of (4R,5R)-4,5-epoxy-9,9,10,10,10-pentafluoro-dec-2(E)-enal and 0.54 g of sodium amide. The resulting suspension is poured onto 400 ml of phosphate buffer (pH 7) and extracted four times using 25 ml of ether each time. The combined ether extracts are washed twice with 25 ml of phosphate buffer (pH 7) and once with saturated sodium chloride solution, dried over sodium sulfate and concentrated by evaporation. The residue is taken up in hexane:ethyl acetate (1:1+1% triethylamine) and filtered over a column of silica gel that has been prewashed with that solvent mixture. The filtrate is concentrated by evaporation and the residue is purified by chromatography on silica gel using hexane/ethyl acetate (7:3+1% triethylamine). The title compound is thus obtained in the form of a yellow oil; R$_f$ (hexane:ethyl acetate 1:1)=0.50; [α]$_D^{20}$ (CHCl$_3$, 0.20%)=+15°±5°.

EXAMPLE 103

Sodium salt of 7-[(6R,7S)-15-(4-acetyl-3-hydroxy-2-propyl-phenoxy)-1,1,1,2,2-pentafluoro-6-hydroxy-pentadeca-8(E),10(Z)-dien-7-ylthio]-4-oxo-4H-1-benzopyrane-2-carboxylic acid 1.3 g of the corresponding methyl ester according to Example 1 are dissolved under argon in 40 ml of tetrahydrofuran; 9.4 ml of 0.2N sodium hydroxide solution are added at 0° C. and the mixture is stirred for 1 hour at room temperature. Concentration by evaporation and purification of the residue over a 240 g Merck Lichroprep ® RP-8 column with methanol/water (7:3) as eluant yield the title compound of formula

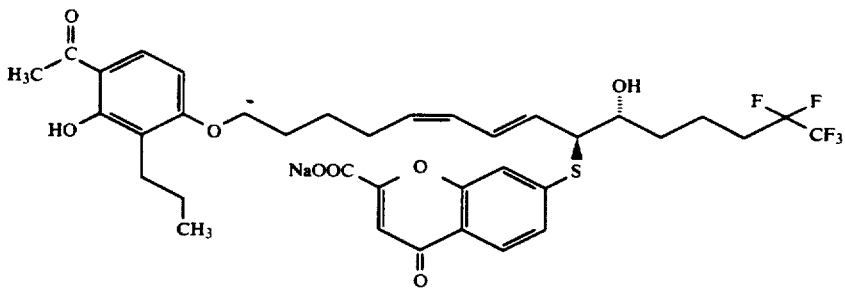

of m.p.: 155°–158°; $[\alpha]D_{20}$ ; (0.12%, MeOH)=44.2°±8.3°; UV spectrum (MeOH): $\lambda_{max}$=221 ($\epsilon$=48080), 231/sh, 267 ($\epsilon$=24720), 285 ($\epsilon$=22080), 325/sh; IR spectrum (CH$_2$Cl$_2$): 3480, 2920, 1630, 1450, 1420, 1360, 1200, 1120, 810 cm$^{-1}$; R$_f$ (MeOH/H$_2$O: 3:1):=0.20.

EXAMPLE 104

7-(6R,7S)-14-(4-Acetyl-3-hydroxy-2propylphenoxy)-1,1,1,2,2-pentafluoro-6-hydroxy-tetradeca-8(E),10(Z)-dien-7-ylthio]-4oxo-4H-1-benzopyrane-2-carboxylic acid methyl ester A solution of 0.53 g of (6R,7S)-14-(4-acetyl-3-hydroxy-2-propylphenoxy)-6,7-epoxy-1,1,1,2,2-pentafluoro-tetradeca-8(E),10(Z)-diene in 50 ml of absolute methanol is stirred under argon with 1.3 ml of triethylamine and 0.4 g of 7-mercaptochromone-2-carboxylic acid methyl ester for 20 hours at room temperature and then concentrated by evaporation. The residue is dissolved in ethyl acetate and filtered over silica gel. The filtrate is washed once with 25 ml of 1N hydrochloric acid and four times using 25 ml of saturated sodium chloride solution each time, dried over sodium sulfate and concentrated by evaporation. The residue is purified by chromatography on silica gel using hexane/ethyl acetate (7:3) as eluant. The title compound is obtained in the form of a yellow oil of R$_f$(hexane:ethyl acetate 3:2)=0.25.

The starting material can be prepared as follows:

a)
6R,7S)-14-(4-Acetyl-3-hydroxy-2-propyl-phenoxy)-6,7-epoxy-1,1,1,2,2-pentafluoro-tetradeca-8(E),10(Z)-diene 0.4 g of (4R,5R)-4,5-epoxy-9,9,10,10,10-pentafluorodec-2(E)-enal in 10 ml of tetrahydrofuran, 0.156 g of sodium amide and about 50 mg of potassium tert.-butanolate are added, with stirring, at −70° under argon to a suspension of 1.2 g of 4-(4-acetyl-3-hydroxy-2-propyl-phenoxy)butyltriphenylphosphonium bromide in 50 ml of absolute tetrahydrofuran. The temperature is then allowed to rise to room temperature within a period of 2.5 hours. The resulting suspension is poured onto 200 ml of phosphate buffer (pH 7) and extracted with ether. The combined ether phases are washed once with phosphate buffer (pH 7) and twice with saturated sodium chloride solution, dried over sodium sulfate and concentrated by evaporation. The residue is taken up in hexane/ethyl acetate (3:2+1% triethylamine) and filtered over a column of silica gel that has been prewashed with that solvent mixture. The filtrate is concentrated by evaporation and the residue is purified by chromatography on silica gel using hexane/ethyl acetate (7:3+1% triethylamine) as eluant. The title compound is obtained in the form of a light-yellow oil; R$_f$ (hexane/ethyl acetate 3:2)=0.50; $[\alpha]_D^{20}$ (CHCl$_3$, 0.0955%)=8.4°±10.5°; UV spectrum (CHCl$_3$): $\lambda_{max}$=287 ($\epsilon$ 20920), 330/sh.

EXAMPLE 105

Sodium salt of 7-(6R,7S)-14-(4-acetyl-3-hydroxy-2-propyl-phenoxy)-1,1,1,2,2-pentafluoro-6-hydroxy-tetradeca-8(E),10(Z)-dien-7-ylthio]-4-oxo-4H-1-benzopyrane-2-carboxylic acid The title compound of formula

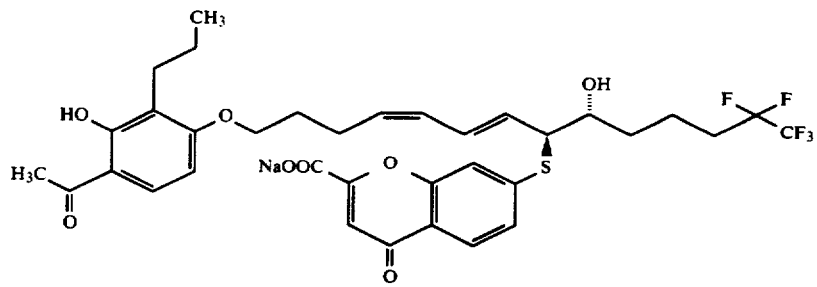

is prepared analogously to Example 2 from the corresponding methyl ester according to Example 3. M.p. 159°–160°; $[\alpha]_D^{20}$ (methanol, 0.087%)=+65.5°±11.5°, UV spectrum (methanol): $\lambda_{max}$, ($\epsilon$), 221 (44480), 231/sh, 267 (22960), 285 (20400), 330/sh; IR spectrum (CH$_2$Cl$_2$): 3380, 2950, 1630, 1500, 1420, 1360, 1270, 1200, 1120, 810 cm$^1$.

EXAMPLE 106

7-[(6R,7S)-15-(4-Acetyl-3-hydroxy-2-propylphenoxy)-1,1,1,2,2-pentafluoro-6-hydroxy-pentadeca-8(E),10(Z)-dien-7-ylthio]-4-oxo-4H-1-benzopyrane-2-carboxylic acid 0.87 g of the corresponding methyl ester according to Example 1 are dissolved under argon in 30 ml of tetrahydrofuran, then 6.3 ml of 0.2N sodium hydroxide solution are added at 0° and the mixture is stirred for 1 hour at 0 to 5°. The reaction mixture is freed of tetrahydrofuran in a rotary evaporator and taken up in 20 ml of water and 50 ml of methylene chloride. The mixture is acidified to pH 1 with 2N hydrochloric acid and extracted three times using 50 ml of methylene chloride each time. The combined organic phases are dried over sodium sulfate and concentrated by evaporation. The residue is purified over a column of silica gel using methylene chloride/methanol (4:1) as eluant, yielding the title compound in the form of a viscous resin.

EXAMPLE 107

In a manner analogous to that described in Examples 1 to 5 it is also possible to prepare:

7-[(6R,7S)-13-(4-acetyl-3-hydroxy-2-propyl-phenoxy)-1,1,1,2,2-pentafluoro-6-hydroxy-trideca-8(E),10(Z)-dien-7-ylthio]-4-oxo-4H-1-benzopyrane-2-carboxylic acid, the methyl ester and the sodium salt thereof;

7-[(5R,6S)-14-(4-acetyl-3-hydroxy-2-propyl-phenoxy)-1,1,1,2,2-pentafluoro-5-hydroxy-tetradeca-7(E),9(Z)-dien-6-ylthio]-4-oxo-4H-1-benzopyrane-2-carboxylic acid, the methyl ester and the sodium salt thereof;

7-[(5R,6S)-12-(4-acetyl-3-hydroxy-2-propyl-phenoxy)-1,1,1,2,2-pentafluoro-5-hydroxy-dodeca-7(E),9(Z)-dien-6-ylthio]-4-oxo-4H-1-benzopyrane-2-carboxylic acid, the methyl ester and the sodium salt thereof;

7-[(4R,5S)-13-(4-acetyl-3-hydroxy-2-propyl-phenoxy)-1,1,1,2,2-pentafluoro-4-hydroxy-trideca-6(E),8(Z)-dien-5-ylthio]-4-oxo-4H-1-benzopyrane-2-carboxylic acid, the methyl ester and the sodium salt thereof;

7-[(4R,5S)-11-(4-acetyl-3-hydroxy-2-propyl-phenoxy)-1,1,1,2,2-pentafluoro-4-hydroxy-undeca-6(E),8(Z)-dien-5-ylthio]-4-oxo-4H-1-benzopyrane-2-carboxylic acid, the methyl ester and the sodium salt thereof;

7-[(3R,4S)-12-(4-acetyl-3-hydroxy-2-propyl-phenoxy)-2,2-dichloro-1,1,1-trifluoro-3-hydroxy-1-dodeca-7(E),9(Z)-dien-4-ylthio]-4-oxo-4H-1-benzopyrane-2-carboxylic acid, the methyl ester and the sodium salt thereof;

7-[(5R,6S)-14-(4-acetyl-3-hydroxy-2-propyl-phenoxy)-2,2-dichloro-1,1,1-trifluoro-5-hydroxy-tetradeca-7(E),9(Z)-dien-6-ylthio]-4-oxo-4H-1-benzopyrane-2-carboxylic acid, the methyl ester and the sodium salt thereof;

7-[(3R,4S)-10-(4-acetyl-3-hydroxy-2-propyl-phenoxy)-2,2-dichloro-1,1,1-trifluoro-3-hydroxy-deca-5(E),7(Z)-dien-4-yl-thio]-4-oxo-4H-1-benzopyrane-2-carboxylic acid, the methyl ester and the sodium salt thereof;

7-[(3R,4S)-11-(4-acetyl-3-hydroxy-2-propyl-phenoxy)-2,2-dichloro-1,1,1-trifluoro-3-hydroxy-undeca-5(E),7(Z)-dien-4-ylthio]-4-oxo-4H-1-benzopyrane-2-carboxylic acid, the methyl ester and the sodium salt thereof;

7-[(3R,4S)-13-(4-acetyl-3-hydroxy-2-propyl-phenoxy)-2,2-dichloro-1,1,1-trifluoro-3-hydroxy-trideca-5(E),7(Z)-dien-4-ylthio]-4-oxo-4H-1-benzopyrane-2-carboxylic acid, the methyl ester and the sodium salt thereof;

7-[(3R,4S)-14-(4-acetyl-3-hydroxy-2-propyl-phenoxy)-2,2-dichloro-1,1,1-trifluoro-3-hydroxy-tetradeca-5(E),7(Z)-dien-4-ylthio]-4-oxo-4H-1-benzopyrane-2-carboxylic acid, the methyl ester and the sodium salt thereof;

7-[(5R,6S)-14-(4-acetyl-3-hydroxy-2-propyl-phenoxy)-2,2-dichloro-1,1,1-trifluoro-5-hydroxy-tetradeca-7(E),9(Z)-dien-6-ylthio]-4-oxo-4H-1-benzopyrane-2-carboxylic acid, the methyl ester and the sodium salt thereof;

7-[(5R,6S)-13-(4-acetyl-3-hydroxy-2-propyl-phenoxy)-2,2-dichloro-1,1,1-trifluoro-5-hydroxy-trideca-7(E),9(Z)-dien-6-ylthio]-4-oxo-4H-1-benzopyrane-2-carboxylic acid, the methyl ester and the sodium salt thereof, and 7-[(5R,6S)-12-(4-acetyl-3-hydroxy-2-propyl-phenoxy)-2,2-dichloro-1,1,1-trifluoro-5-hydroxy-dodeca-(7E),9(Z)-dien-6-ylthio]-4-oxo-4H-1-benzopyrane-2-carboxylic acid, the methyl ester and the sodium salt thereof.

EXAMPLE 108

In an analogous manner as described in Example 105, also the free acids corresponding to the sodium salts described in Examples 2, 4, 6, 8, 10, 12, 14, 16, 18, 20, 22, 24, 26, 28, 30, 32, 34, 36, 38, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103 and 105 can be manufactured.

EXAMPLE 109

In a manner analogous to that described in Examples 1 to 77 it is also possible to prepare:

(1R,2S)-1-hydroxy-1-phenyl-11-(4-acetyl-3-hydroxy-2-propylphenoxy)undeca-3(E),5(Z)-dien-2-yl-7-thio-4-oxo-4H-1-benzopyrane-2-carboxylic acid;

(1R,2S)-1-hydroxy-1-phenyl-10-(4-acetyl-3-hydroxy-2-propylphenoxy)deca-3(E),5(Z)-dien-2-yl-7-thio-4-oxo-4H-1-benzopyrane-2-carboxylic acid;

(1R,2S)-1-hydroxy-1-phenyl-9-(4-acetyl-3-hydroxy-2-propylphenoxy)-nona-3(E),5(Z)-dien-2-yl-7-thio-4-oxo-4H-1-benzopyrane-2-carboxylic acid;

(1R,2S)-1-hydroxy-1-(3-chlorophenyl)-9-(4-acetyl-3-hydroxy-2-propylphenoxy)-nona-3(E),5(Z)-dien-2-yl-7-thio-4-oxo-4H-1-benzopyrane-2-carboxylic acid;

(1R,2S)-1-hydroxy-1-(3-chlorophenyl)-11-(4-acetyl-3-hydroxy-2-propylphenoxy)-undeca-3(E),5(Z)-dien-2-yl-7-thio-4-oxo-4H-1-benzopyrane-2-carboxylic acid;

(1R,2S)-1-hydroxy-1-(3-fluorophenyl)-8-(4-acetyl-3-hydroxy-2-propylphenoxy)-octa-3(E),5(Z)-dien-2-yl-7-thio-4-oxo-4H-1-benzopyrane-2-carboxylic acid;

(1R,2S)-1-hydroxy-1-(3-fluorophenyl)-9-(4-acetyl-3-hydroxy-2-propylphenoxy)-nona-3(E),5(Z)-dien-2-yl-7-thio-4-oxo-4H-1-benzopyrane-2-carboxylic acid;

(1R,2S)-1-hydroxy-1-(3-fluorophenyl)-10-(4-acetyl-3-hydroxy-2-propylphenoxy)-deca-3(E),5(Z)-dien-2-yl-7-thio-4-oxo-4H-1-benzopyrane-2-carboxylic acid;

(1R,2S)-1-hydroxy-1-(3-fluorophenyl)-11-(4-acetyl-3-hydroxy-2-propylphenoxy)-undeca-3(E),5(Z)-dien-2-yl-7-thio-4-oxo-4H-1-benzopyrane-2-carboxylic acid;

(1R,2S)-1-hydroxy-1-(3-methoxyphenyl)-9-(4-acetyl-3-hydroxy-2-propylphenoxy)-nona-3(E),5(Z)-dien- 2-yl-7-thio-4-oxo-4H-1-benzopyrane-2-carboxylic acid;

(1R,2S)-1-hydroxy-1-(3-methoxyphenyl)-11-(4-acetyl-3-hydroxy-2-propylphenoxy)-undeca-3(E),5(Z)-dien-2-yl-7-thio-4-oxo-4H-1-benzopyrane-2-carboxylic acid;

(1R,2S)-1-hydroxy-1-(3-carboxyphenyl)-8-(4-acetyl-3-hydroxy-2-propylphenoxy)-octa-3(E),5(Z)-dien-2-yl-7-thio-4-oxo-4H-1-benzopyrane-2-carboxylic acid;

(1R,2S)-1-hydroxy-1-(3-carboxyphenyl)-9-(4-acetyl-3-hydroxy-2-propylphenoxy)-nona-3(E),5(Z)-dien-2-yl-7-thio-4-oxo-4H-1-benzopyrane-2-carboxylic acid;

(1R,2S)-1-hydroxy-1-(3-carboxyphenyl)-10-(4-acetyl-3-hydroxy-2-propylphenoxy)-deca-3(E),5(Z)-dien-2-yl-7-thio-4-oxo-4H-1-benzopyrane-2-carboxylic acid;

(1R,2S)-1-hydroxy-1-(3-carboxyphenyl)-11-(4-acetyl-3-hydroxy-2-propylphenoxy)-undeca-3(E),5(Z)-dien-2-yl-7-thio-4-oxo-4H-1-benzopyrane-2-carboxylic acid;

(1R,2S)-1-hydroxy-1-(3-methoxycarbonylphenyl)-9-(4-acetyl-3-hydroxy-2-propylphenoxy)-nona-3(E),5(Z)-dien-2-yl-7-thio-4-oxo-4H-1-benzopyrane-2-carboxylic acid;

(1R,2S)-1-hydroxy-1-(3-methoxycarbonylphenyl)-10-(4-acetyl-3-hydroxy-2-propylphenoxy)-deca-3(E),5(Z)-dien-2-yl-7-thio-4-oxo-4H-1-benzopyrane-2-carboxylic acid;

(1R,2S)-1-hydroxy-1-(3-methoxycarbonylphenyl)-11-(4-acetyl-3-hydroxy-2-propylphenoxy)-undeca-3(E),5(Z)-dien-2-yl-7-thio-4-oxo-4H-1-benzopyrane-2-carboxylic acid;

(1R,2S)-1-hydroxy-1-(3,4-dichlorophenyl)-10-(4-acetyl-3-hydroxy-2-propylphenoxy)-deca-3(E),5(Z)-dien-2-yl-7-thio-4-oxo-4H-1-benzopyrane-2-carboxylic acid;

(1R,2S)-1-hydroxy-1-(2,4-dichlorophenyl)-10-(4-acetyl-3-hydroxy-2-propylphenoxy)-deca-3(E),5(Z)-dien-2-yl-7-thio-4-oxo-4H-1-benzopyrane-2-carboxylic acid;

(1R,2S)-1-hydroxy-1-(3,4-dimethoxyphenyl)-10-(4-acetyl-3-hydroxy-2-propylphenoxy)-deca-3(E),5(Z)-dien-2-yl-7-thio-4-oxo-4H-1-benzopyrane-2-carboxylic acid;

(1R,2S)-1-hydroxy-1-(2,4-dimethoxyphenyl)-10-(4-acetyl-3-hydroxy-2-propylphenoxy)-deca-3(E),5(Z)-dien-2-yl-7-thio-4-oxo-4H-1-benzopyrane-2-carboxylic acid;

(1R,2S)-1-hydroxy-1-(2,4-dimethylphenyl)-10-(4-acetyl-3-hydroxy-2-propylphenoxy)-deca-3(E),5(Z)-dien-2-yl-7-thio-4-oxo-4H-1-benzopyrane-2-carboxylic acid;

(1R,2S)-1-hydroxy-1-(3-dimethylaminophenyl)-10-(4-acetyl-3-hydroxy-2-propylphenoxy)-deca-3(E),5(Z)-dien-2-yl-7-thio-4-oxo-4H-1-benzopyrane-2-carboxylic acid; and in each case the sodium or disodium salts thereof.

EXAMPLE 110

In a manner analogous to that described in Examples 1 to 107 it is also possible to prepare the following compounds:

(1R,2S)-1-hydroxy-1-(3-bromophenyl)-8-(4-acetyl-3-hydroxy-2-propylphenoxy)-octa-3(E),5(Z)-dien-2-yl-7-thio-4-oxo-4H-1-benzopyrane-2-carboxylic acid;

(1R,2S)-1-hydroxy-1-(3-bromophenyl)-9-(4-acetyl-3-hydroxy-2-propylphenoxy)-nona-3(E),5(Z)-dien-2-yl-7-thio-4-oxo-4H-1-benzopyrane-2-carboxylic acid;

(1R,2S)-1-hydroxy-1-(3-bromophenyl)-10-(4-acetyl-3-hydroxy-2-propylphenoxy)-deca-3(E),5(Z)-dien-2-yl-7-thio-4-oxo-4H-1-benzopyrane-2-carboxylic acid;

(1R,2S)-1-hydroxy-1-(3-bromophenyl)-11-(4-acetyl-3-hydroxy-2-propylphenoxy)-undeca-3(E),5(Z)-dien-2-yl-7-thio-4-oxo-4H-1-benzopyrane-2-carboxylic acid;

(5R,6S)-1,1,1-trifluoro-5-hydroxy-13-(4-acetyl-3-hydroxy-2-propylphenoxy)-trideca-7(E),9(Z)-dien-6-yl-7-thio-4-oxo-4H-1-benzopyrane-2-carboxylic acid;

(5R,6S)-1,1,1-trifluoro-5-hydroxy-15-(4-acetyl-3-hydroxy-2-propylphenoxy)-pentadeca-7(E),9(Z)-dien-6-yl-7-thio-4-oxo-4H-1-benzopyrane-2-carboxylic acid;

(5R,6S)-5-hydroxy-13-(4-acetyl-3-hydroxy-2-propylphenoxy)-trideca-7(E),9(Z)-dien-6-yl-7-thio-4-oxo-4H-1-benzopyrane-2--carboxylic acid;

(5R,6S)-5-hydroxy-15-(4-acetyl-3-hydroxy-2-propylphenoxy)-pentadeca-7(E),9(Z)-dien-6-yl-7-thio-4-oxo-4H-1-benzopyrane-2--carboxylic acid;

(4R,5S)-1-carboxy-4-hydroxy-11-(4-acetyl-3-hydroxy-2-propylphenoxy)undeca-6(E),8(Z)-dien-6-yl-7-thio-4-oxo-4H-1-benzopyrane-2-carboxylic acid;

(4R,5S)-1-carboxy-4-hydroxy-12-(4-acetyl-3-hydroxy-2-propylphenoxy)dodeca-6(E),8(Z)-dien-5-yl-7-thio-4-oxo-4H-1-benzopyrane-2-carboxylic acid;

(4R,5S)-1-carboxy-4-hydroxy-13-(4-acetyl-3-hydroxy-2-propylphenoxy)trideca-6(E),8(Z)-dien-5-yl-7-thio-4-oxo-4H-1-benzopyrane-2-carboxylic acid;

(4R,5S)-1-carboxy-4-hydroxy-14-(4-acetyl-3-hydroxy-2-propylphenoxy)tetradeca-6(E),8(Z)-dien-5-yl-7-thio-4-oxo-4H-1-benzopyrane-2-carboxylic acid; and in each case the sodium or disodium salt thereof.

EXAMPLES OF PHARMACEUTICAL PREPARATIONS and corresponding finished medicament forms In the following the term "active ingredient" is to be understood as being a compound of formula I according to the invention, especially a compound described as a product in Examples 1 to 9, for example the sodium salt of (1R,2S)-1-hydroxy-1-(3-trifluoromethylphenyl)-8-(4-acetyl-3-hydroxy-2-propylphenoxy)-octa-3(E),5(Z)-dien-2-yl-7-thio-4-oxo-4H-1-benzopyrane-2-carboxylic acid.

EXAMPLE A

An inhalation suspension, containing propellant and forming a solid aerosol, containing 0.1% by weight active ingredient

| Composition: | % by weight |
| --- | --- |
| active ingredient, micronised | 0.1 |
| sorbitan trioleate | 0.5 |
| Propellant A | |
| (trichlorotrifluoroethane) | 4.4 |
| Propellant B | |
| (dichlorodifluoromethane and 1,2-dichlorotetrafluoroethane) | 15.0 |
| | 80.0 |

Preparation: In the absence of moisture, the active ingredient is suspended in trichlorotrifluoroethane using a customary homogeniser and with the addition of the sorbitan trioleate, the suspension is introduced into an aerosol container provided with a metering valve; the container is sealed and filled up with propellant B under pressure.

EXAMPLE B

An approximately 2% aqueous solution, suitable for inhalation, of an active ingredient in the form of its sodium or potassium salt.

| Composition: | |
|---|---|
| active ingredient (K or Na salt) | 2000 mg |
| disodium salt of ethylenediaminetetraacetic acid | 10 mg |
| benzalkonium chloride | 10 mg |
| water, freshly distilled | ad 100 ml |

Preparation: The active ingredient is dissolved in approximately 60 ml of freshly distilled water, and the stabiliser (disodium salt of ethylenediaminetetraacetic acid) and the preservative (benzalkonium chloride) are added. When all the components have completely dissolved, the resulting solution is made up to 100 ml and introduced into small pressurised bottles which are then sealed in gas-tight manner. The propellant is added, as required, in gaseous form under pressure or in liquid form.

APPENDIX—PHARMACOLOGICAL TEST METHODS

Bronchoconstriction test on guinea pigs (in vivo, aerosol)

Male guinea pigs weighing 400–700 g are anaesthetised intraperitoneally with 1.4 g/kg of urethane and a polyethylene cannula is inserted into the jugular vein. A second polyethylene cannula is inserted into the trachea. The pressure in the oesophagus is recorded by means of a cannula that is inserted into the oesophagus and that is connected to a Statham pressure transducer. The animal is placed in an airtight plexiglass chamber which is connected to a Fleisch's tube No. 000 and a Validyne transducer MP 45-1. This arrangement is used to measure the flow.

After the surgical preparation of the test animals, a certain period of time is allowed to elapse to enable the pulmonary functions to stabilise. The test compound is then administered in accordance with the following procedure: The test animals are exposed for one minute to a 1% aerosol solution of the test compound (weight-/volume) or to distilled water (for control purposes). For all the test compounds that are administered by inhalation, a Monaghan ultrasound spray apparatus (model 670) of which the particle size varies between 1 and 8 microns, the majority being 3 microns, is used.

Aqueous solutions are freshly prepared each time and are introduced into the chamber of the spray device using an On-stream drug vial. The spray mist produced is administered to the experimental animals via a glass chamber of 65 ml capacity which is connected to the trachea by a cannula. When the treatment period has elapsed, LTD$_4$ (0.3 μg/ml) is administered over a period of 2 minutes using a second Monaghan ultrasound spray device (model 670) and via a similar glass chamber.

The reduction in compliance in the third minute after the LTD$_4$ administration is read off and the average value of three animals is compared with the average value of three control animals and the percentage inhibition of compliance is calculated in accordance with the following formula:

$$\% \text{ inhibition} = 100 - \frac{(100 - \text{compliance preparation}) \times 100}{(100 - \text{compliance control})}$$

If different concentrations of active ingredient are tested, the percentage inhibition for each concentration is recorded, the log concentration on the abscissa being plotted against the percentage inhibition on the ordinate. The IC$_{50}$ is then determined by linear regression analysis.

In vitro test to determine the inhibition of phospholipase A$_2$ obtained from human leucocytes Neutrophilic polymorpho-nuclear human leucocytes are isolated from "Buffy coats" by multi-step fractional sedimentation and are deep-frozen. The phospholipase A$_2$ is extracted from the cell suspension by homogenisation with the addition of ice-cold 0.36N H$_2$SO$_4$ in 2N NaCl and the supernatant obtained after centrifugation at 10,000×g is dialysed against sodium acetate buffer pH 4.5.

In order to determine the enzyme activity, enzyme (10–30 μg of protein) is incubated at 37° for 1 hour in 0.1M tris/HCl buffer pH 7 with the addition of 1 mmol of CaCl$_2$ and substrate consisting of phospholipids (2 μm) of *Escherichia coli* radioactively labelled biosynthetically with $^{14}$C-oleic acid. The reaction is stopped by the addition of Dole reagent (isopropanol/heptane/1N H$_2$SO$_4$ 40:10:1, v/v) and the $^{14}$C-oleic acid freed selectively by phospholipase A$_2$ is extracted. Substrate extracted therewith is completely removed by filtration of the extract through a column of silica gel. The determination of $^{14}$C-oleic acid in the eluate is effected by radiometry.

In order to detect an inhibitory action of test substances on phospholipase A$_2$, the test substances are added to the incubation mixture in the form of solutions in water, dimethyl sulfoxide (final concentration in the batch up to 5%, v/v) or ethanol (final concentration in the batch up to 2.5%, v/v). The degree of action of the test substances is expressed by the IC$_{50}$, that is to say the concentration which effects inhibition of 50% of the control activity. The IC$_{50}$ is determined graphically by plotting the percentage inhibition on the ordinate against the log of the concentration (μm) on the abscissa.

Under the described test conditions MEPACRINE ® quinacrin hydrochloride inhibits phospholipase A$_2$ with an IC$_{50}$ of 1600 pm.

In vitro test to determine the inhibition of phospholipase C obtained from human thrombocytes Human thrombocytes are obtained from "Buffy coats" by fractional centrifugation and are then deep-frozen. The phospholipase C is freed by ultrasound treatment of the cell suspension and after ultracentrifugation (150,000×g for 1 hour) is present in soluble form in the supernatant.

In order to determine the enzyme activity, enzyme (20–100 μg of protein) is incubated at 37° for 5 minutes in 0.025M tris/maleate buffer pH 6 with the addition of 0.2 mmol of CaCl$_2$ and 0.02 mmol of radioactively labelled substrate, phosphatidyl-[$^{14}$C]-inositol. The reaction is stopped by shaking with CHCl$_3$/CH$_3$OH 2:1 (v/v), in the course of which unused substrate is extracted into the organic phase, while the reaction product, $^{14}C$-inositol phosphate, remains in the aqueous phase and can be measured by radiometry of an aliquot.

In order to detect an inhibitory action of test substances on phospholipase C, the test substances are added to the incubation mixture in the form of solutions in water, dimethyl sulfoxide (final concentration in the batch up to 5%, v/v) or ethanol (final concentration in the batch up to 2.5%, v/v). The degree of action of the test substances is expressed by the $IC_{50}$, that is to say the concentration which effects inhibition of 50% of the control activity. The $IC_{50}$ is determined graphically by plotting the percentage inhibition on the ordinate against the log of the concentration ($\mu m$) on the abscissa.

Under the described test conditions MEPARCRINE® quinacrin hydrochloride inhibits phospholipase C with an $IC_{50}$ of 20 $\mu m$.

What is claimed is:

1. Substituted alkanophenone of the formula

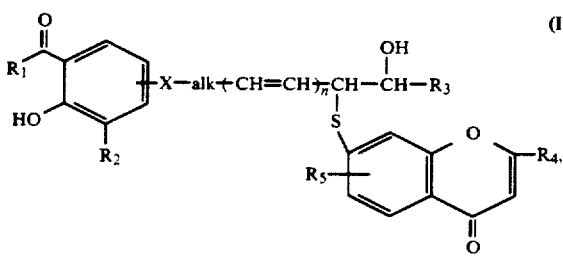

in which $R_1$ is unsubstituted or fluorinated lower alkyl, $R_2$ is hydrogen, or unsubstituted or fluorinated lower alkyl or lower alkenyl, X is lower alkylene, oxy, thio or a direct bond, alk is lower alkylene, n is 1 or 2, $R_3$ is phenyl that is unsubstituted or is substituted by unsubstituted or fluorinated lower alkyl, lower alkoxy, halogen, unsubstituted or lower alkylated amino carboxy, lower alkoxycarbonyl, carbamoyl, N-(benzenesulfonyl)-carbamoyl that is unsubstituted or substituted in the phenyl moiety by lower alkyl, lower alkoxy, halogen or a combination thereof, $R_4$ is 5-tetrazolyl, and $R_5$ is hydrogen or lower alkyl or a salt thereof.

2. A compound according to claim 1 of the formula I, in which $R_1$ is lower alkyl or mono-, di- or poly-fluoro-lower alkyl, $R_2$ is hydrogen, lower alkyl, lower alkenyl or mono-, di- or poly-fluoro-lower alkyl, X is lower alkylene, n is 1 or 2 oxy or thio, alk is lower alkylene, $R_3$ is phenyl that is unsubstituted or is substituted by lower alkyl, lower alkoxy, halogen, carboxy, lower alkoxycarbonyl, amino, N-mono- or N, N-di-lower alkylamino, carbamoyl, N-mono- or N,N-di-lower alkylcarbamoyl, trifluoromethyl or a combination thereof, or is lower alkyl, mono-, di- or poly-fluoro-lower alkyl, mono-, di- or poly-fluoro-lower (di- or polychloro)alkyl, carboxy-lower alkyl, lower alkoxycarbonyl-lower alkyl, carbamoyl-lower alkyl or N-mono- or N,N-di-lower alkylcarbamoyl-lower alkyl, $R_4$ is carboxy, lower alkoxycarbamoyl, 5-tetrazoly, carbamoyl, N-mono- or N,N-di-lower alkylcarbamoyl, or N-(benzenesulfonyl)-carbamoyl that is unsubstituted or substituted in the phenyl moiety by lower alkyl, lower alkoxy, halogen or combinations thereof, and $R_5$ is hydrogen or lower alkyl or a salt thereof.

3. A compound according to claim 1, of formula I, in which $R_1$ is $C_1$-$C_4$-alkyl or $\omega$, $\omega$, $\omega$-trifluoro-$C_1$-$C_4$alkyl, $R_2$ is hydrogen, $C_1$-$C_4$alkyl, $C_2$-$C_4$alkenyl or $\omega,\omega,\omega$-trifluoro-$C_1$-$C_4$alkyl, X is $C_1$-$C_3$alkylene, oxy or thio, alk is straight-chain $C_2$-$C_6$alkylene, n is 1 or 2, $R_3$ is phenyl that is unsubstituted or substituted by $C_1$-$C_4$alkyl, $C_1$-$C_4$alkoxy, halogen having an atomic number of up to and including 35, trifluoromethyl, carboxy, $C_1$-$C_4$alkoxycarbonyl or combinations thereof, or is $C_1$-$C_8$alkyl, $\omega,\omega,\omega$-trifluoro-$C_2$-$C_7$alkyl, $\omega,\omega,\omega$-trifluoro-$C_2$-$C_7$alkyl, $\omega,\omega,\omega,\omega$-1,$\omega$-1-pentafluoro-$C_2$-$C_7$alkyl, $\omega,\omega,\omega$-trifluoro-$\omega$-1,$\omega$-1-dichloro-$C_2$-$C_7$alkyl, carboxy-$C_2$-$C_5$alkyl or $C_1$-$C_4$alkoxycarbonyl-$C_2$-$C_5$alkyl, $R_4$ is carboxy or N-(benzenesulfonyl)-carbamoyl, and $R_5$ is hydrogen or a salt thereof.

4. A compound according to claim 1 of formula

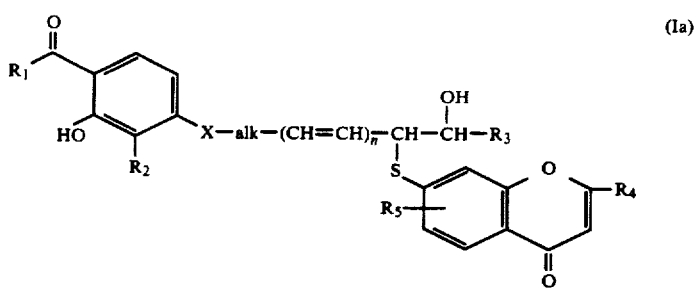

moiety by lower alkyl, lower alkoxy, halogen or a combination thereof, N-mono- or N,N-di-lower alkylcarbamoyl, or a combination thereof, or is lower alkyl that is unsubstituted or is substituted by fluoro or fluoro and chloro, carboxy, lower alkoxycarbonyl, carbamoyl, N-mono- or N,N-di-lower alkylcarbamoyl or N-(benzenesulfonyl)-carbamoyl that is unsubstituted or substituted in the phenyl moiety by lower alkyl, lower alkoxy, halogen or a combination thereof, $R_4$ is carboxy, lower alkoxycarbonyl, carbamoyl or N-mono- or N,-di-lower alkylcarbamoyl or N-(benzenesulfonyl)-carbamoyl that is unsubstituted or substituted in the phenyl in which $R_1$ is $C_1$-$C_4$alkyl, $R_2$ is $C_1$-$C_4$alkyl, X is oxy, alk is $C_2$-$C_6$alkylene, n is 1 or 2, $R_3$ is phenyl substituted by $C_1$-$C_4$alkyl, $C_1$-$C_4$alkoxy, halogen having an atomic number of up to and including 35, trifluoromethyl or by $C_1$-$C_4$alkoxycarbonyl, or is $C_2$-$C_8$alkyl, $\omega,\omega,\omega$-trifluro-$C_3$-$C_7$alkyl, $\omega,\omega,\omega,\omega$-1,$\omega$-1-pentafluoro-$C_2$-$C_7$alkyl, $\omega,\omega,\omega$-trifluoro-$\omega$-1,$\omega$-1dichloro-$C_2$-$C_7$alkyl or $C_1$-$C_4$alkyoxycarbonyl-$C_1$-$C_4$alkyl, $R_4$ is carboxy, and $R_5$ is hydrogen or a salt thereof.

5. A compound according to claim 1 of formula

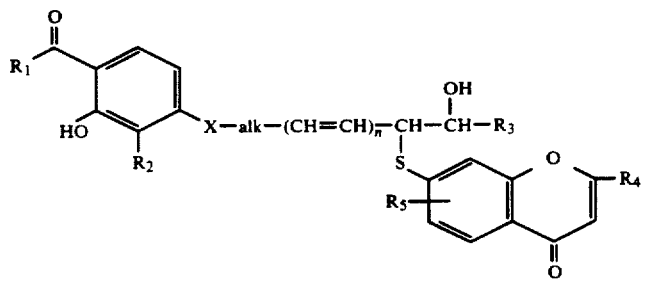

(Ia)

in which $R_1$ is $C_1$–$C_4$alkyl, $R_2$ is $C_1$–$C_4$alkyl, X is oxy, alk is $C_2$–$C_5$alkylene, n is 2, $R_3$ is phenyl substituted by $C_1$–$C_4$alkyl, trifluoromethyl or by $C_1$–$C_4$alkoxycarbonyl, or is $C_3$–$C_5$alkyl, $\omega,\omega,\omega$-trifluoro-$C_3$–$C_5$alkyl, $\omega,\omega,\omega$-1,$\omega$-1-pentafluoro-$C_3$–$C_7$alkyl, $\omega,\omega,\omega$-trifluoro-$\omega$-1,$\omega$-1-dichloro-$C_3$–$C_6$alkyl or $C_1$–$C_4$alkoxycarbonyl-$C_1$–$D_4$-alkyl, $R_4$ is carboxy, and $R_5$ is hydrogen or a salt thereof.

6. A compound according to claim 2 in which the double bond adjacent to the radical alk is in the (Z)-, that is to say the cis-configuration, and the additional double bond which may be present is in the (E)-, that is to say the trans-configuration and the chain carbon atom bonded to the sulfur atom has the (S)-configuration and the chain carbon atom carrying the hydroxy group has the (R)-configuration.

7. A compound selected from the group consisting of
(1R,2S)-1-hydroxy-1-(3-trifluoromethylphenyl)-8-(4-acetyl-3-hydroxy-2-propylphenoxy)-octa-3(E),5(Z)-dien-2-yl-7-thio-4-oxo-4H-1-benzopyrane-2-carboxylic acid,
(1R,2S)-1-hydroxy-1-(3-methylphenyl)-8-(4-acetyl-3-hydroxy-2-propylphenoxy)-octa-3(E),5(Z)-dien-2-yl-7-thio-4-oxo-4H-1-benzopyrane-2-carboxylic acid,
(1R,2S)-1-hydroxy-1,3-methoxycarbonylphenyl)-8-(4-acetyl-3-hydroxy-2-propylphenoxy)-octa-3(E),5(Z)-dien-2-yl-7-thio-4-oxo-4H-1-benzopyrane-2-carboxylic acid,
(4R,5S)-1,1,1-trifluoro-4-hydroxy-11-(4-acetyl-3-hydroxy-2propylphenoxy)-undeca-6(E),8(Z)-dien-5-yl-7-thio-4-oxo-4H-1-benzopyrane-2-carboxylic acid,
(1R,2S)-1-hydroxy-1(3-fluorophenyl)-10-(4-acetyl-3-hydroxy-2-propylphenoxy)-deca-3(E),5(Z)-dien-2yl-7-thio-4-oxo-4H-1-benzopyrane-2-carboxylic acid,
(1R,2S)-1-hydroxy-1-(3-trifluoromethylphenyl)-10-(4-acetyl-3-hydroxy-2-propylphenoxy)-deca-3(E),5(Z)-dien-2-yl-7-thio-4-oxo-4H-1-benzopyrane-2-carboxylic acid,
(1R,2S)-1-hydroxy-1-(3-bromophenyl)-10-(4-acetyl-3-hydroxy-2propylphenoxy)-deca-3(E),5(Z)-dien-2yl-7-thio-4-oxo-4H-1-benzopyrane-2carboxylic acid,
(1R,2S)-1-hydroxy-1-(3-methylphenyl)-10-(4-acetyl-3-hydroxy-2propylphenoxy)-deca-3(E),5(Z)-dien-2-yl-7-thio-4-oxo-4H-1-benzopyrane-2-carboxylic acid,
(1R,2S)-1-hydroxy-1-(3trifluoromethylphenyl)-9-(4-acetyl-3-hydroxy-2-propylphenoxy)-nona-3(E),5(Z)-dien-2yl-7-thio-4-oxo-4H-1-benzopyrane-2-carboxylic acid, (1R,2S)-1-hydroxy-1-(3-trifluoromethylphenyl)-11-(4-acetyl-3-hydroxy-2-propylphenoxy)-undeca-3(E),5(Z)-dien-2yl-7-thio-4-oxo-4H-1-benzopyrane-2-carboxylic acid,
(1R,2S)-1-hydroxy-1-(3-chlorophenyl)-10-(4-acetyl-3-hydroxy-2-propylphenoxy)-deca-3(E),5(Z)-dien-2-yl-7-thio-4-oxo-4H-1-benzopyrane-2-carboxylic acid,
(1R,2S)-1-hydroxy-1-(3-methoxyphenyl)-10-(4-acetyl-3-hydroxy-2-propylphenoxy)-deca-3(E),5(Z)-dien-2-yl-7-thio-4-oxo-4H-1-benzopyrane-2-carboxylic acid, and
(6R,7S)-1,1,1,2,2-pentafluoro-6-hydroxy-15-(4-acetyl-3-hydroxy-2-propylphenoxy)-pentadeca-8(E),10(Z)-dien-2-yl-7-thio-4-oxo-4H-1-benzopyrane-2-carboxylic acid, or the sodium salt thereof.

8. (6R,7S)-1,1,1,2,2-pentafluoro-6-hydroxy-14-(4-acetyl-3-hydroxy-2-propylphenoxy)-tetradeca-8(E),10(Z)-dien-7-yl-7-thio-4-oxo-4H-1-benzopyrane-2-carboxylic acid methyl ester according to claim 1.

9. (1R,2S)-1-hydroxy-1-(3-trifluoromethylphenyl)-10-(4-acetyl-3-hydroxy-2propylphenoxy)-deca-3(E),5(Z)-dien-2yl-7-thio-4-oxo-4H-1-benzopyrane-2-carboxylic acid according to claim 1 or the sodium salt thereof.

10. (1R,2S)-1-hydroxy-1-phenyl-10-(4-acetyl-3-hydroxy-2-propylphenoxy)-deca-3(E),5(Z)-dien-2-yl-7-thio-4-oxo-4H-1-benzopyrane-2-carboxylic acid according to claim 1 or the sodium salt thereof.

11. A pharmaceutical preparation for the alleviation of patholigic conditions resulting from the action of leucotrienes containing as pharmaceutical active ingredient, a therapeutically effective amount of a compound according to claim 1.

12. A method for the treatment of allergic diseases in a patient in need of such treatment, which method comprises the administration of a therapeutically effective amount of a compound according to claim 1.

13. A pharmaceutical preparation according to claim 11, wherein the compound used is (1R,2S)-1-hydroxy-1-(3-trifluoromethylphenyl)-10-(4-acetyl-3-hydroxy-2-propylphenoxy)-deca-3(E),5(Z)-dien-2-yl-7-thio-4-oxo-4H-1-benzopyrane-2-carboxylic acid or the sodium salt thereof.

14. A method according to claim 12, wherein the compound used is (1R,2S)-1-hydroxy-1-(3-trifluoromethylphenyl)-10-(4-acetyl-3-hydroxy-2-propylphenoxy)-deca-3(E),5(Z)-dien-2-yl-7-thio-4-oxo-4H-1-benzopyrane-2-carboxylic acid or the sodium salt thereof.

* * * * *

UNITED STATES PATENT AND TRADEMARK OFFICE
CERTIFICATE OF CORRECTION

PATENT NO. : 5,149,717

DATED : September 22, 1992

INVENTOR(S) : Von Sprecher, et al

It is certified that error appears in the above-indentified patent and that said Letters Patent is hereby corrected as shown below:

Column 61, claim 1,

--1. Substituted alkanophenone of the formula

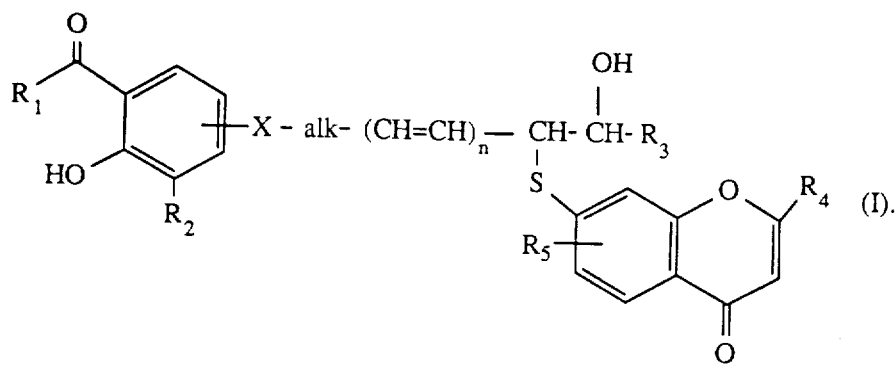

in which $R_1$ is unsubstituted or fluorinated lower alkyl, $R_2$ is hydrogen, or unsubstituted or fluorinated lower alkyl or lower alkenyl, X is lower alkylene, oxy, thio or a direct bond, alk is lower alkylene, n is 1 or 2, $R_3$ is phenyl that is unsubstituted or is substituted by unsubstituted or fluorinated lower alkyl, lower alkoxy, halogen, unsubstituted or lower alkylated amino, carboxy, lower alkoxycarbonyl, carbamoyl, N-(benzenesulfonyl)-carbamoyl that

UNITED STATES PATENT AND TRADEMARK OFFICE
CERTIFICATE OF CORRECTION

PATENT NO. : 5,149,717
DATED : September 22, 1992
INVENTOR(S) : von Sprecher, et al.

It is certified that error appears in the above-indentified patent and that said Letters Patent is hereby corrected as shown below:

is unsubstituted or substituted in the phenyl moiety by lower alkyl, lower alkoxy, halogen or a combination thereof, N-mono- or N,N-di-lower alkylcarbamoyl, or a combination thereof, or is lower alkyl that is unsubstituted or is substituted by fluoro, or fluoro and chloro, carboxy, lower alkoxycarbonyl, carbamoyl, N-mono- or N,N-di-lower alkylcarbamoyl or N-(benzenesulfonyl)-carbamoyl that is unsubstituted or substituted in the phenyl moiety by lower alkyl, lower alkoxy, halogen or a combination thereof, $R_4$ is carboxy, lower alkoxycarbonyl, carbamoyl or N-mono- or N,N-di-lower alkylcarbamoyl or N-(benzenesulfonyl)-carbamoyl that is unsubstituted or substituted in the phenyl moiety by lower alkyl, lower alkoxy, halogen or a combination thereof, or $R_4$ is 5-tetrazolyl, and $R_5$ is hydrogen or lower alkyl or a salt thereof.

Column 62,

2. A compound according to claim 1 of the formula I, in which $R_1$ is lower alkyl or mono-, di- or poly-fluoro-lower alkyl, $R_2$ is hydrogen, lower alkyl, lower alkenyl or mono-, di- or poly-fluoro-lower alkyl, X is lower alkylene, oxy, or thio, alk is lower alkylene, n is 1 or 2, $R_3$ is phenyl that is unsubstituted or is substituted by lower alkyl, lower alkoxy, carboxy, lower alkoxycarbonyl, amino, N-mono- or N,N-di-lower alkylamino, carbamoyl, N-mono- or N,N-di-lower alkylcarbamoyl, trifluoromethyl or a combination thereof, or is lower alkyl, mono-, di- or poly-fluoro-lower alkyl, mono-, di- or poly-fluoro-lower (di- or poly-chloro)alkyl, carboxy-lower alkyl, lower alkoxycarbonyl-lower alkyl,

UNITED STATES PATENT AND TRADEMARK OFFICE
CERTIFICATE OF CORRECTION

PATENT NO. : 5,149,717
DATED : September 22, 1992
INVENTOR(S) : von Sprecher, et al It is certified that error appears in the above-indentified patent and that said Letters Patent is hereby corrected as shown below:

carbamoyl-lower alkyl or N-mono- or N,N-di-lower alkylcarbamoyl-lower alkyl, $R_4$ is carboxy, lower alkoxycarbonyl, 5-tetrazolyl, carbamoyl, N-mono- or N,N-di-lower alkylcarbamoyl, or N-(benzenesulfonyl)-carbamoyl that is unsubstituted or substituted in the phenyl moiety by lower alkyl, lower alkoxy, halogen, or combinations thereof, and $R_5$ is hydrogen or lower alkyl or a salt thereof.

3. A compound according to claim 1, of formula I, in which $R_1$ is $C_1$-$C_4$-alkyl or $\omega,\omega,\omega$-trifluoro-$C_1$-$C_4$alkyl, $R_2$ is hydrogen, $C_1$-$C_4$alkyl, $C_2$-$C_4$alkylene or $\omega,\omega,\omega$-trifluoro-$C_1$-$C_4$alkyl, X is $C_1$-$C_3$alkylene, oxy or thio, alk is straight-chain $C_2$-$C_6$alkylene, n is 1 or 2, $R_3$ is phenyl that is unsubstituted or substituted by $C_1$-$C_4$alkyl, $C_1$-$C_4$alkoxy, halogen having an atomic number of up to and including 35, trifluoromethyl, carboxy, $C_1$-$C_4$alkoxycarbonyl or combinations thereof, or is $C_1$-$C_8$alkyl, $\omega,\omega,\omega$-trifluoro-$C_2$-$C_7$alkyl, $\omega,\omega,\omega,\omega$-1,$\omega$-1-pentafluoro-$C_2$-$C_7$alkyl, $\omega,\omega,\omega$-trifluoro-$\omega$-1,$\omega$-1-dichloro-$C_2$-$C_7$alkyl, carboxy-$C_2$-$C_5$alkyl or $C_1$-$C_4$alkoxycarbonyl-$C_2$-$C_5$alkyl, $R_4$ is carboxy or N-(benzenesulfonyl)-carbamoyl, and $R_5$ is hydrogen or a salt thereof.

UNITED STATES PATENT AND TRADEMARK OFFICE
CERTIFICATE OF CORRECTION

PATENT NO. : 5,149,717

DATED : September 22, 1992

INVENTOR(S) : von Sprecher, et al

It is certified that error appears in the above-indentified patent and that said Letters Patent is hereby corrected as shown below:

4. A compound according to claim 1 of formula

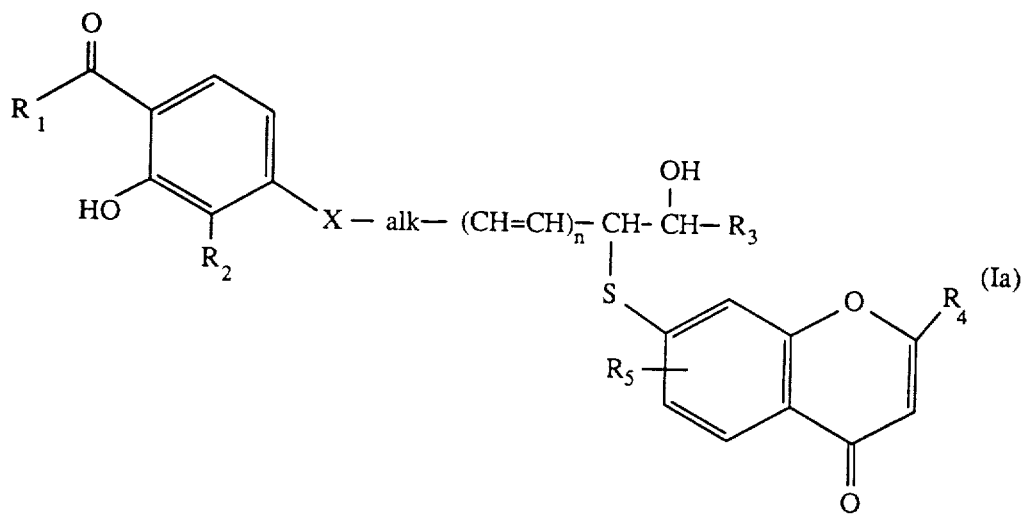

in which $R_1$ is $C_1$-$C_4$alkyl, $R_2$ is $C_1$-$C_4$alkyl, X is oxy, alk is $C_2$-$C_6$alkylene, n is 1 or 2, $R_3$ is phenyl substituted by $C_1$-$C_4$alkyl, $C_1$-$C_4$alkoxy, halogen having an atomic number of up to and including 35, trifluoromethyl or by $C_1$-$C_4$alkoxycarbonyl, or is $C_2$-$C_8$alkyl, $\omega,\omega,\omega$-trifluoro-$C_3$-$C_7$alkyl, $\omega,\omega,\omega,\omega$-1,$\omega$-1-pentafluoro-$C_2$-$C_7$alkyl, $\omega,\omega,\omega$-trifluoro-$\omega$-1,$\omega$-1-dichloro-$C_2$-$C_7$alkyl or $C_1$-$C_4$alkoxycarbonyl-$C_1$-$C_4$alkyl, $R_4$ is carboxy, and $R_5$ is hydrogen or a salt thereof.

UNITED STATES PATENT AND TRADEMARK OFFICE
CERTIFICATE OF CORRECTION

PATENT NO. : 5,149,717
DATED : September 22, 1992
INVENTOR(S) : von Sprecher, et al It is certified that error appears in the above-indentified patent and that said Letters Patent is hereby corrected as shown below:

Columns 62-63

5. A compound according to claim 1 of formula

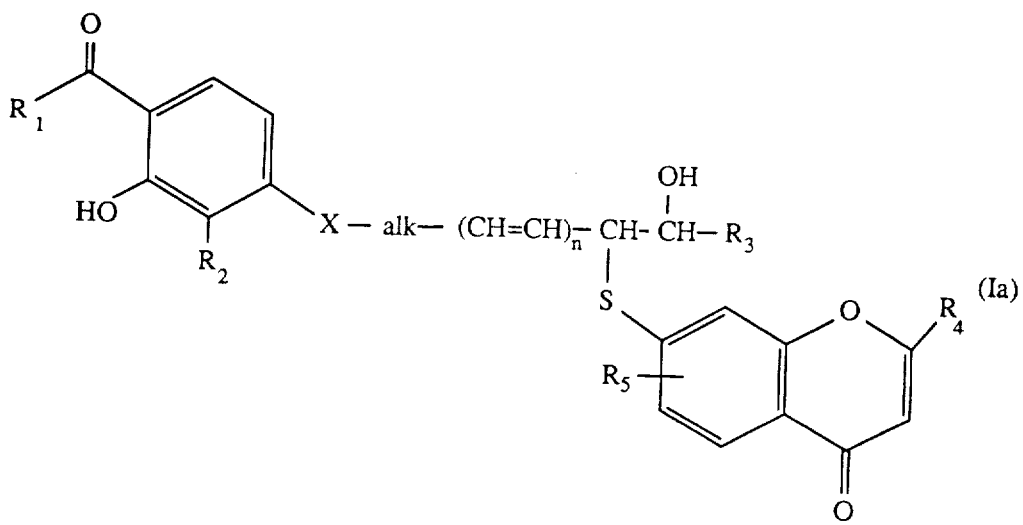

in which $R_1$ is $C_1$-$C_4$alkyl, $R_2$ is $C_1$-$C_4$alkyl, X is oxy, alk is $C_2$-$C_5$alkylene, n is 2, $R_3$ is phenyl substituted by $C_1$-$C_4$alkyl, trifluoromethyl or by $C_1$-$C_4$alkoxycarbonyl, or is $C_3$-$C_5$alkyl, $\omega,\omega,\omega$-trifluoro-$C_3$-$C_5$alkyl, $\omega,\omega,\omega,\omega$-1,$\omega$-1-pentafluoro-$C_3$-$C_7$alkyl, $\omega,\omega,\omega$-trifluoro-$\omega$-1,$\omega$-1-dichloro-$C_3$-$C_6$alkyl or $C_1$-$C_4$alkoxycarbonyl-$C_1$-$C_4$-alkyl, $R_4$ is carboxy, and $R_5$ is hydrogen or a salt thereof.

UNITED STATES PATENT AND TRADEMARK OFFICE
CERTIFICATE OF CORRECTION

PATENT NO. : 5,149,717
DATED : September 22, 1992
INVENTOR(S) : von Sprecher, et al It is certified that error appears in the above-indentified patent and that said Letters Patent is hereby corrected as shown below:

Column 63

6. A compound according to claim 2 in which the double bond adjacent to the radical alk is in the (Z)-, that is to say the *cis*-configuration, and the additional double bond which may be present is in the (E)-, that is to say the *trans*-configuration and the chain carbon atom bonded to the sulfur atom has the (S)- configuration and the chain carbon atom carrying the hydroxy group has the (R)-configuration.

7. A compound selected from the group consisting of
(1R,2S)-1-hydroxy-1-(3-trifluoromethylphenyl)-8-(4-acetyl-3-hydroxy-2-propylphenoxy)-octa-3(E),5(Z)-dien-2-yl-7-thio-4-oxo-4H-1-benzopyrane-2-carboxylic acid,
(1R,2S)-1-hydroxy-1-(3-methylphenyl)-8-(4-acetyl-3-hydroxy-2-propylphenoxy)-octa-3(E),5(Z)-dien-2-yl-7-thio-4-oxo-4H-1-benzopyrane-2-carboxylic acid,
(1R,2S)-1-hydroxy-1-(3-methoxyphenyl)-8-(4-acetyl-3-hydroxy-2-propylphenoxy)-octa-3(E),5(Z)-dien-2-yl-7-thio-4-oxo-4H-1-benzopyrane-2-carboxylic acid,
(4R,5S)-1,1,1-trifluoro-4-hydroxy-11-(4-acetyl-3-hydroxy-2-propylphenoxy)-undeca-6(E),8(Z)-dien-5-yl-7-thio-4-oxo-4H-1-benzopyrane-2-carboxylic acid,
(1R,2S)-1-hydroxy-1-(3-fluorophenyl)-10-(4-acetyl-3-hydroxy-2-propylphenoxy)-deca-3(E),5(Z)-dien-2-yl-7-thio-4-oxo-4H-1-benzopyrane-2-carboxylic acid,
(1R,2S)-1-hydroxy-1-(3-trifluoromethylphenyl)-10-(4-acetyl-3-hydroxy-2-propylphenoxy)-deca-3(E),5(Z)-dien-2-yl-7-thio-4-oxo-4H-1-benzopyrane-2-carboxylic acid,

UNITED STATES PATENT AND TRADEMARK OFFICE
CERTIFICATE OF CORRECTION

PATENT NO. : 5,149,717
DATED : September 22, 1992
INVENTOR(S) : von Sprecher, et al It is certified that error appears in the above-indentified patent and that said Letters Patent is hereby corrected as shown below:

(1R,2S)-1-hydroxy-1-(3-bromophenyl)-10-(4-acetyl-3-hydroxy-2-propylphenoxy)-deca-3(E),5(Z)-dien-2-yl-7-thio-4-oxo-4H-1-benzopyrane-2-carboxylic acid, (1R,2S)-1-hydroxy-1-(3-methylphenyl)-10-(4-acetyl-3-hydroxy-2-propylphenoxy)-deca-3(E),5(Z)-dien-2-yl-7-thio-4-oxo-4H-1-benzopyrane-2-carboxylic acid, (1R,2S)-1-hydroxy-1-(3-trifluoromethylphenyl)-9-(4-acetyl-3-hydroxy-2-propylphenoxy)-nona-3(E),5(Z)-dien-2-yl-7-thio-4-oxo-4H-1-benzopyrane-2-carboxylic acid, (1R,2S)-1-hydroxy-1-(3-trifluoromethylphenyl)-11-(4-acetyl-3-hydroxy-2-propylphenoxy)-undeca-3(E),5(Z)-dien-2-yl-7-thio-4-oxo-4H-1-benzopyrane-2-carboxylic acid, (1R,2S)-1-hydroxy-1-(3-chlorophenyl)-10-(4-acetyl-3-hydroxy-2-propylphenoxy)-deca-3(E),5(Z)-dien-2-yl-7-thio-4-oxo-4H-1-benzopyrane-2-carboxylic acid, (1R,2S)-1-hydroxy-1-(3-methoxyphenyl)-10-(4-acetyl-3-hydroxy-2-propylphenoxy)-deca-3(E),5(Z)-dien-2-yl-7-thio-4-oxo-4H-1-benzopyrane-2-carboxylic acid, and (6R,7S)-1,1,1,2,2-pentafluoro-6-hydroxy-15-(4-acetyl-3-hydroxy-2-propylphenoxy)-pentadeca-8(E),10(Z)-dien-2-yl-7-thio-4-oxo-4H-1-benzopyrane-2-carboxylic acid, or the sodium salt thereof.

Column 64, 8. (6R,7S)-1,1,1,2,2-pentafluoro-6-hydroxy-14-(4-acetyl-3-hydroxy-2-propylphenoxy)-tetradeca-8(E),10(Z)-dien-7-yl-7-thio-4-oxo-4H-1-benzopyrane-2-carboxylic acid methyl ester according to claim 1.

UNITED STATES PATENT AND TRADEMARK OFFICE
CERTIFICATE OF CORRECTION

PATENT NO. : 5,149,717

DATED : September 22, 1992

INVENTOR(S) : von Sprecher, et al

Page 8 of 9

It is certified that error appears in the above-indentified patent and that said Letters Patent is hereby corrected as shown below:

9. (1R,2S)-1-hydroxy-1-(3-trifluoromethylphenyl)-10-(4-acetyl-3-hydroxy-2-propylphenoxy)-deca-3(E),5(Z)-dien-2-yl-7-thio-4-oxo-4H-1-benzopyrane-2-carboxylic acid according to claim 1 or the sodium salt thereof.

10. (1R,2S)-1-hydroxy-1-phenyl-10-(4-acetyl-3-hydroxy-2-propylphenoxy)-deca-3(E),5(Z)-dien-2-yl-7-thio-4-oxo-4H-1-benzopyrane-2-carboxylic acid according to claim 1 or the sodium salt thereof.

11. A pharmaceutical preparation for the alleviation of pathological conditions resulting from the action of leucotrienes containing as pharmaceutical active ingredient, a therapeutically effective amount of a compound according to claim 1.

12. A pharmaceutical preparation according to claim 11, wherein the compound used is (1R,2S)-1-hydroxy-1-(3-trifluoromethylphenyl)-10-(4-acetyl-3-hydroxy-2-propylphenoxy)-deca-3(E),5(Z)-dien-2-yl-7-thio-4-oxo-4H-1-benzopyrane-2-carboxylic acid, or the sodium salt thereof.

13. A method for the treatment of allergic diseases in a patient in need of such treatment, which method comprises the administration

UNITED STATES PATENT AND TRADEMARK OFFICE
CERTIFICATE OF CORRECTION

PATENT NO. : 5,149,717

DATED : September 22, 1992

INVENTOR(S) : von Sprecher, et al

It is certified that error appears in the above-indentified patent and that said Letters Patent is hereby corrected as shown below:

of a therapeutically effective amount of a compound according to claim 1.

14. A method according to claim 13, wherein the compound used is (1R,2S)-1-hydroxy-1-(3-trifluoromethylphenyl)-10-(4-acetyl-3-hydroxy-2-propylphenoxy)-deca-3(E),5(Z)-dien-2-yl-7-thio-4-oxo-4H-1-benzopyrane-2-carboxylic acid, or the sodium salt thereof.--

Signed and Sealed this

Twenty-sixth Day of October, 1993

*Attest:*

BRUCE LEHMAN

*Attesting Officer*     Commissioner of Patents and Trademarks